United States Patent
Kashyap

(10) Patent No.: US 11,351,420 B2
(45) Date of Patent: *Jun. 7, 2022

(54) METHOD AND SYSTEM FOR VIRTUAL FITNESS TRAINING AND TRACKING DEVICES

(71) Applicant: Smartweights, Inc., Irvine, CA (US)

(72) Inventor: Praveen Kashyap, Irvine, CA (US)

(73) Assignee: SMARTWEIGHTS, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/107,634

(22) Filed: Nov. 30, 2020

(65) Prior Publication Data

US 2021/0086030 A1 Mar. 25, 2021

Related U.S. Application Data

(63) Continuation-in-part of application No. 15/553,006, filed as application No. PCT/US2016/019199 on Feb. 23, 2016, now Pat. No. 10,081,907.

(Continued)

(51) Int. Cl.
*A63B 24/00* (2006.01)
*A63B 21/00* (2006.01)
(Continued)

(52) U.S. Cl.
CPC ...... *A63B 24/0062* (2013.01); *A63B 21/0628* (2015.10); *A63B 21/0724* (2013.01);
(Continued)

(58) Field of Classification Search
CPC ............ A63B 24/0062; A63B 24/0075; A63B 2024/0065; A63B 2024/0068; A63B 2024/0071; A63B 2024/0081
See application file for complete search history.

(56) References Cited

U.S. PATENT DOCUMENTS 8,738,925 B1   5/2014 Park et al.
9,656,120 B1 * 5/2017 Franco ............... A63B 71/0622
(Continued)

OTHER PUBLICATIONS

International Search Report for Serial No. PCT/US2016/19199 dated Aug. 8, 2016.

*Primary Examiner* — William H McCulloch, Jr.
(74) *Attorney, Agent, or Firm* — Concept IP LLP; Michael Zarrabian

(57) ABSTRACT

A machine implemented method and system, including: transmitting one or more credentials of a user account from a user device to an exercise management system (EMS) having a processor and one or more sensors, where the EMS is disposed on an exercise equipment disposed in a selected at least one fitness center and the exercise equipment is part of a selected at least one exercise plan; transmitting the one or more credentials of the user account from the EMS to a cloud server having a processor; transmitting the selected at least one exercise plan for the new user account from the cloud server to the EMS; transmitting an exercise equipment information from the EMS; forming a user exercise data by the EMS for the exercise equipment based on data received from the one or more sensors; and transmitting an exercise feedback from the EMS.

13 Claims, 42 Drawing Sheets

Related U.S. Application Data

(60) Provisional application No. 62/961,100, filed on Jan. 14, 2020, provisional application No. 62/119,725, filed on Feb. 23, 2015.

(51) Int. Cl.

| | | |
|---|---|---|
| *A63B 21/062* | (2006.01) | |
| *G16H 20/30* | (2018.01) | |
| *G06N 20/00* | (2019.01) | |
| *A63B 21/072* | (2006.01) | |

(52) U.S. Cl.
CPC ........... *A63B 21/154* (2013.01); *G06N 20/00* (2019.01); *G16H 20/30* (2018.01); *A63B 24/0075* (2013.01); *A63B 2220/17* (2013.01); *A63B 2220/20* (2013.01); *A63B 2220/30* (2013.01); *A63B 2220/40* (2013.01); *A63B 2220/833* (2013.01); *A63B 2225/20* (2013.01); *A63B 2225/54* (2013.01); *A63B 2230/75* (2013.01)

(56) References Cited

U.S. PATENT DOCUMENTS

| | | | |
|---|---|---|---|
| 10,065,074 B1 | 9/2018 | Hoang et al. | |
| 10,610,733 B2* | 4/2020 | Pendergast | A63B 24/0003 |
| 10,765,900 B2* | 9/2020 | Lacey | A63B 21/00069 |
| 10,881,907 B2* | 1/2021 | Kashyap | G06Q 10/06311 |
| 10,918,901 B2* | 2/2021 | Orfield | H04M 1/725 |
| 10,987,542 B2* | 4/2021 | Nejezchleb | G06K 9/00342 |
| 11,011,263 B2* | 5/2021 | Burich | G16H 40/67 |
| 11,040,231 B2* | 6/2021 | Rubin | A63B 21/153 |
| 11,099,089 B2* | 8/2021 | Goodstadt | A63B 21/0628 |
| 11,103,750 B2* | 8/2021 | Wiebe | A61B 5/486 |
| 2004/0010420 A1 | 1/2004 | Rooks | |
| 2007/0219059 A1 | 9/2007 | Schwartz et al. | |
| 2007/0232455 A1 | 10/2007 | Hanoun | |
| 2008/0119763 A1 | 5/2008 | Wiener | |
| 2008/0242512 A1 | 10/2008 | Kim et al. | |
| 2008/0261776 A1 | 10/2008 | Skiba | |
| 2013/0297669 A1 | 11/2013 | Wang | |
| 2014/0059066 A1 | 2/2014 | Koloskov | |
| 2014/0073252 A1 | 3/2014 | Lee et al. | |
| 2014/0235166 A1 | 8/2014 | Molettiere et al. | |
| 2014/0266160 A1 | 9/2014 | Coza | |
| 2015/0038806 A1 | 2/2015 | Kaleal, III et al. | |
| 2015/0082408 A1 | 3/2015 | Yeh et al. | |
| 2015/0126332 A1 | 5/2015 | Lannon et al. | |
| 2015/0151161 A1 | 6/2015 | Anderton | |
| 2015/0265903 A1 | 9/2015 | Kolen et al. | |
| 2016/0199697 A1 | 7/2016 | Orfield | |
| 2017/0128765 A1* | 5/2017 | Garretson | G06V 40/23 |
| 2017/0361165 A1 | 12/2017 | Miller et al. | |
| 2018/0050234 A1 | 2/2018 | Kashyap | |
| 2018/0117381 A1 | 5/2018 | Ismail | |
| 2018/0117417 A1 | 5/2018 | Davis | |
| 2020/0121968 A1* | 4/2020 | Ismail | A63B 21/0552 |
| 2021/0086030 A1* | 3/2021 | Kashyap | G16H 20/30 |
| 2021/0128971 A1* | 5/2021 | Orfield | A63B 21/0724 |
| 2021/0128979 A1* | 5/2021 | McHugh | H04Q 9/00 |
| 2021/0387055 A1* | 12/2021 | Miller | A63B 69/3621 |
| 2021/0394020 A1* | 12/2021 | Killen | A63B 24/0006 |
| 2021/0402259 A1* | 12/2021 | Belson | A63B 24/0087 |
| 2022/0008775 A1* | 1/2022 | Rubin | A63B 21/153 |

\* cited by examiner

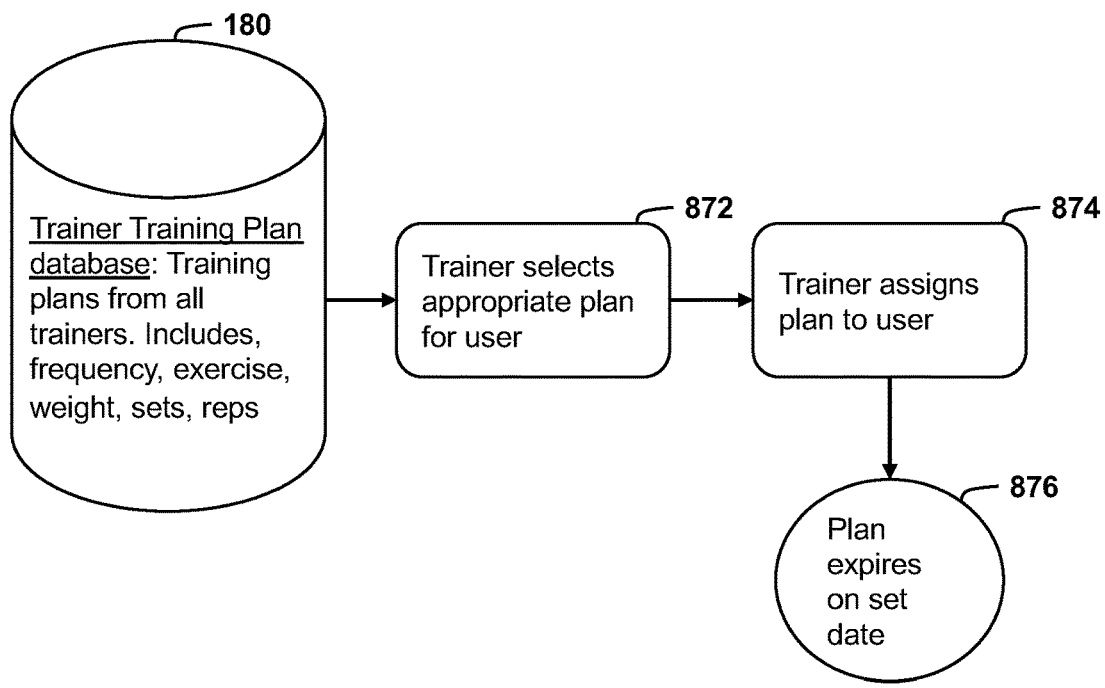
FIG. 3B-i

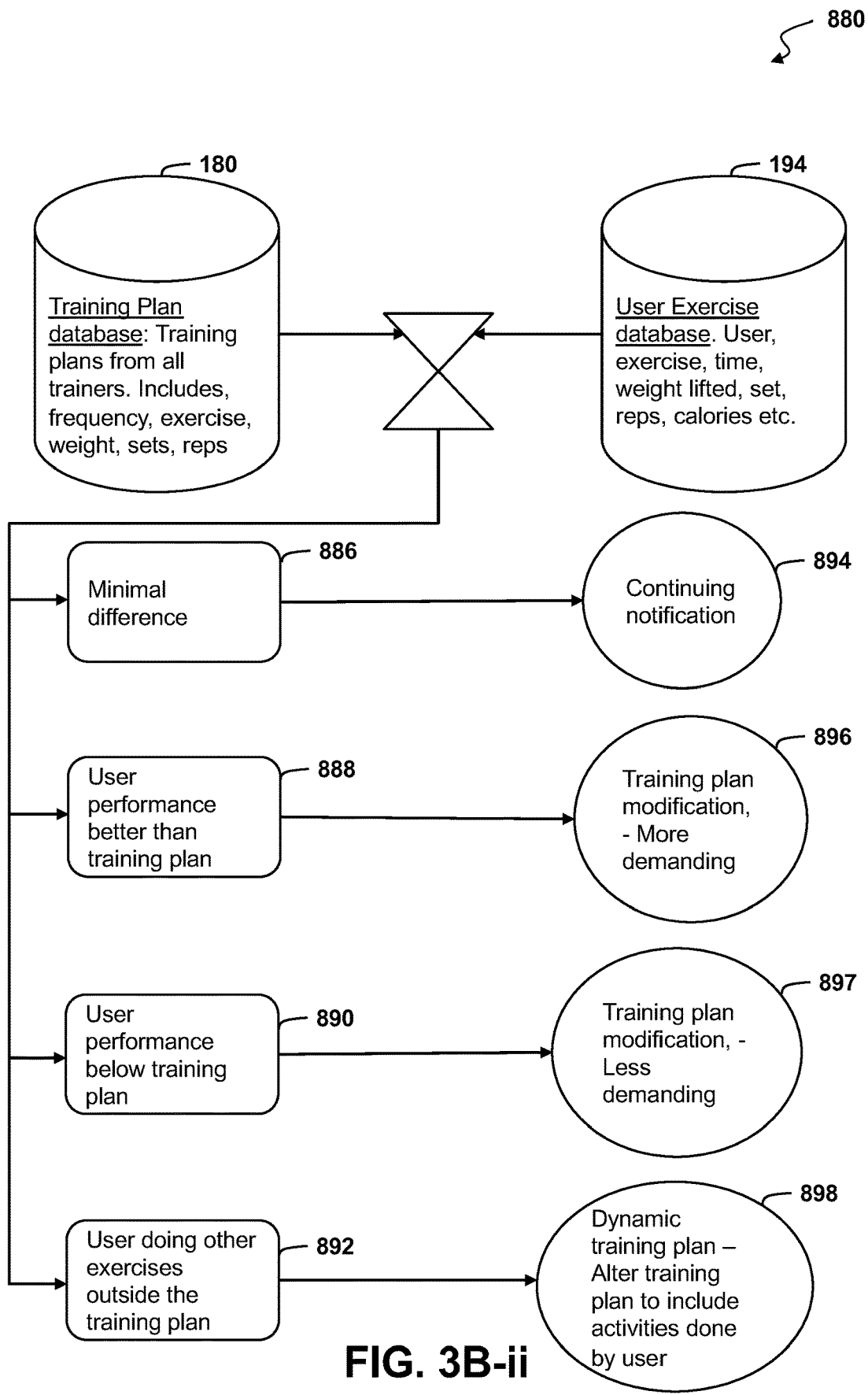
FIG. 3B-ii

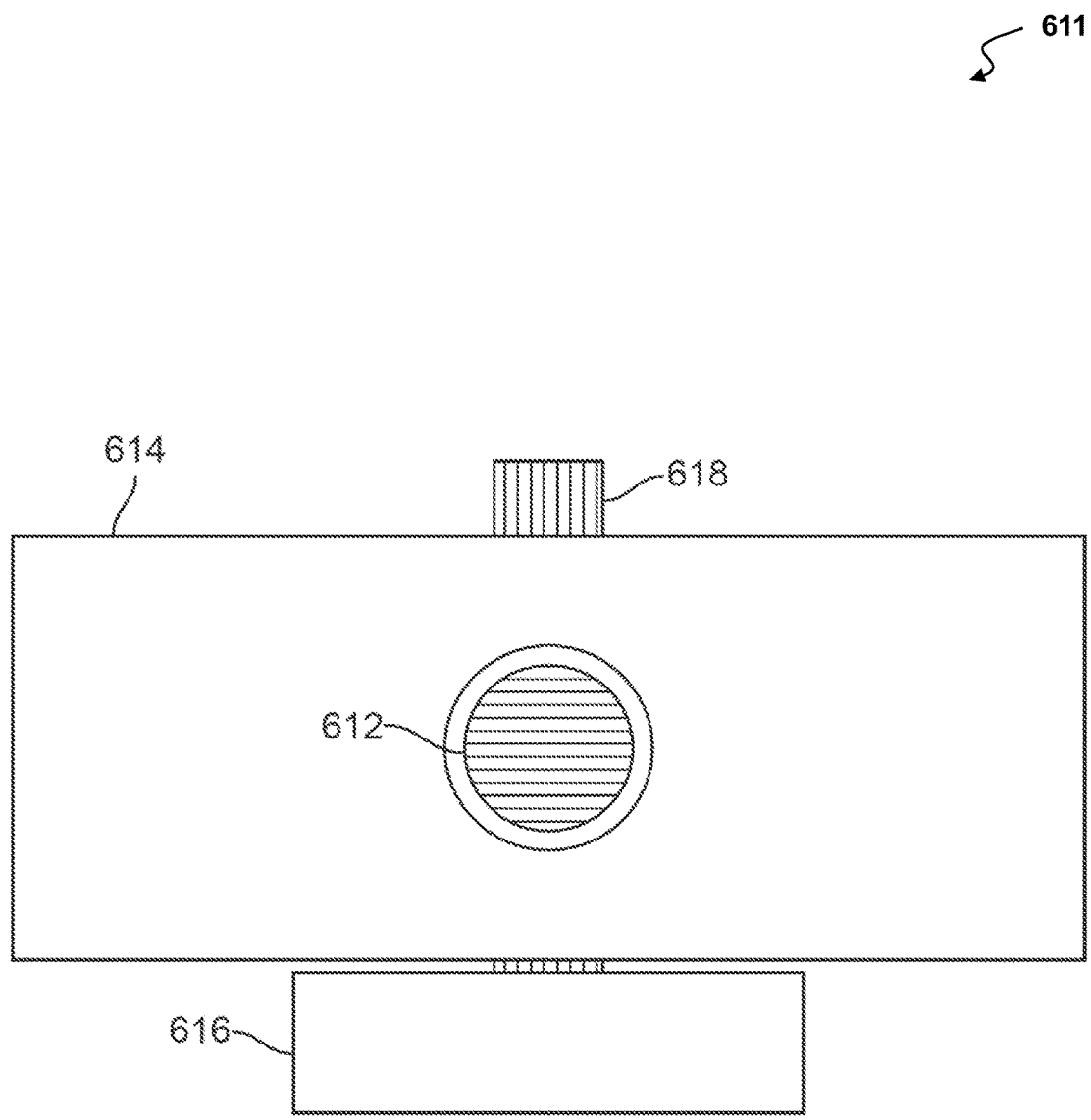
FIG. 4B-i

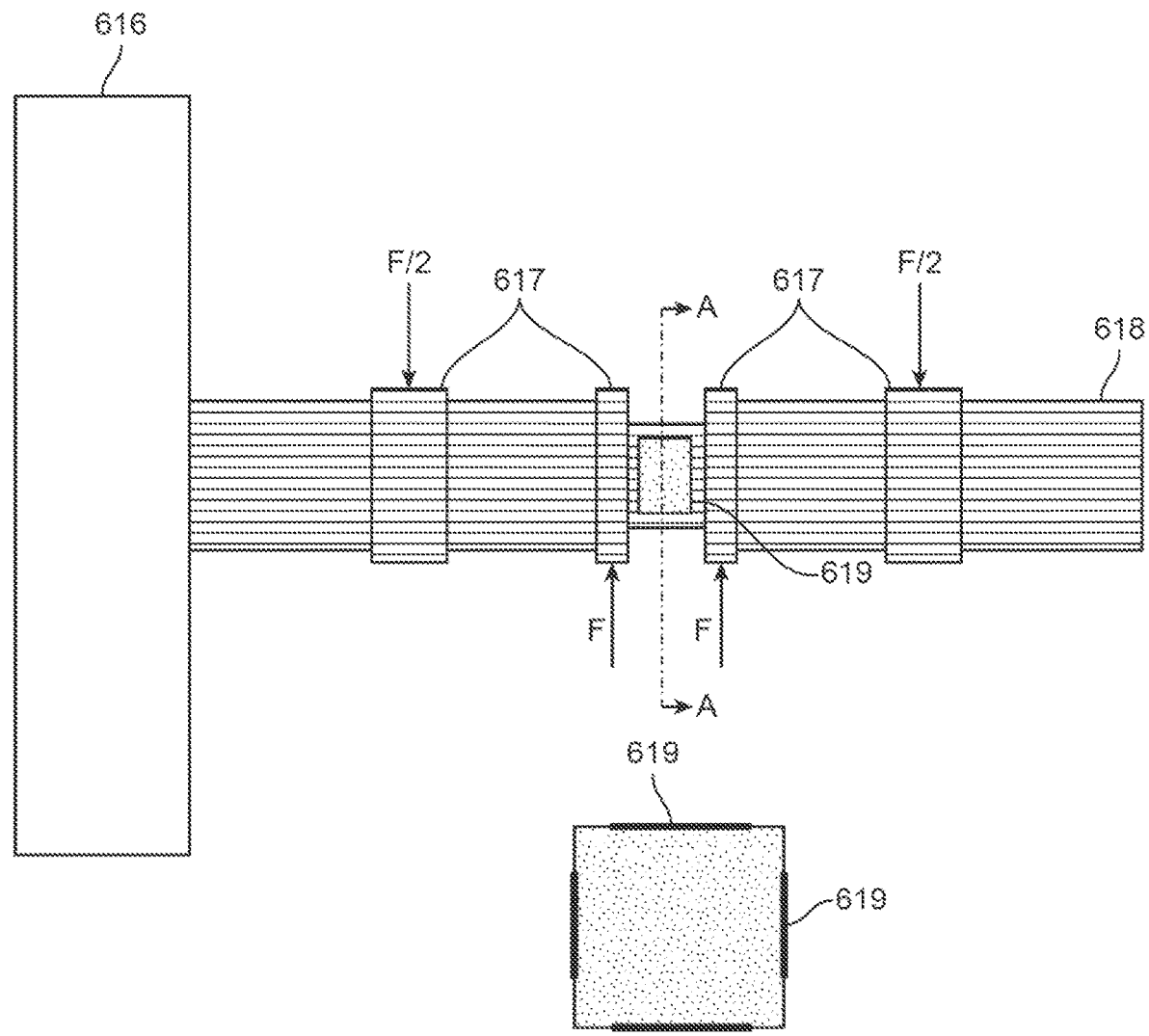
FIG. 4B-ii

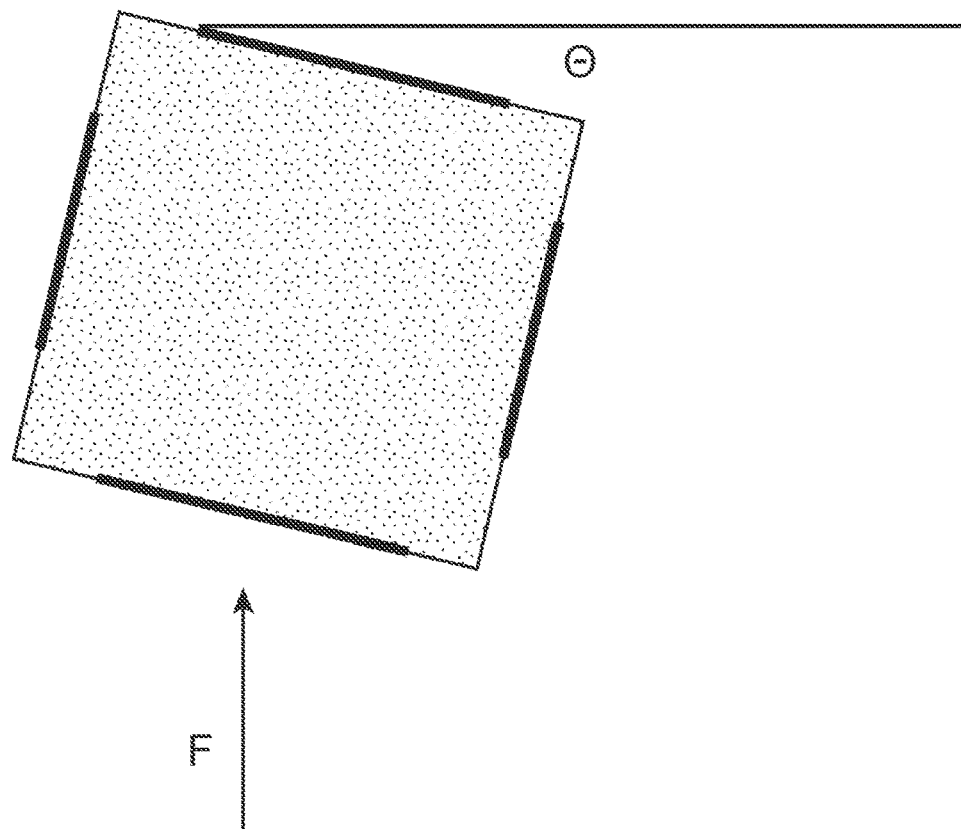
FIG. 4B-iii

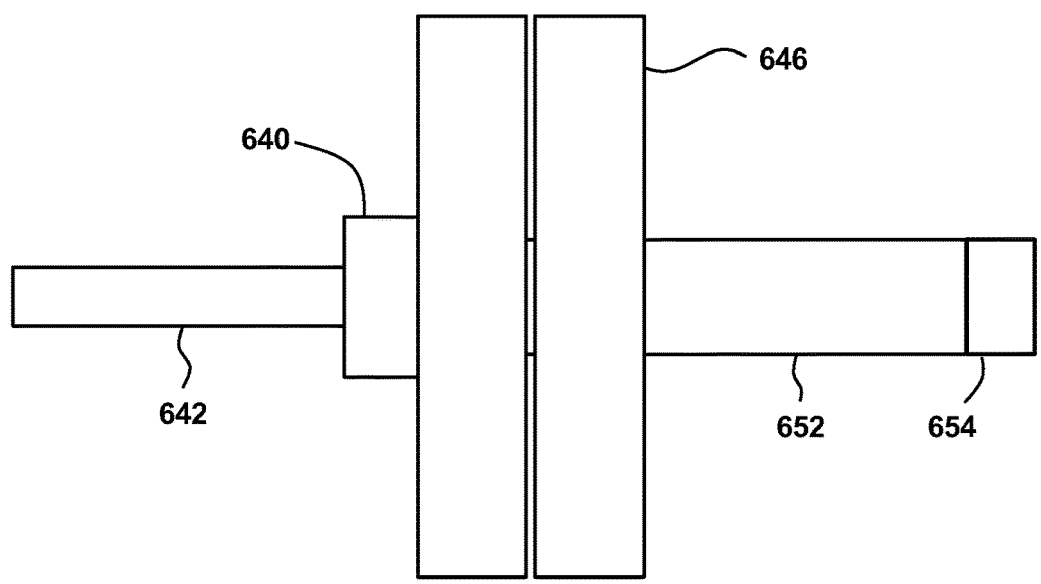
FIG. 4F-i

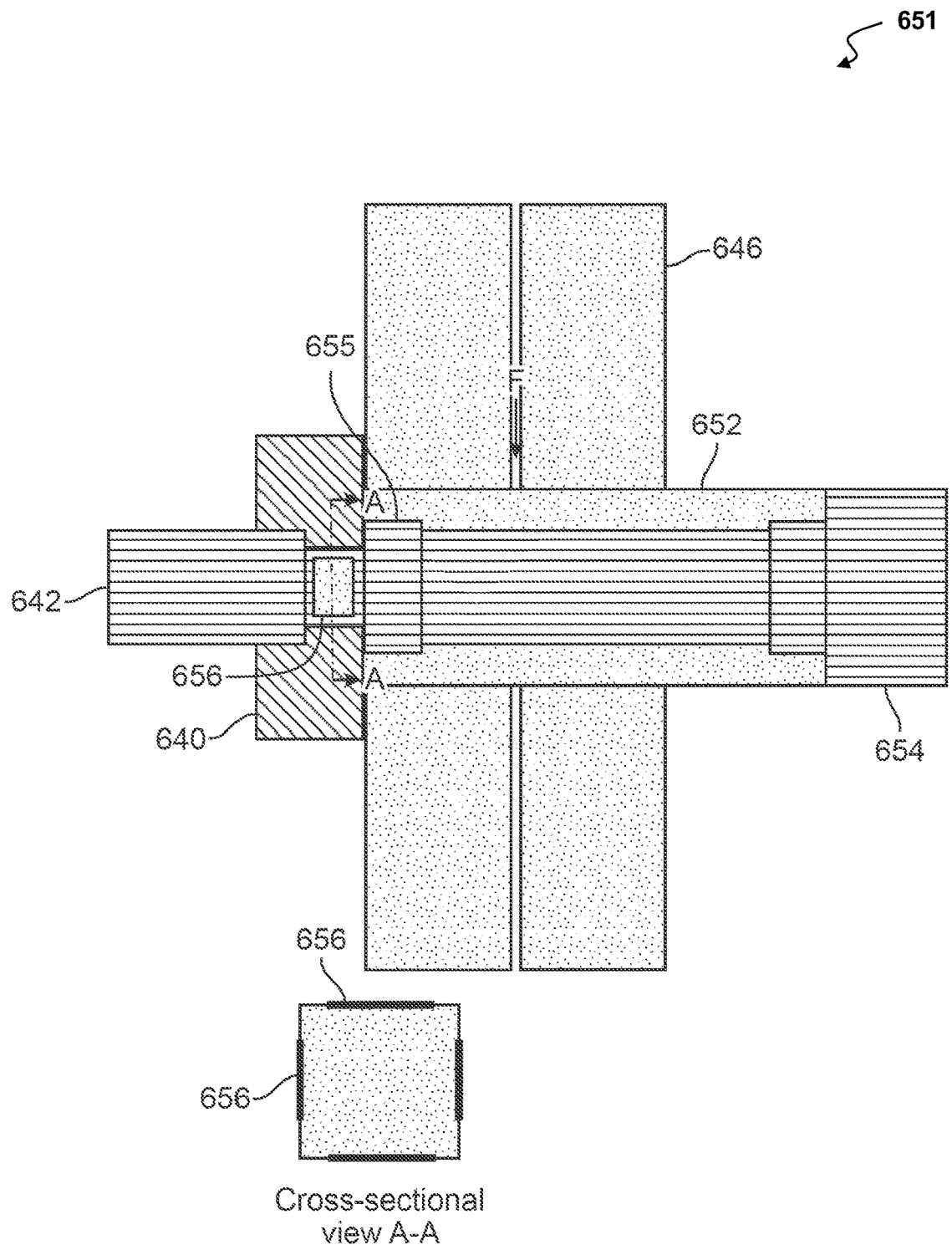
FIG. 4F-ii

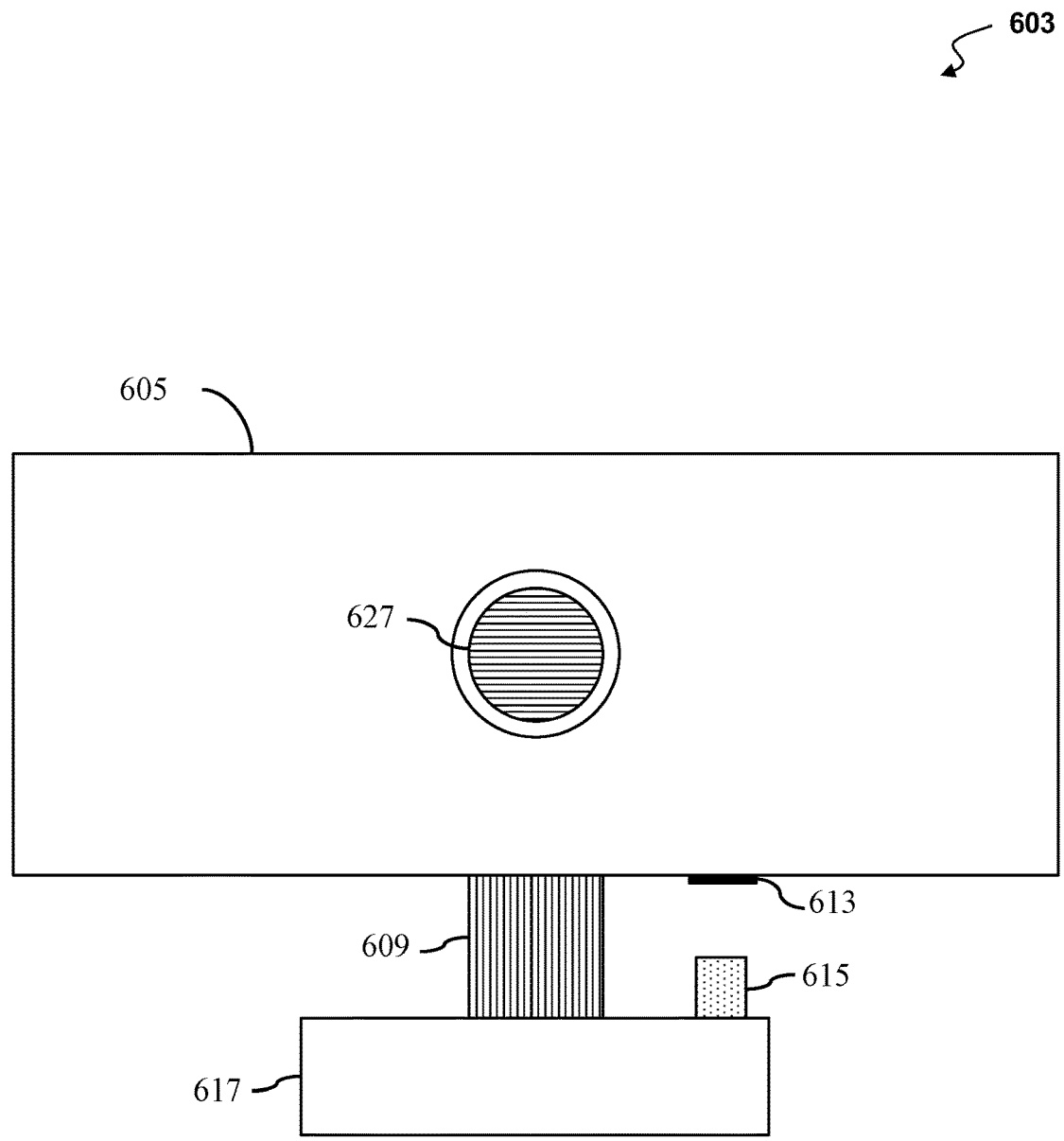
FIG. 4G-i

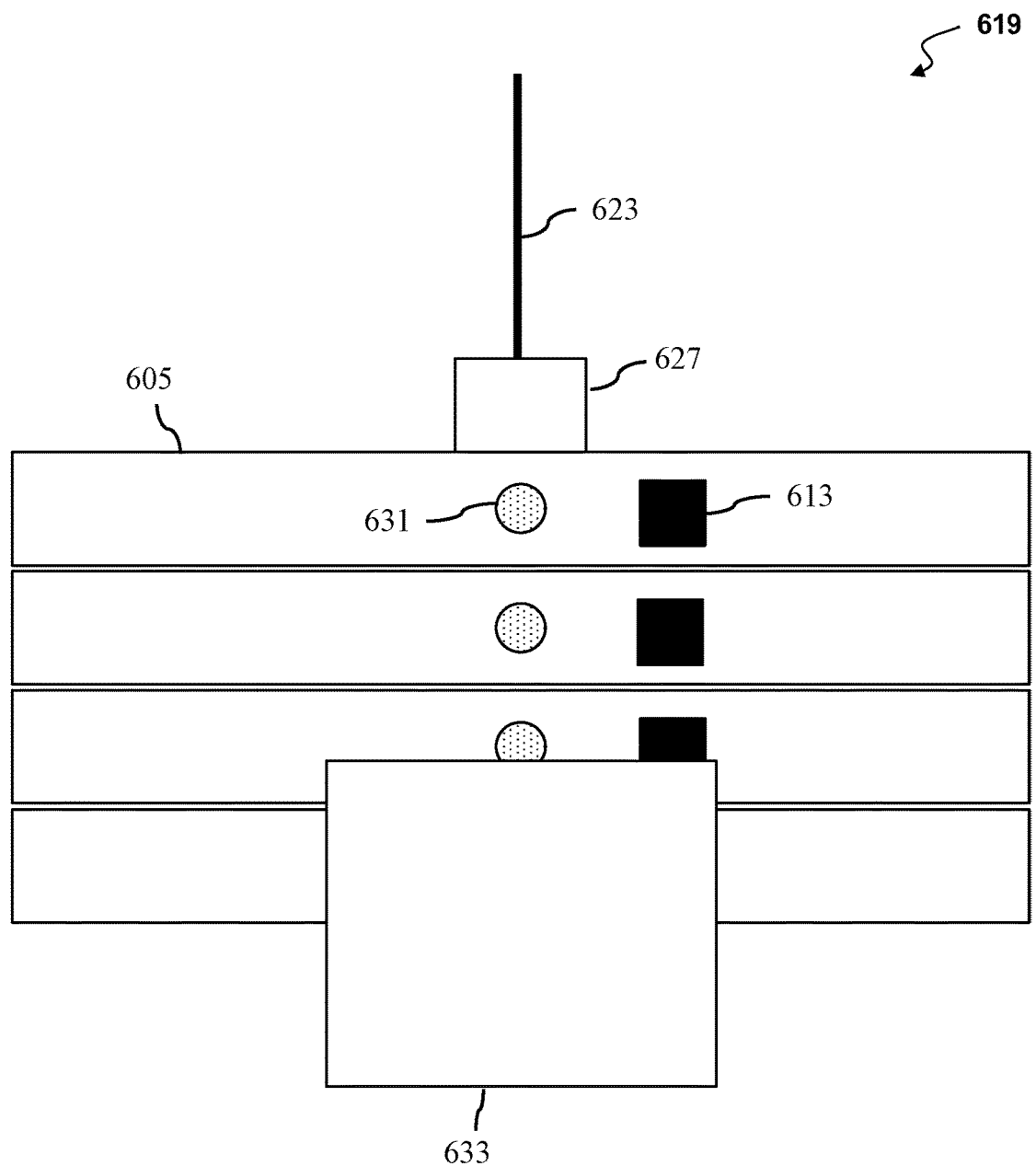
FIG. 4G-ii

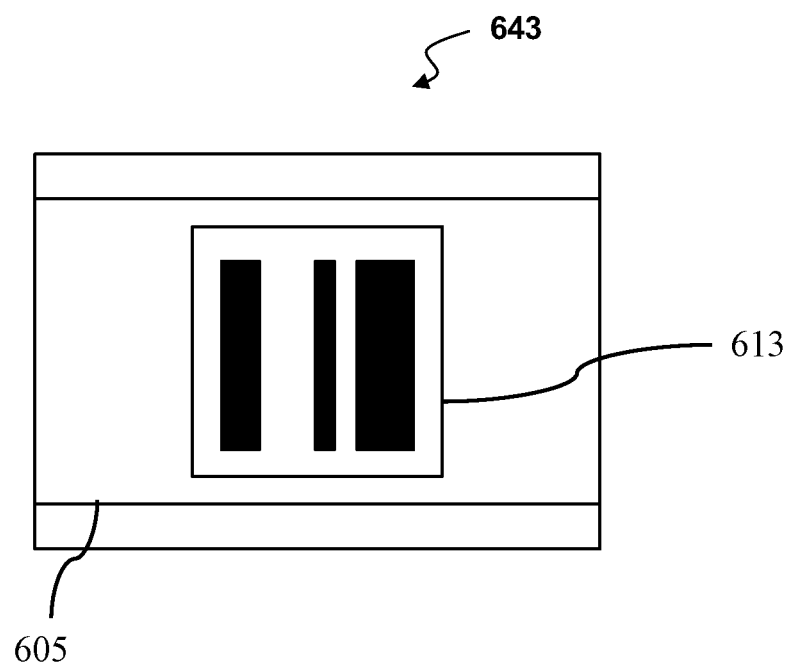
FIG. 4G-iii

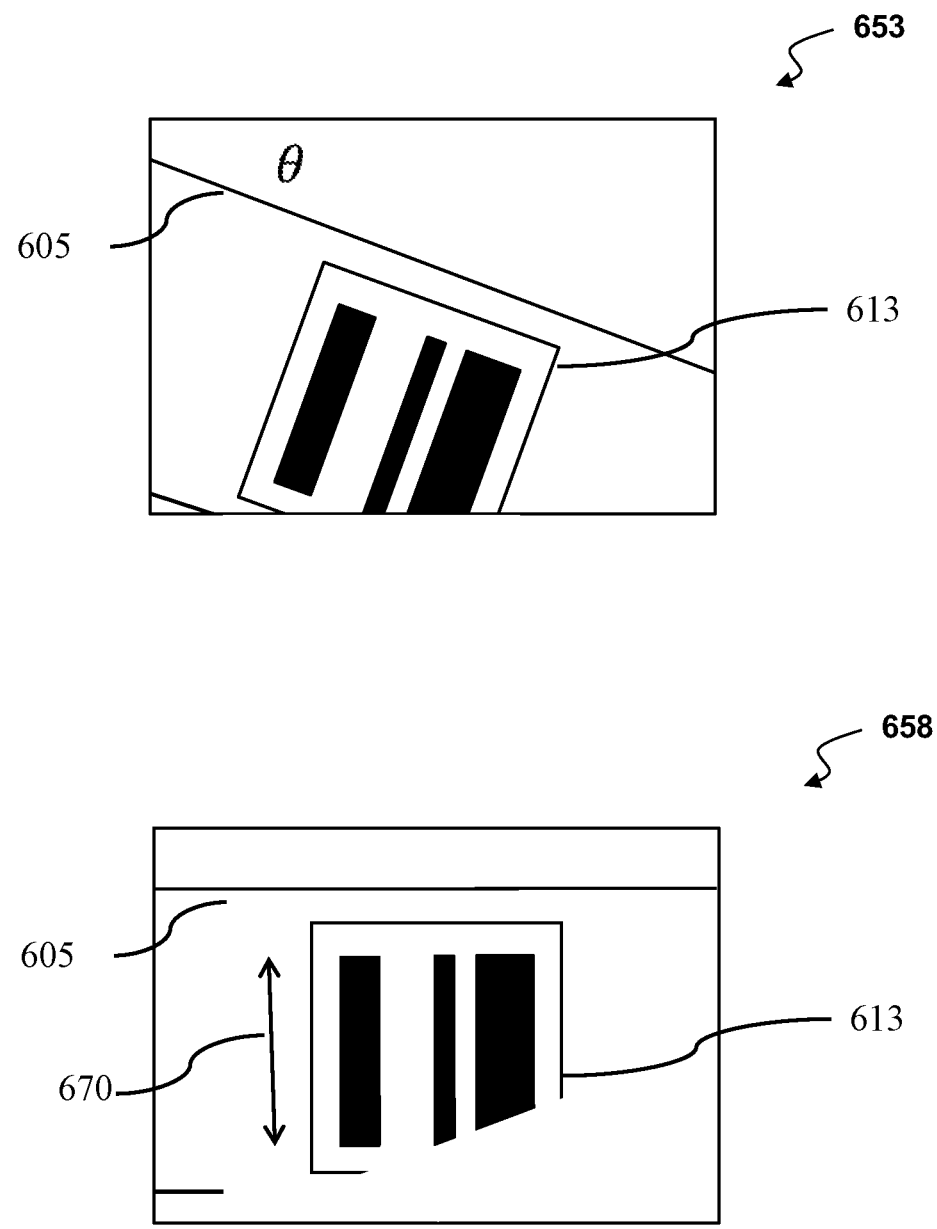
FIG. 4G-iv

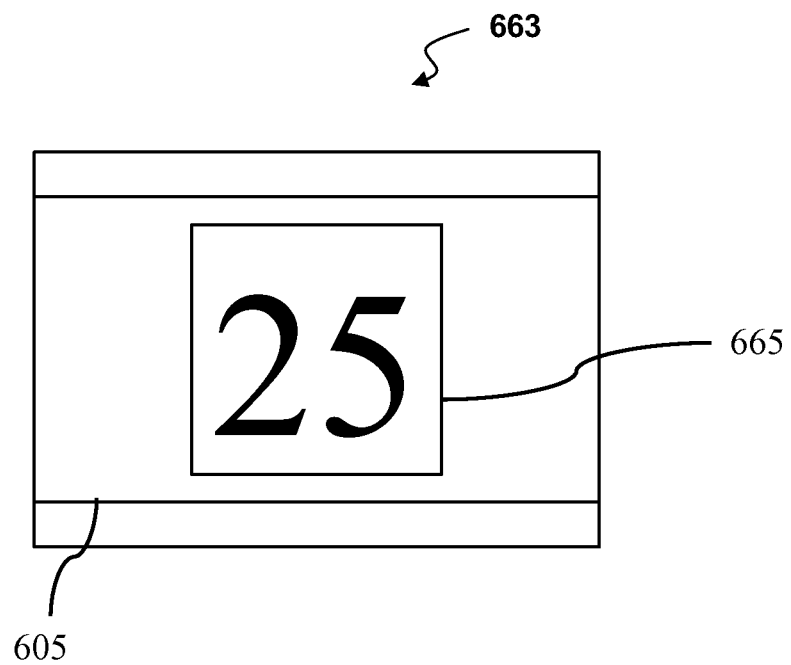
FIG. 4G-v

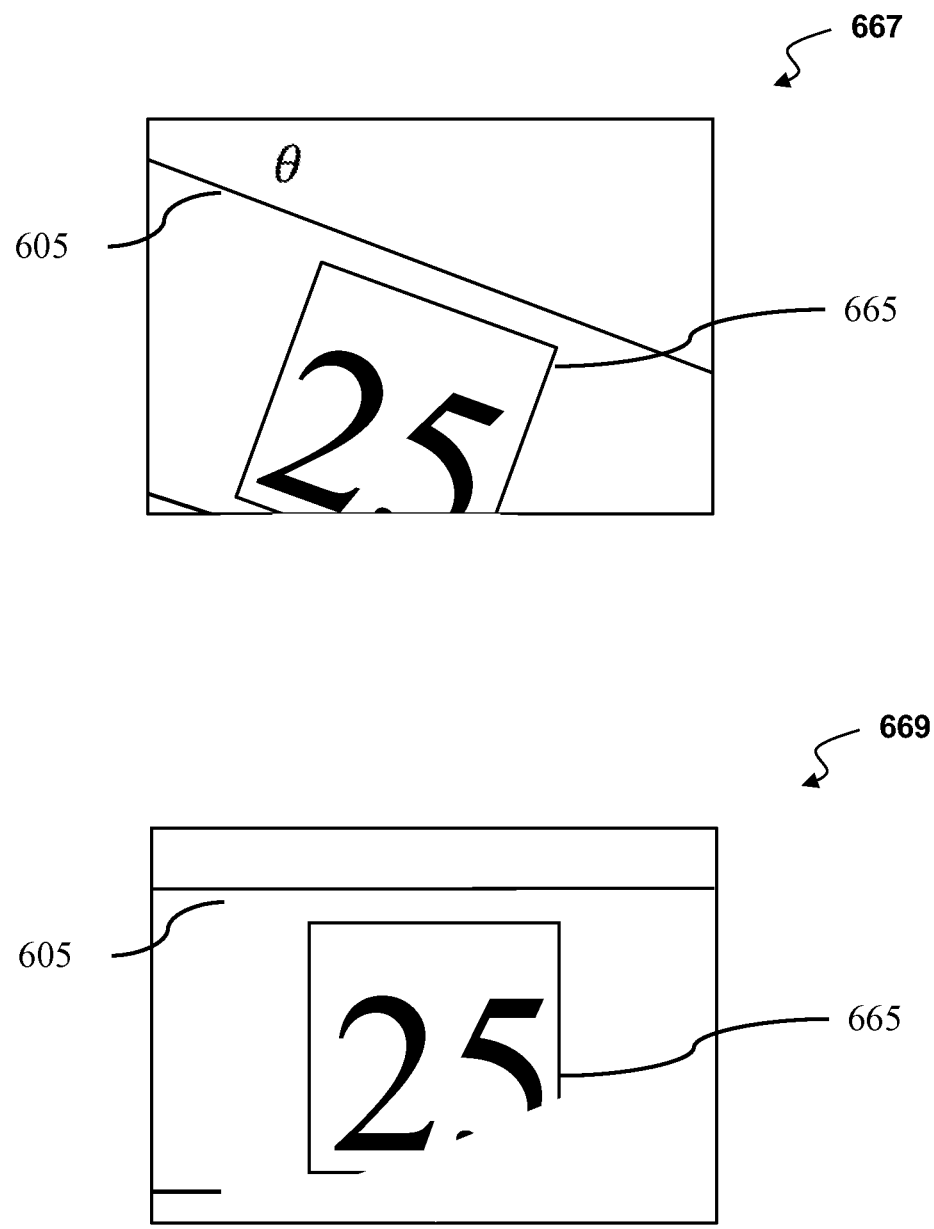
FIG. 4G-vi

METHOD AND SYSTEM FOR VIRTUAL FITNESS TRAINING AND TRACKING DEVICES

CROSS-REFERENCE TO RELATED APPLICATIONS

This application is a continuation-in-part of U.S. Non-Provisional patent application Ser. No. 15/553,006, filed Aug. 23, 2017, which is a U.S. National Phase Patent Application under 35 U.S.C. § 371 of International Application Number PCT/US2016/019199, filed Feb. 23, 2016, which claims the priority benefit of U.S. Provisional Patent Application Ser. No. 62/119,725, filed Feb. 23, 2015, and this application claims priority to U.S. Provisional Patent Application No. 62/961,100, filed Jan. 14, 2020, all of which are hereby incorporated herein by reference in their entirety for all purposes.

TECHNICAL FIELD

Embodiments relate generally to the Internet of Things (IoT), and more particularly to providing virtual training and tracking services for health and fitness.

BACKGROUND

A user selected fitness training program typically involves use of cardio machines, weight machines, free weights, etc. The user has to remember, or write down, which machine to use, the order in which they are to be used, and track how much weight they are lifting, the number of sets, repetitions, etc.

SUMMARY

An exemplary machine implemented method may include: transmitting one or more credentials of a user account from a user device to an exercise management system (EMS) having a processor and one or more sensors, where the EMS may be disposed on an exercise equipment disposed in a selected at least one fitness center, where the exercise equipment may be part of a selected at least one exercise plan; transmitting the one or more credentials of the user account from the EMS to a cloud server having a processor; transmitting the selected at least one exercise plan for the new user account from the cloud server to the EMS; transmitting an exercise equipment information based on the exercise equipment and the selected at least one exercise plan from the EMS; forming a user exercise data by the EMS for the exercise equipment based on data received from the one or more sensors; and transmitting an exercise feedback from the EMS based on a comparison of the formed user exercise data and the selected at least one exercise plan.

Additional method embodiments may include, determining a difference between the formed user exercise data and the selected at least one exercise plan at the cloud server; if the difference between the formed user exercise data and the selected at least one exercise plan is minimal: maintaining the selected at least one exercise plan at the cloud server; if the difference between the formed user exercise data and the selected at least one exercise plan shows a greater user performance: modifying the selected at least one exercise plan to an increased difficulty at the cloud server; if the difference between the formed user exercise data and the selected at least one exercise plan shows a lower user performance: modifying the selected at least one exercise plan to a decreased difficulty at the cloud server; and if the difference between the formed user exercise data and the selected at least one exercise plan shows an exercise equipment not in the selected at least one exercise plan: modifying the selected at least one exercise plan to add the exercise equipment to the selected at least one exercise plan at the cloud server. In additional method embodiments, the exercise equipment information may include one or more of: exercise equipment settings, an exercise technique for the exercise equipment, a weight to be lifted, a duration, a number of repetitions, and a number of sets. In additional method embodiments, the user device may include one or more of: a smart phone having a processor, a near field communication (NFC) tag, and a radio-frequency identification (RFID) tag. Additional method embodiments may include, transmitting the formed new user exercise data for the exercise equipment from the EMS to the cloud server; and generating a new record in a new user exercise summary database at the cloud server, where the new user exercise summary includes the formed new user exercise data.

Additional method embodiments may include, transmitting the formed new user exercise data for the exercise equipment from the EMS to the user device. Additional method embodiments may include, prior to transmitting one or more credentials of the user account: transmitting a user account request from the user device having a processor to the cloud server; generating at the cloud server the user account containing information transmitted by the user device; transmitting a list of fitness centers from the cloud server to the user device; transmitting a selection of at least one of the list of fitness centers from the user device to the cloud server; transmitting a list of exercise plans based on the selected at least one of the list of fitness centers from the cloud server to the user device; and transmitting a selection of at least one exercise plan of the list of exercise plans from the user device to the cloud server. In additional method embodiments, the one or more sensors may include one or more of: an accelerometer, a gyroscope, a weight meter, a tension meter, a pulse meter, a proximity sensor, and a barcode reader. In additional method embodiments, the formed user exercise data may include one or more of: a weight used, a number of sets, a number of repetitions, a lifting speed, a range, an energy, a maximum power, and a total calories spent.

Another exemplary machine implemented method may include: enabling by a trainer device having a processor, a recording mode for an exercise management system (EMS) having a processor and one or more sensors, where the EMS may be disposed on an exercise equipment disposed in a fitness center; forming by the EMS, one or more exercise details based on data from the one or more sensors; transmitting by the EMS, the formed data to a cloud server having a processor; forming by the cloud server, a training plan for a trainer that includes the formed data.

In additional method embodiments, the training plan may include one or more of: a weight of an exercise for the fitness equipment, a number of sets for the exercise for the fitness equipment, a number of repetitions for the exercise for the fitness equipment, a lifting speed for the exercise for the fitness equipment, and a range for the exercise for the fitness equipment. Additional method embodiments may include, prior to enabling the recording mode: transmitting a trainer account request from a trainer device to the cloud server; generating at the cloud server, a trainer account containing information transmitted by the trainer device. In additional method embodiments, the one or more sensors may include one or more of: an accelerometer, a gyroscope, a weight meter, a tension meter, a pulse meter, and a proximity sensor, and a barcode reader.

An exemplary system embodiment may include: an Exercise Management System (EMS) including: one or more sensors; and a processor having memory, the processor configured to: pair a user device to the EMS; receive one or more credentials of a user account from the user device; transmit the one or more credentials of the user account to a cloud server; receive an exercise plan for the user account from the cloud server; form a user exercise data for an exercise equipment based on data received from the one or more sensors; and transmit an exercise feedback based on a comparison of the formed user exercise data and the received exercise plan.

In additional system embodiments, where the formed user exercise data comprises one or more of: a weight used, a number of sets, a number of repetitions, a lifting speed, a range, an energy, a maximum power, and a total calories spent. In additional system embodiments, the EMS processor may be further configured to: transmit the formed user exercise data for the exercise equipment to the cloud server; and unpair the user device from the EMS. In additional system embodiments, the one or more sensors may further include: a tension meter of the one or more sensors disposed on a cable of the exercise equipment, where the tension meter measures a weight lifted; and one or more motion sensors of the one or more sensors disposed on the cable of the exercise equipment, where the one or more motion sensors measure a movement of the weight lifted. In additional system embodiments, the one or more motion sensors include an accelerometer and a gyroscope. In additional system embodiments, the weight sensor includes one or more of: a load cell type weight sensor and a tension meter. In additional system embodiments, the weight pin further includes one or more pin relief features, where the one or more pin relief features concentrates the weight and support forces on one or more predefined and fixed areas of the weight pin. In additional system embodiments, the weight pin further includes a barcode reader, or a camera and each weight may have a unique barcode or symbol which may be read by the barcode reader or the camera.

In additional system embodiments, the one or more sensors further include: a weight sensor of the one or more sensors disposed in a weight pin of the exercise equipment, where the weight sensor measures a weight lifted; and one or more motion sensors of the one or more sensors mounted on the weight pin, where the one or more motion sensors measure a movement of the weight lifted, and where the weight pin compensates for an orientation of the weight pin with respect to ground. In additional system embodiments, the one or more motion sensors include an accelerometer and a gyroscope. In additional system embodiments, the weight sensor includes one or more of: a load cell type weight sensor and a tension meter. In additional system embodiments, the weight pin further includes one or more pin relief features, where the one or more pin relief features concentrates the weight and support forces on one or more predefined and fixed areas of the weight pin. In additional system embodiments, the weight pin further includes a barcode reader, or a camera. In one embodiment, each weight may have a unique barcode which may be read by the barcode reader or the camera. In another embodiment, each weight may have a unique symbol that may be read by the camera. The symbol may be read by the camera using Optical Character Recognition, Pattern recognition, or Machine Learning technologies.

In additional system embodiments, the one or more sensors further include: a weight sensor of the one or more sensors disposed in a weight pin of the exercise equipment, where the weight sensor measures a weight lifted; and a rotation sensor of the one or more sensors disposed about the weight pin, where the rotation sensor measures the movement of a cable of the exercise equipment about a rotatable pulley. In additional system embodiments, the weight sensor includes one or more of: a load cell type weight sensor and a tension meter. In additional system embodiments, the weight pin further comprises one or more pin relief features, where the one or more pin relief features concentrates the weight and support forces on one or more predefined and fixed areas of the weight pin. In additional system embodiments, the weight pin further includes a barcode reader, or a camera and each weight may have a unique barcode which may be read by the barcode reader or the camera.

In additional system embodiments, the one or more sensors further include: a weight sensor of the one or more sensors disposed in on support of the exercise equipment, where the weight sensor measures a weight lifted; and one or more motion sensors of the one or more sensors mounted on a barbell, where the one or more motion sensors measure a movement of the weight lifted; where the weight sensor communicates with the one or more motion sensors. In additional system embodiments, the one or more motion sensors include an accelerometer and a gyroscope. In additional system embodiments, the weight sensor includes one or more of: a load cell type weight sensor and a tension meter. In additional system embodiments, the EMS processor is further configured to: determine a type of exercise performed based on a range of motion recorded by the one or more sensors.

In additional system embodiments, the one or more sensors further include: a weight sensor of the one or more sensors disposed in a barbell of the exercise equipment, where the weight sensor measures a weight lifted; and one or more motion sensors of the one or more sensors mounted on a sleeve of the barbell, where the one or more motion sensors measure a movement of the weight lifted, and where the weight sensor compensates for an orientation of the barbell with respect to ground. In additional system embodiments, the one or more motion sensors include an accelerometer and a gyroscope. In additional system embodiments, the weight sensor includes one or more of: a load cell type weight sensor and a tension meter.

An exemplary machine implemented method may include: receiving acceleration data from one or more sensors at an exercise management system (EMS) having a processor; applying at the EMS, a first high pass filter to the received acceleration data; determining at the EMS, a velocity of the filtered acceleration data by integration; applying at the EMS, a velocity drift compensation to the filtered acceleration data; applying at the EMS, a second high pass filter; determining at the EMS, a displacement of the filtered acceleration data; applying at the EMS, a drift compensation to the filtered acceleration data; applying at the EMS, a zero band point algorithm to the displacement filtered acceleration data; determining at the EMS, one or more of: a range, a tempo, a work done, a power, and a calories consumed based on the applied zero band point algorithm.

A service that provides virtual fitness training and tracking services to a user. These services are available to user via a website and/or an application on a personal device like a smart phone or a wearable.

This brief summary has been provided so that the nature of this disclosure may be understood quickly. A more complete understanding of the disclosure can be obtained by reference to the following detailed description of the various aspects thereof in connection with the attached drawings.

BRIEF DESCRIPTION OF THE DRAWINGS

The components in the figures are not necessarily to scale, emphasis instead being placed upon illustrating the principals of the invention. Like reference numerals designate corresponding parts throughout the different views. Embodiments are illustrated by way of example and not limitation in the figures of the accompanying drawings, in which:

FIG. 3B-$i$ shows a flowchart of training plan assignment to a user according to one embodiment;

FIG. 3B-$ii$ shows a flowchart of creation of dynamic and optimal training plans according to one embodiment;

FIG. 4B-$i$ shows a top cross-sectional view of a Weight Sensor Pin;

FIG. 4B-$ii$ shows a cross-sectional view of forces on a Weight Sensor Pin;

FIG. 4B-$iii$ shows a cross-sectional view of forces under a typical loading scenario for the Weight Sensor Pin;

FIG. 4F-$i$ shows a schematic of Active Sensor Link Type F showing one side of a barbell having an electronics box loaded on one end;

FIG. 4F-$ii$ shows a schematic of Active Sensor Link Type F showing a cross-sectional view of a barbell having a strain gauge;

FIG. 4G-$i$ shows a top cross-sectional view of a weight sensor pin with a barcode reader and a weight with a barcode;

FIG. 4G-$ii$ shows a front view of Type-G Active Sensor Link with Weight Sensor pin with a barcode reader and weights with a barcode;

FIG. 4G-$iii$ shows a photo captured by a barcode reader camera;

FIG. 4G-$iv$ shows a photo captured by a barcode reader camera when a pin is rotated at an angle and a rotation-corrected barcode photo;

FIG. 4G-$v$ shows a photo of a weight plate number captured by the camera;

FIG. 4G-$vi$ shows a photo of the weight plate number of FIG. 4G-$v$ when a pin is rotated at an angle and a rotation-corrected weight plate label photo;

DETAILED DESCRIPTION

Figure 1:
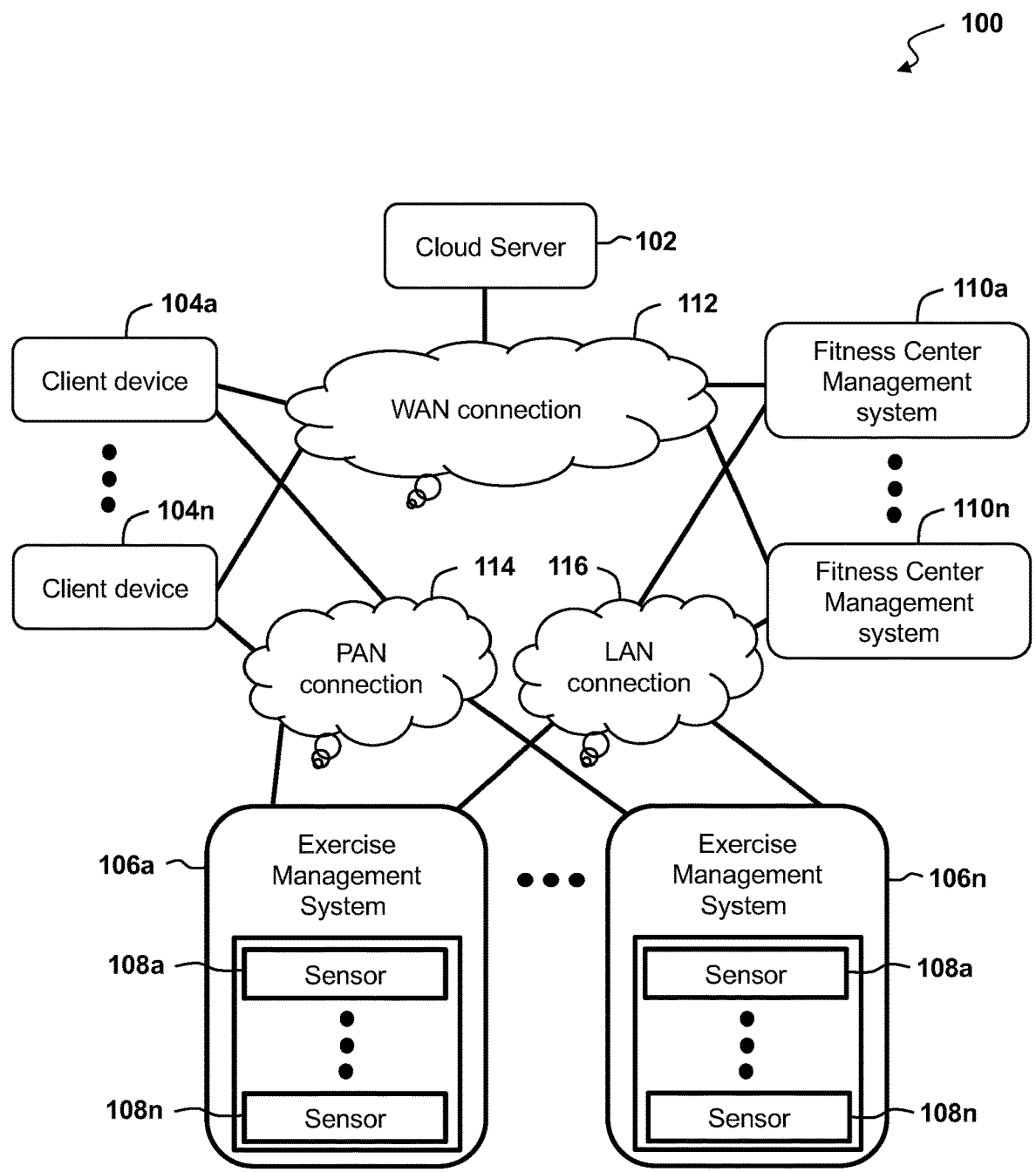
FIG. 1 shows an exemplary system and its various components disclosed herein.

The following description is made for the purpose of illustrating the general principles of the embodiments disclosed herein and is not meant to limit the concepts disclosed herein. Further, particular features described herein can be used in combination with other described features in each of the various possible combinations and permutations. Unless otherwise specifically defined herein, all terms are to be given their broadest possible interpretation including meanings implied from the description as well as meanings understood by those skilled in the art and/or as defined in dictionaries, treatises, etc.

Health and fitness are becoming increasingly important to people, however, selecting and tracking a fitness program may be difficult and/or impractical for a user to accomplish in a fitness environment. Embodiments of a method and system disclosed herein can be used to improve personal fitness. One embodiment disclosed herein includes a virtual trainer, an accurate tracker, and social encouragement for a user selected fitness training program. This improves the user experience of exercise machines (e.g., treadmills, cross trainer, weight machines and free weights) and other exercises.

One embodiment comprises system and method disclosed herein including an exercise management system allowing users to create their credentials, select the fitness center location and client device. A user may do this initial setup at their home or at the fitness center with help from a trainer. After this initial setup, the user may be notified of their exercise session at the fitness center or at home and the user follows the steps as outlined. The user may share this exercise information with their friends or on a social network to increase accountability, receive encouragement, and/or encourage others. This information from the exercise management system is also shared with a cloud server and the user can look at their exercise history at a web site or on an active client device application. The user may also share this information with a trainer whose training plan they have selected for further guidance and advice.

The system and method disclosed herein allows a user to register for the system, select a fitness center equipped with the system, and select a training plan based on the selected fitness center. The user may then go to the fitness center and sync their user device with an Exercise Management System (EMS) attached to an exercise equipment. The EMS may retrieve the user's selected training plan, guide the user through the exercise on the exercise equipment, and track one or more aspects of the workout via one or more sensors connected to the EMS. The EMS may then update a cloud server with the results of the workout according to the selected training plan, and these results may be viewed on the user device. Accordingly, the system allows a user to track their workouts in a fitness setting where accurate and consistent tracking may be otherwise impossible and/or impractical. This allows a user using the user device to keep track of their fitness via the selected training plan. The user may also encourage and/or be encouraged by one or more friends via a social networking link to the users workouts. The disclosed system provides accuracy, consistency, and accountability to the user of the user device to help the user achieve his or her fitness goals.

For clarity, certain terminology used in the description herein is detailed below by way of example.

Component or Module: The terms "component," "module" and the like as used herein are intended to refer to computer-related entities, such as software-executing on processors, hardware, firmware, and/or combinations thereof. For example, a component may be, but is not limited to being, a process running on a processor, a processor, an object, an executable, a thread of execution, a program, and/or a computer.

By way of illustration, both an application running on a server and the server can be a component. One or more components may reside within a process and/or thread of execution, and a component may be localized on one computer and/or distributed between two or more computers. Also, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal).

Computer executable components can be stored, for example, on non-transitory computer readable media including, but not limited to, an ASIC (application specific integrated circuit), CD (compact disc), DVD (digital video disk), ROM (read only memory), floppy disk, hard disk, EEPROM (electrically erasable programmable read only memory), memory stick or any other storage device, in accordance with the embodiments discloses herein.

Cloud Computing: The system and techniques described above are applicable and useful in a cloud computing environment. Cloud computing means computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. The term "cloud" is intended to refer to any network (including the Internet) for providing computers as a shared resource.

Typical cloud computing providers deliver common business applications online which are accessed from another web service or software like a web browser, while the software and data are stored remotely on servers. The cloud computing architecture uses a layered approach for providing application services. A first layer is an application layer that is executed at client computers. In this example, the application allows a client to access storage via a cloud.

After the application layer, is a cloud platform and cloud infrastructure, followed by a "server" layer that includes hardware and computer software designed for cloud specific services. The replication server and the storage systems described above can be a part of the server layer for providing storage services. Details regarding these layers are not germane to the inventive aspects.

Internet: The Internet connects millions of computers worldwide through well-known protocols, for example, Transmission Control Protocol (TCP)/Internet Protocol (IP), into a vast network. Information on the Internet is stored worldwide as computer files, mostly written in the Hypertext Mark Up Language ("HTML"). Other markup languages (e.g., Extensible Markup Language ("XML"), JSON (JavaScript Object Notation)) as published by W3C and ECMA Consortium may also be used. The collection of all such publicly available computer files is known as the World Wide Web ("WWW"). The WWW is a multimedia-enabled hypertext system used for navigating the Internet and is made up of many web pages with images and text and video files, which can be displayed on a computer monitor. Each web page can have connections to other pages, which may be located on any computer connected to the Internet.

Web Browser: A typical Internet user uses a client program called a "Web Browser" to connect to the Internet. A user can connect to the Internet via a proprietary network. The web browser may run on any computer connected to the Internet. Currently, various browsers are available of which two prominent browsers are Google Chrome and Microsoft Internet Explorer (without derogation of any trademark rights). The Web Browser receives and sends requests to a web server and acquires information from the WWW. A web server is a program that, upon receipt of a request, sends the requested data to the requesting user. A standard naming convention known as Uniform Resource Locator ("URL") has been adopted to represent hypermedia links and links to network services. Most files or services can be represented with a URL.

URLs enable Web Browsers to go directly to any file held on any WWW server. Information from the WWW is accessed using well-known protocols, including the Hypertext Transport Protocol ("HTTP"), the Wide Area Information Service ("WAIS") and the File Transport Protocol ("FTP"), over TCP/IP protocol. The transfer format for standard WWW pages is Hypertext Transfer Protocol (HTTP).

Sensor: comprises a device that detects events or changes in quantities and provides a corresponding output, generally as an electrical or optical signal; for example, a thermocouple converts temperature to an output voltage. Technological progress allows more and more sensors to be manufactured on a microscopic scale as using MEMS technology.

Sensor communication protocols: Sensors can communicate with processors using standard protocols such as I2C (Inter-Integrated Circuit), SPI (Serial Peripheral Interface) or UART (Universal asynchronous receiver/transmitter).

The processor can send commands for setting up and measuring environmental inputs like temperature, acceleration, cable tension, etc. and the sensor responds with the results of these measurements.

Network Bridge: comprises network equipment and software needed to create an aggregate network from either two or more communication networks, or two or more network segments. A network bridge may connect a WAN to a LAN or PAN which may be wired or wireless.

Communication standards: Devices may be wired or wireless and use standards based communication protocols like Ethernet Wi-Fi, Bluetooth, Bluetooth low energy (BLE), NFC, RFID, ZigBee etc. These Wide Area Network (WAN), Local Area Network (LAN) and Personal Area Network (PAN) standards are developed by various standards bodies like IEEE, Bluetooth Special Interest Group, NFC Forum etc.

Load cell or load pin: comprises a transducer that is used to create an electrical signal whose magnitude is directly proportional to the force being measured. The various types of load cells include strain gauge, capacitive, and piezoelectric load cells.

In one embodiment, Optical Character Recognition, Pattern Recognition and Machine Learning technologies may be used to process a photo captured by a camera to recognize an alpha numeric character or symbol (e.g., a barcode).

Exercise machine: comprises any machine used for physical exercise. These range from simple free weights like dumbbells and barbells to weight machines that have weights hanging from a cable and Cardio workout machines like Treadmills, Elliptical, and Cross trainers.

Exercise: comprises any activity requiring physical effort, carried out specially to sustain or improve health and fitness. They include activities like Leg press, Curl, Bench press, Squat, Extensions, and cardio activities that need Exercise equipment. They may also include physical activities like floor exercises, bars, and benches.

Referring now to the drawings, example embodiments are described below. FIG. 1 shows an example implementation of a system 100, according to one embodiment. The system 100 comprises a cloud server 102, a plurality of client devices 104a, . . . , 104n, a plurality of exercise management systems (EMS) 106a, . . . , 106n and a plurality of fitness center management systems (FCMS) 110a, . . . , 110n.

The cloud server 102 may be located in a data center and it may include one or more processors, memory (e.g., RAM, disk) input and output devices like keyboard and monitor, and network connection to the WAN connection 112. The cloud server 102 may connect to one or more of the FCMS 110a, . . . , 110n and client devices 104a, . . . , 104n using the WAN connection 112.

The client devices 104a, . . . , 104n may comprise fully featured computers with processors, memory, storage, networking, and sensors. Smart phones and wearable devices may have several components used in a client device and the user may carry the client device to a fitness center. The client device may connect with one or more of the EMS 106a, . . . , 106n using the PAN connection 114 as described in the communication standards above.

An EMS may comprise computers with processors, memory, storage, networking, and sensors. In a fitness center, the EMS may be mounted on exercise machines as described in the Exercise Machine section above. An EMS may have a plurality of sensors 108a, . . . , 108n. Example sensors 108a, . . . , 108n are described in the sensor and sensor communication above. The EMS 106a, . . . , 106n may be connected to the FCMS 110a, . . . , 110n using the LAN connection 116 as described in the communication standards above.

Each FCMS may be installed in a fitness center location, and may comprise a fully featured computer or server like the cloud server 102.

Figure 1A:
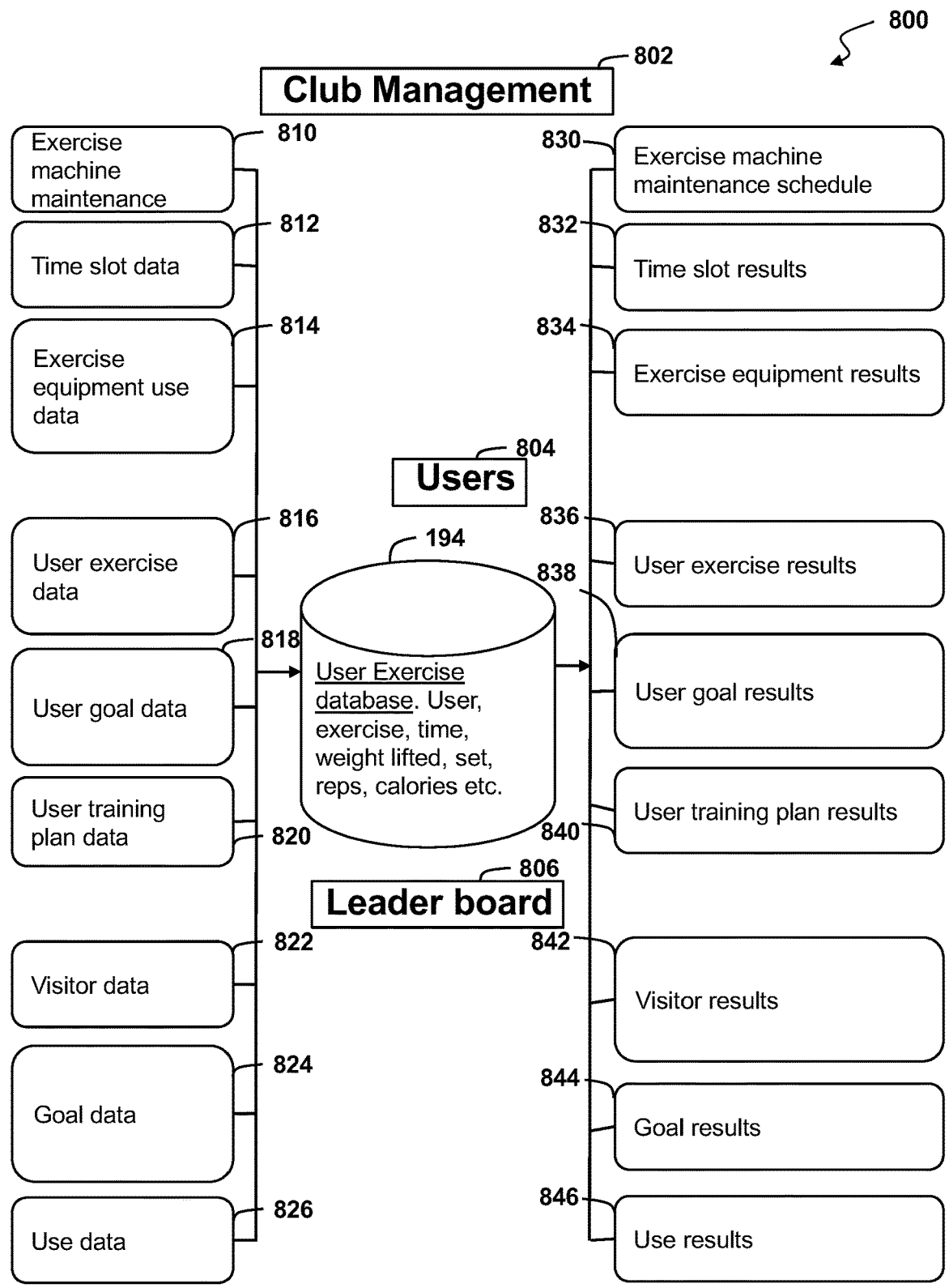
FIG. 1A shows an example of the processing on the cloud server according to one embodiment.

FIG. 1A shows an exemplary embodiment of the processing 800 done on the cloud server 102 (e.g., FIG. 1) This processing is for benefit of three audiences: a club management module 802, a user module 804 and a leader boards module 806. All of this cloud server processing is done on the user exercise database 194 that contains the name of the user, the exercise done, the time of the exercise, the weight lifted, the number of sets, the repetitions, the tempo, the work done, the maximum power, the calories burned, etc. Questions that are of interest to specific audiences may be asked by the system administrator as database queries and the answers of these questions may be shared with the appropriate audience.

In one embodiment, a fitness club manager, via the club management module 802, may be interested in knowing answers to questions regarding exercise machine maintenance (step 810) (e.g., 'Which machines need preventive maintenance?'); time slot data (step 812) (e.g., 'When do most users visit the fitness center?'), or exercise equipment use data (step 814) (e.g., 'Which fitness equipment is most popular with users?'). The responses to these queries by the club management module 802 may include, respectively, an exercise machine maintenance schedule (step 830) (e.g., 'Weight machine leg press has been used for 2,150 hours and needs preventative maintenance'); time slot results (step 832) (e.g., 'Tuesday between 5:00 and 8:00 PM is the most popular time'); exercise equipment results (step 834) (e.g., 'Bench press is the most popular exercise machine with men and leg adductor with women'). These responses may be shared with the fitness club management. These types of questions may be asked as needed or in response to some event which might be end of each week or month.

In one embodiment, a user, via the user module 804, may be interested in knowing user exercise data (step 816) (e.g., 'Did I burn more calories this month?'); user goal data (step 818) (e.g., 'How close I am to achieving my goal?'); and/or user training plan data (step 820) (e.g., 'Am I following my training plan?') The user, via the user module 804, may get respective responses such as user exercise results (step 836) (e.g., 'This week you burned 2457 kcal, compared to last week when you burned 1975 kcal. Excellent !!'); user goal results (step 838) (e.g., 'You are at 85% or your goal, it is expected that you will reach your goal in 2 weeks'); and/or user training plan results (step 840) (e.g., 'Yes you are following your training plan but drop weights 0.3 sec slower').

In one embodiment, tidbits might be of interest to users and accessed on a leader board, via the leader board module 806. The information of interest might be visitor data (step 822) (e.g., 'Who visits the club most often'); goal data (step 824) (e.g., 'Which trainer helped most clients achieve their goal?'); and/or use data (step 826) (e.g., 'Who lifted the most weight today?'). The responses to these questions may be respectively presented via the leader board module 806 as visitor results (step 842) (e.g., 'Dan and Jessica have been coming to the club 6 days a week for over two months. Great job!!'); goal results (step 844) (e.g., 'Travis helped 85% of his clients reach their goal'); and/or use results (step 846) (e.g., 'Rob lifted a total of 15,750 lbs. today, way to go!!').

Figure 1B:
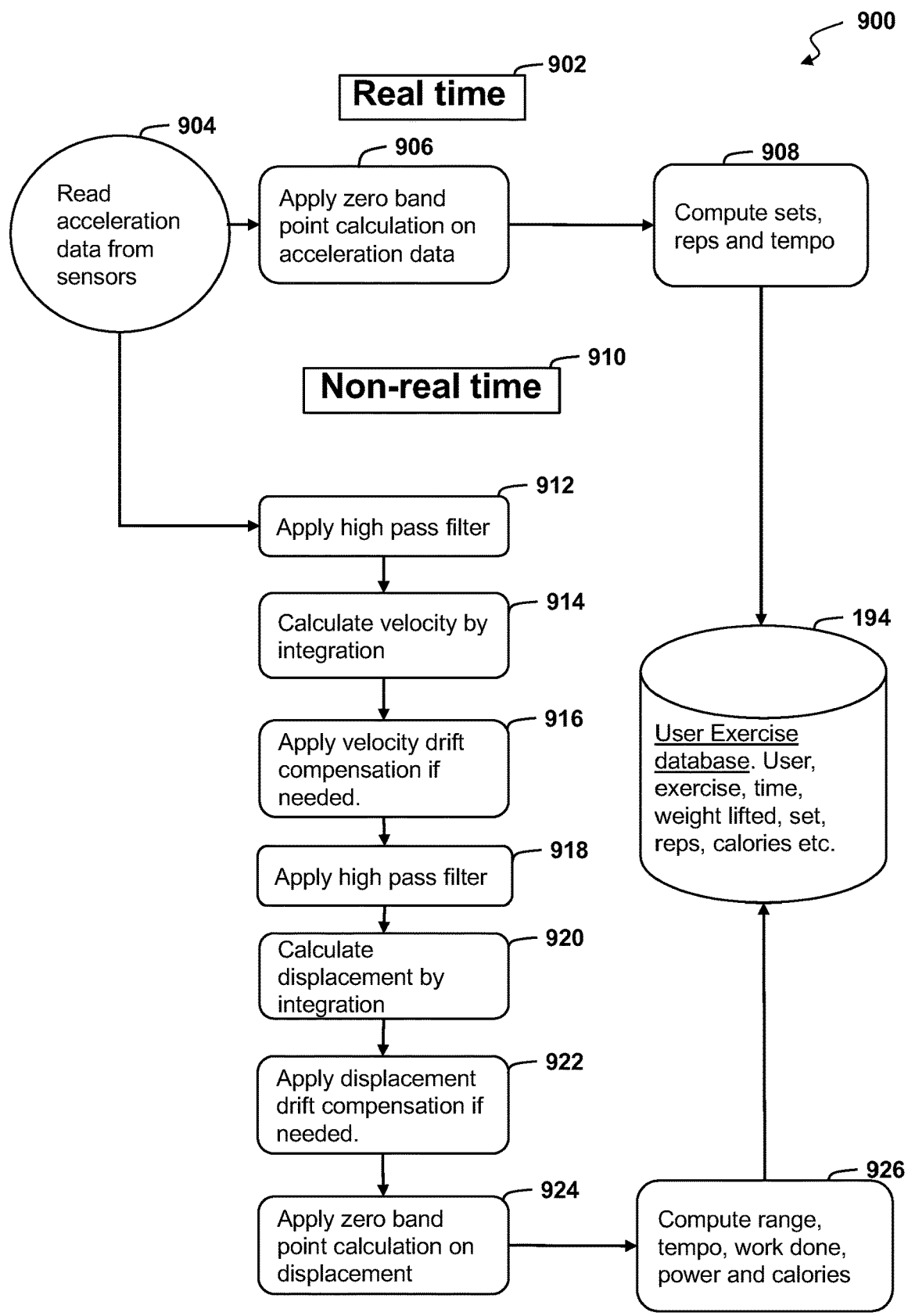
FIG. 1B shows an example of the processing done on the Exercise Management System according to one embodiment.

FIG. 1B shows an exemplary embodiment 900 of the processing done on the exercise management system (106a, ..., 106n) (e.g., FIG. 1). There are two types of processing done, one is completed in a real time processing module 902 and the other may take longer to compute as the data may be filtered to remove drift in a non-real time processing module 910.

In one embodiment, the acceleration values are read from the sensors (step 904) and a zero band point algorithm is applied to the acceleration data (step 906) to compute the workout information such as number of sets, repetitions, tempo, etc. (step 908) and this information is stored in the user exercise database 194.

In one embodiment, the non-real time processing module 910 may compute other information of interest. First, a high pass filter (step 912) with appropriate coefficients to eliminate a DC component of the waveform is applied to the raw acceleration data. The velocity is then calculated by integrating the filtered acceleration values (step 914). If needed, a velocity drift compensation algorithm (step 916) is applied. Then, a high pass filter (step 918) may once again be applied and displacement is computed by integrating the velocity (step 920) and drift compensation (step 922) is applied if needed. On the displacement data, the zero band point algorithm (step 924) is applied to compute range, tempo, work done, power, and/or calories consumed (step 926) and these results are stored in the user exercise database 194.

Figure 2A:
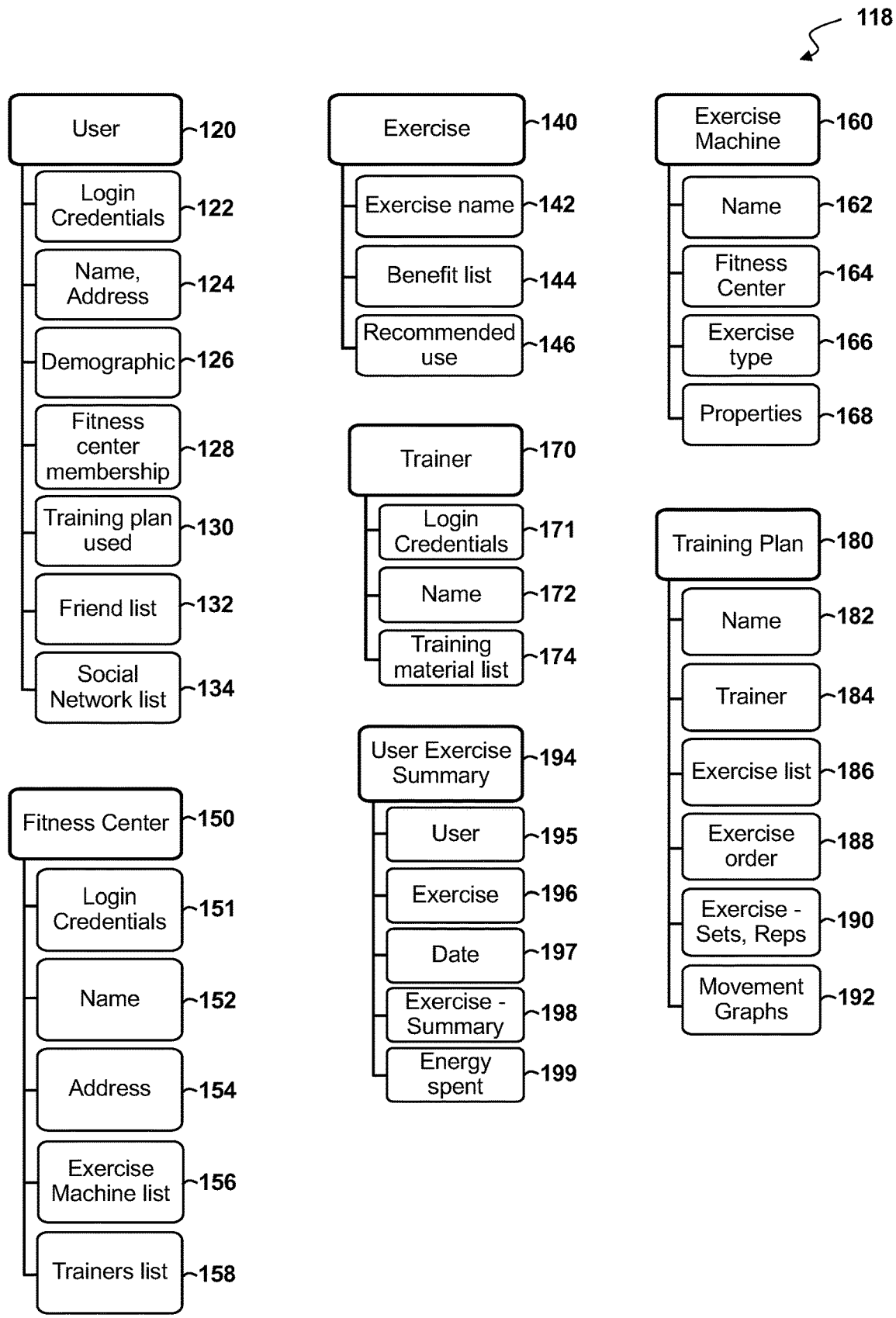
FIG. 2A shows an example of the databases on the Cloud server according to one embodiment.

FIG. 2A shows an exemplary embodiment of a database 118 in the cloud server 102 (e.g., FIG. 1). A user database 120 stores information including user login credentials 122, name, address 124 and other fitness related demographic 126 and user anatomical information. A fitness center 128 may comprise a public, private, or home gym and a training plan 130 used may comprise one created by a fitness trainer or one customized by the fitness center trainer. A friend list 132 may comprise a contact list of persons who share similar objectives and to whom the user offers and/or receives encouragement. A Social Network list 134 may include the user's credentials in well-known social networks, which may be used for posting achievements. In one embodiment, a User may fill in the information needed for the user database 120 using a web browser as described in the web browser section on a computer or smart phone connected to the Internet as described in the Internet section above.

An exercise database 140 may include an exercise name 142 of an exercise as described in the exercise section above, a list of benefits 144 of performing the exercise and its recommended use 146. In one embodiment, this information may be filled by the company managing the system using the web browser and Internet above.

A fitness center database 150 has a name 152 and an address 154 of the fitness center and a list of exercise machines 156 that are in the fitness center. The database 150 may also store login credentials 151. The list of exercise machines 156 may include treadmills, cross trainers, weight machines, free weights, and other exercise equipment like exercise room, sauna, etc. that have an EMS installed on them. The fitness center database 150 may also include a list of trainers 158 available at the fitness center. In one embodiment, this information may be filled by the fitness center using the web browser and Internet.

An exercise machine database 160 includes a list of all exercise machines with EMS installed on them. The exercise machine database 160 includes an exercise machine name 162, a Fitness center it is located in 164, a type of Exercise 166 it is used for and any corresponding properties 168 like a number of different weights, seat height, leg length etc. available on the exercise machine 160. In one embodiment, this information may be filled by the company managing the system using the web browser and Internet.

A trainer database 170 has a list of trainer names 172 who are participating in the system. The database 170 may also store login credentials 171. The trainers may be well-known trainers or may be trainers at the local fitness center. They may also provide links to a list of their training material 174. In one embodiment, this information may be filled by the trainers using the web browser and Internet.

A training plan database 180 has training plans developed by the trainer 170 that a user in the user database 120 may follow. The database 180 has a training plan name 182, a name of the trainer 184 who developed it, the list of exercises 186 that are part of the training plan, the order 188 in which the exercises should be performed and relevant details like number of sets, repetitions, lifting speed (or tempo), etc. 190 that should be performed. The training plan may be assigned by a trainer to a user and it may only be available to the user while they are paying for trainer services. This training plan may vary on different days of the week or month to allow for training different parts of the body with different intensities. To create the training plan in the training plan database 180, a trainer in the trainer database 170 may use the system to track and record themselves while they exercise. They can create very detailed movement graphs 192 of the lifted weights. In one embodiment, this information may be filled by the trainers using the web browser and Internet.

A user exercise summary database 194 has the details of the exercises performed by the users in the user database 120. The information may include a user name 195, an exercise 196 that they have done, and a date 197 and a time when they performed the exercise. The database 194 may also have an exercise summary 198 that has information such as a weight lifted, a number of sets and repetitions, a lifting speed, etc. along with an amount of energy, maximum power, or calories spent 199.

Figure 2B:
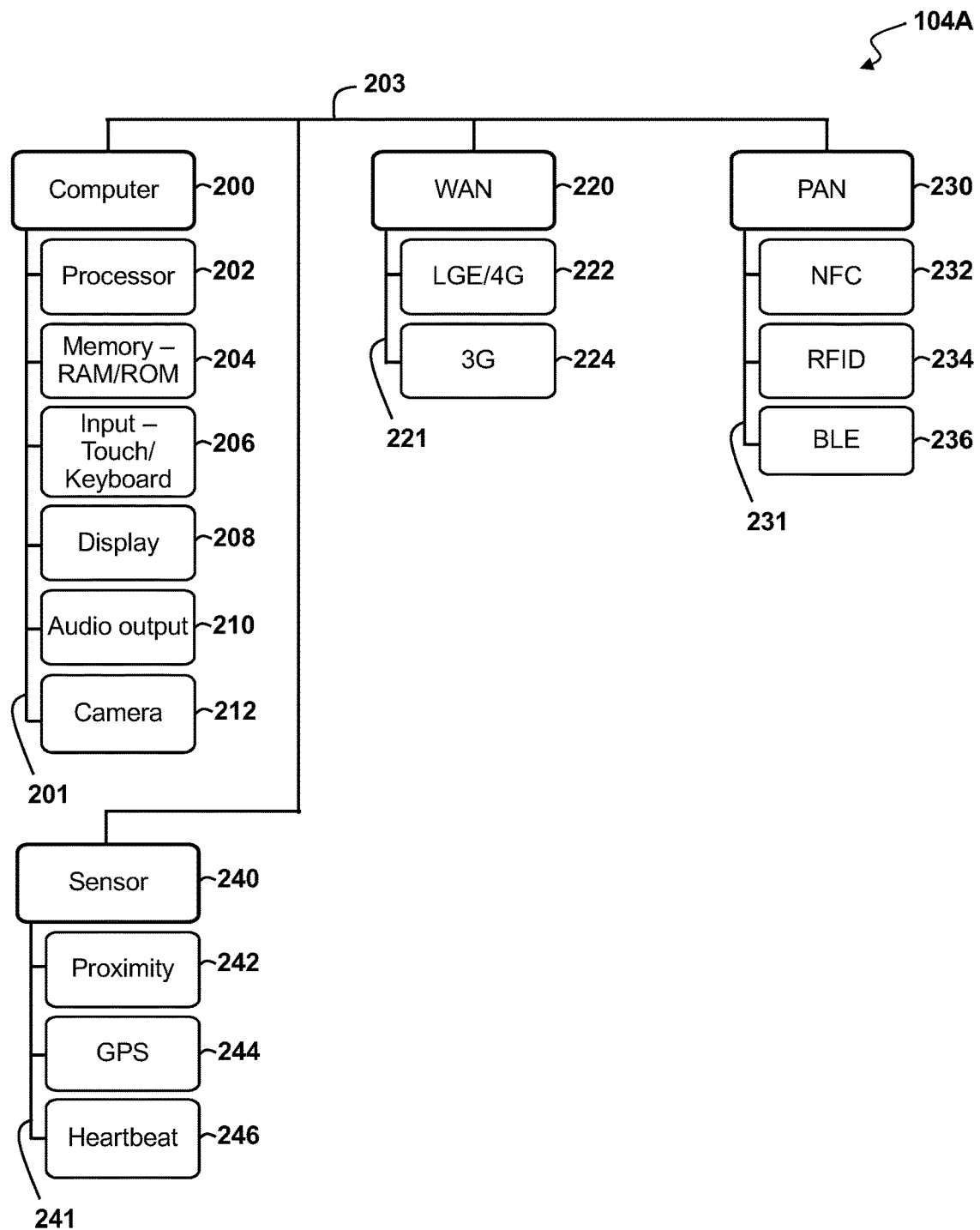
FIG. 2B shows an example of one embodiment of the Client device referred to as Active client device.

FIG. 2B shows one embodiment of the client device referred to as the active client device 104A in more detail. Many of its components are found in today's feature phones or smart phones. Increasingly, some of these components are also found on wearables and smart watches. In one embodiment, the active client device 104A may be a smart phone, feature phone, and/or a wearable device. A computer 200 having a communication connection 201 (e.g., a data/control bus) has a processor 202, memory 204, and may have an input 206 (e.g., a touch display or keyboard), a display 208, an audio output 210, and/or a camera 212. A WAN module 220 having a communication connection 221 (e.g., a data/control bus) for establishing and/or joining a WAN may have one or more of a LTE/4G 222, a 3G 224, or other wireless WAN connectivity. This component may be used to connect with the Cloud server 102 (e.g., FIG. 1). A PAN module 230 having a communication connection 231 (e.g., a data/control bus) for establishing and/or joining a PAN may have one or more of an NFC 232, an RFID 234, a BLE 236, or other PAN connectivity including Wi-Fi. The PAN 230 component may be used to connect with a PAN component 310 (e.g., FIG. 2D) of the EMS 106a, ..., 106n (e.g., FIG. 1). A sensor 240 having a communication connection 241 (e.g., a data/control bus) may be one or more of a proximity 242, a GPS 244, and a heartbeat 246 and they may connect with the EMS to share and augment sensor data. A communication connection 203 (e.g., a data/control bus) may connect the computer 200, WAN 220, PAN 230, and/or sensor 240.

Figure 2C:
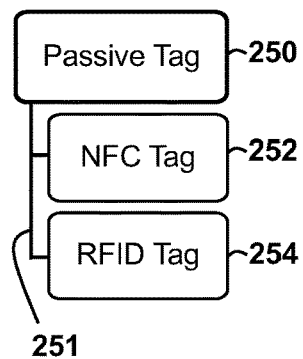
FIG. 2C shows an example of another embodiment of the Client device referred to as passive client device.

FIG. 2C shows another embodiment of the client device referred to as the passive client device 104B. It may have a passive tag 250 that may be one of a NFC Tag 252, a RFID Tag 254, and/or other passive connectivity, and this may be used to connect with a PAN 310 (e.g., FIG. 2D) component of the EMS 106a, . . . , 106n (e.g., FIG. 1). An example of the passive client device 104B may be NFC or RFID tags.

Figure 2D:
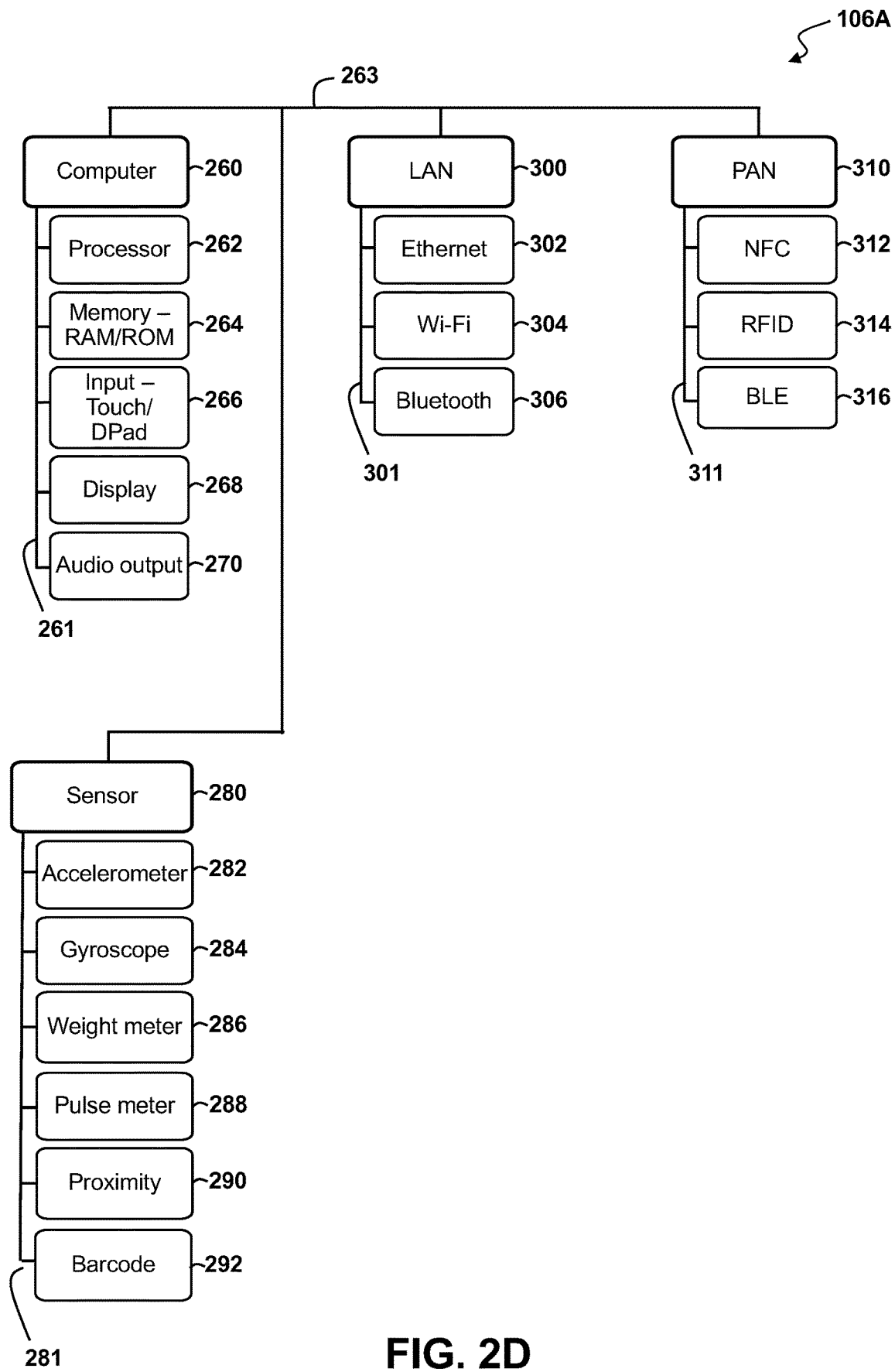
FIG. 2D shows an example of one embodiment of an Exercise Management System (EMS) referred to as Active Sensor Link.

FIG. 2D shows one embodiment of the EMS referred to as the active sensor link 106A in more detail. A computer 260 having a communication connection 261 (e.g., a data/control bus) has a processor 262, a memory 264, and may have an input device 266 (e.g., a touch or a D-pad), a display 268, and/or an audio output 270. There may be one or more sensors 280 having a communication connection 281 (e.g., a data/control bus) for example, an accelerometer 282, a gyroscope 284, a weight and/or tension meter 286, a pulse meter 288, and/or a proximity 290, and/or a barcode reader or camera 292. These sensors 280 connect to the computer 260 using sensor communication protocols as described in the sensor protocol section above. The active sensor link 106A may be mounted on fitness equipment like treadmills, cross trainers, weight machines, free weights (e.g., dumbbell, barbell) where the sensors 280 may be used to measure exercise information like weight lifted, number of sets, number of repetitions, exercise duration, etc. A LAN module 300 having a communication connection 301 (e.g., a data/control bus) for establishing and/or joining a LAN might use one or more of an Ethernet 302, a Wi-Fi 304 or a Bluetooth 306 technologies. The EMS 106a, . . . , 106n (e.g., FIG. 1) may be connected to the FCMS 110a, . . . , 110n (e.g., FIG. 1) using the LAN 300 component. A PAN module 310 having a communication connection 311 (e.g., a data/control bus) for establishing and/or joining a PAN may use technologies like an NFC 312, an RFID 314, and/or a BLE 316. The client device 104a, . . . , 104n (e.g., FIG. 1) may connect to the EMS 106a, . . . , 106n using the PAN 310 component. The EMS may include onboard battery or other power source for providing electrical power to the components of the EMS module. A communication connection 263 (e.g., a data/control bus) may connect the computer 260, LAN 300, PAN 310, and/or sensor 280.

Figure 2E:
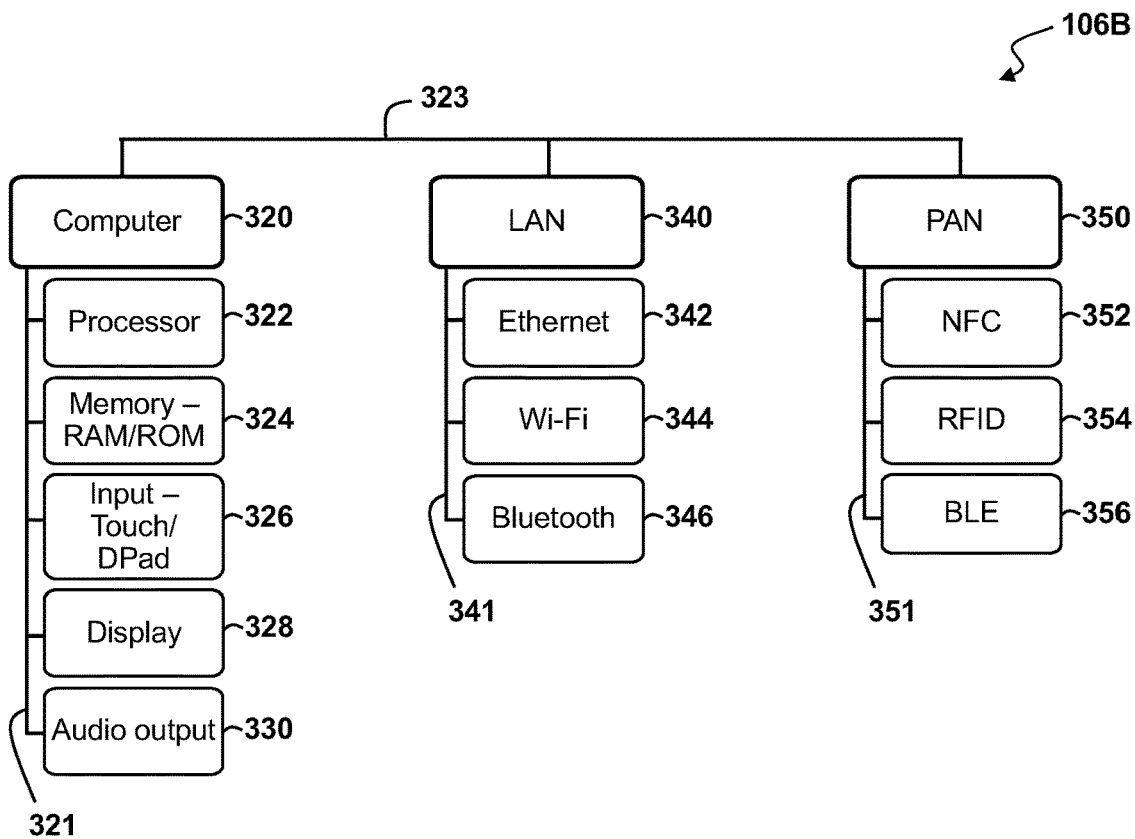
FIG. 2E shows an example of another embodiment of the EMS referred to as Passive Link.

FIG. 2E shows another embodiment of the EMS referred to as passive link 106B in more detail. The passive link 106B is similar to the active sensor link 106A (e.g., FIG. 2D) except that it does not have the sensors. A computer 320 having a communication connection 321 (e.g., a data/control bus) has a processor 322, a memory 324, and may have an input device 326, a display 238, and/or an audio output 330. A LAN module 340 having a communication connection 341 (e.g., a data/control bus) for establishing and/or joining a LAN may use one or more of an Ethernet 342, a Wi-Fi 344 or a Bluetooth 346 technologies. The EMS 106a, . . . , 106n (e.g., FIG. 1) may be connected to the FCMS 110a, . . . , 110n (e.g., FIG. 1) using the LAN 340 component. A PAN module 350 having a communication connection 351 (e.g., a data/control bus) for joining and/or establishing a PAN may use technologies like an NFC 352, an RFID 354, and/or a BLE 356. The client device 104a, . . . , 104n (e.g., FIG. 1) may connect to the EMS 106a, . . . , 106n (e.g., FIG. 1) using the PAN 350 component. The passive link 106B may be mounted on exercise equipment like weight benches, pull up bars, aerobic exercise rooms, etc. that do not need sensors and they may be used to measure exercise duration. Passive link 106B may also be mounted on existing fitness equipment like treadmills and cross trainers where exercise data may not be accessible. A communication connection 323 (e.g., a data/control bus) may connect the computer 300, LAN 340, and/or PAN 350.

Figure 2F:
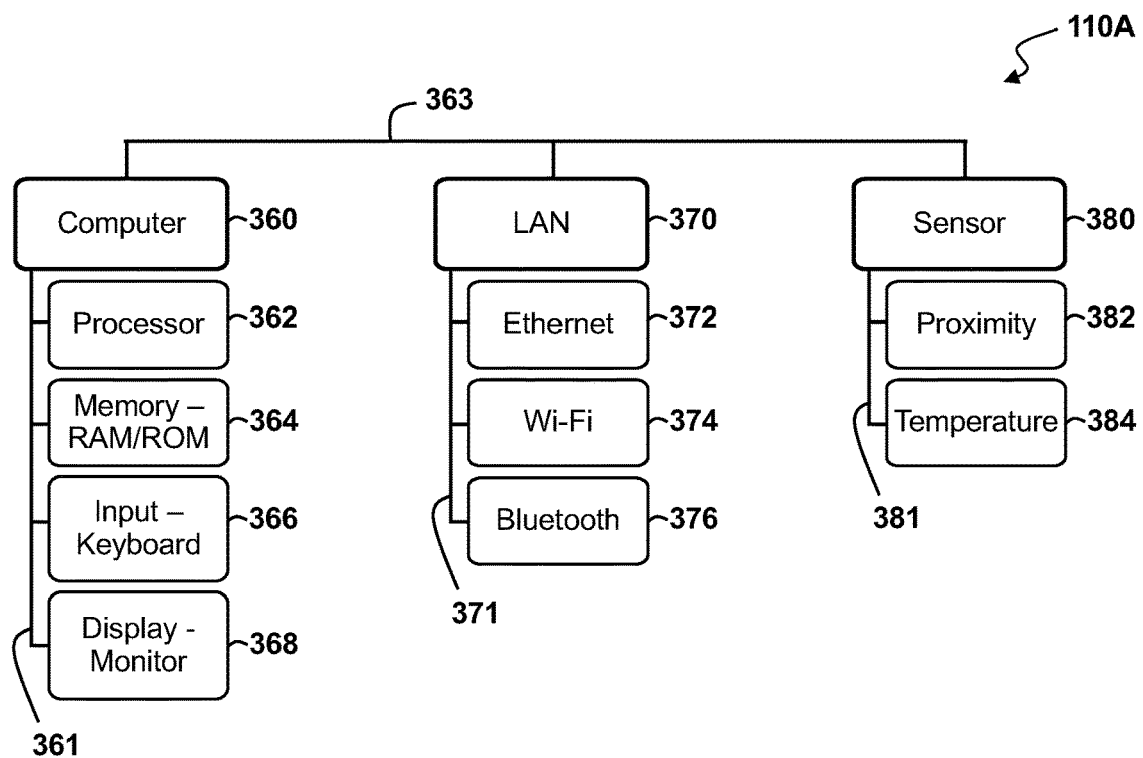
FIG. 2F shows an example of one embodiment of the fitness center management systems (FCMS) referred to as Fully featured FCMS.

FIG. 2F shows one embodiment of the FCMS in more detail. A Fully featured FCMS 110A may have a computer 360 having a communication connection 361 (e.g., a data/control bus) having a processor 362, memory 364, and may have an input device 366, and/or display 368. A LAN module 370 having a communication connection 371 (e.g., a data/control bus) for establishing and/or joining a LAN may have one or more of an Ethernet 372, a Wi-Fi 374, and/or a Bluetooth 376. A LAN 370 may be used to connect with the client device 104a, . . . , 104n (e.g., FIG. 1). A sensor 380 having a communication connection 381 (e.g., a data/control bus) may have one or more of a proximity 382 or a temperature 384 sensors. The fully featured FCMS 110A may be connected to the cloud server using the Internet backbone. A communication connection 363 (e.g., a data/control bus) may connect the computer 360, LAN 370, and/or sensor 380.

Figure 2G:
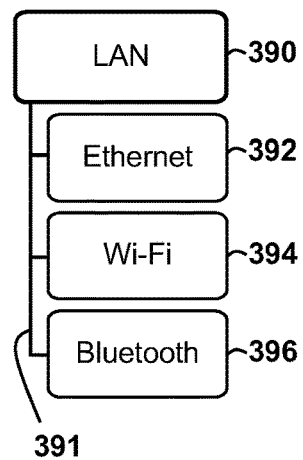
FIG. 2G shows an example of another embodiment of the FCMS referred to as Simple FCMS.

FIG. 2G shows another embodiment of the FCMS in more detail. A simple FCMS 110B may have functionality that may be found on Wi-Fi access points. A LAN module 390 having a communication connection 391 (e.g., a data/control bus) for establishing and/or joining a LAN may have one or more of an Ethernet 392, a Wi-Fi 394, or a Bluetooth 396. The LAN 370 may be used to connect with the client device 104a, . . . , 104n (e.g., FIG. 1). The simple FCMS 110B may be connected to the cloud server using the Internet backbone.

Figure 2H:
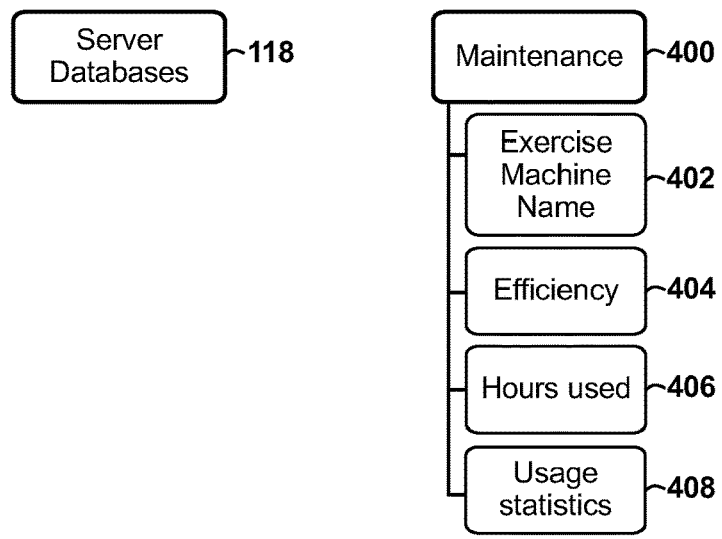
FIG. 2H shows an example of databases on a Fully featured FCMS according to one embodiment.

FIG. 2H shows databases 398 that may be present on the Fully featured FCMS 110A (e.g., FIG. 2F). These databases may have all or parts of the cloud server databases 118 and may sync with the cloud server using the Internet on a regular basis. In one embodiment, it may have the information related to the particular fitness center where it is installed. It may also have a maintenance database 400 for exercise machines in this fitness center. This database may have an exercise machine name 402 and a current efficiency 404 of the machine, which may be used as a proxy for machine maintenance level. It may also have a number of hours the exercise machine has been used 406. It may also be used to monitor facility usage by keeping track of when exercise machines are used most often 408. Exercise machine maintenance may be scheduled when an efficiency 404 drops below a certain threshold and/or the number of hours the machine has been used 406 exceeds manufacturer's recommendation.

Figure 3A:
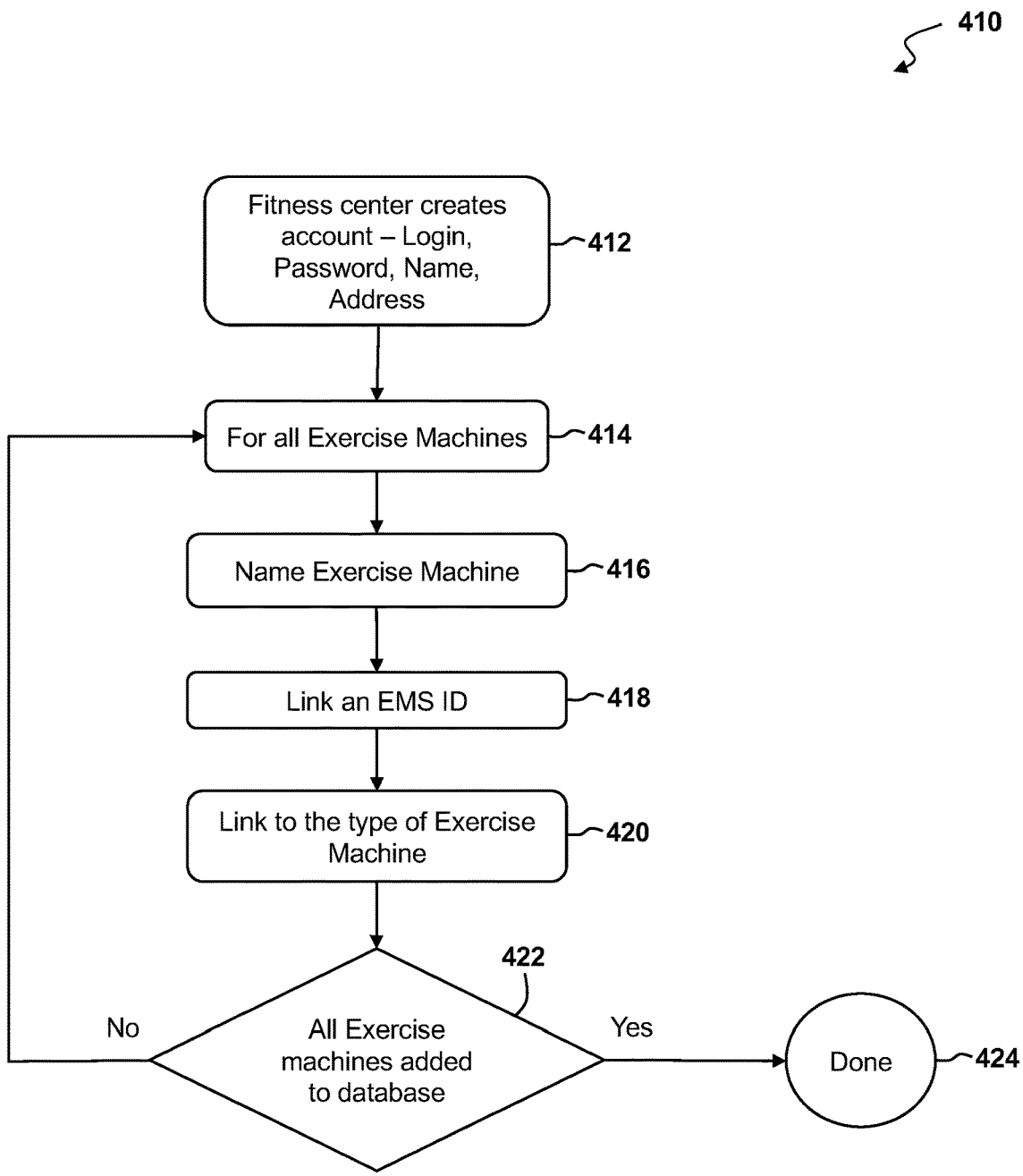
FIG. 3A shows a flowchart of the initial setup for the system at a Fitness center according to one embodiment.

FIG. 3A is an example of the initial setup for a Fitness center to use the system 410. This is accomplished by adding the fitness center information to the fitness center database 150 (e.g., FIG. 2A) in the cloud server 102 (e.g., FIG. 1). In one embodiment, the fitness center accesses a fitness center page on the system website and creates an account credentials including login, password, and fitness center name and address (step 412).

For all the exercise machines on which the Fitness center desires to mount the EMS (step 414), a fitness center user creates a name for the Exercise machine (step 416) and then links it to a unique EMS Identifier (step 418) of the EMS that they will mount on the exercise machine. The fitness center user then links the exercise machine to the exercise or exercises that may be done on this machine (step 420). This process is completed (step 424) when all the exercise machines are added to a fitness center database (step 422).

Figure 3B:
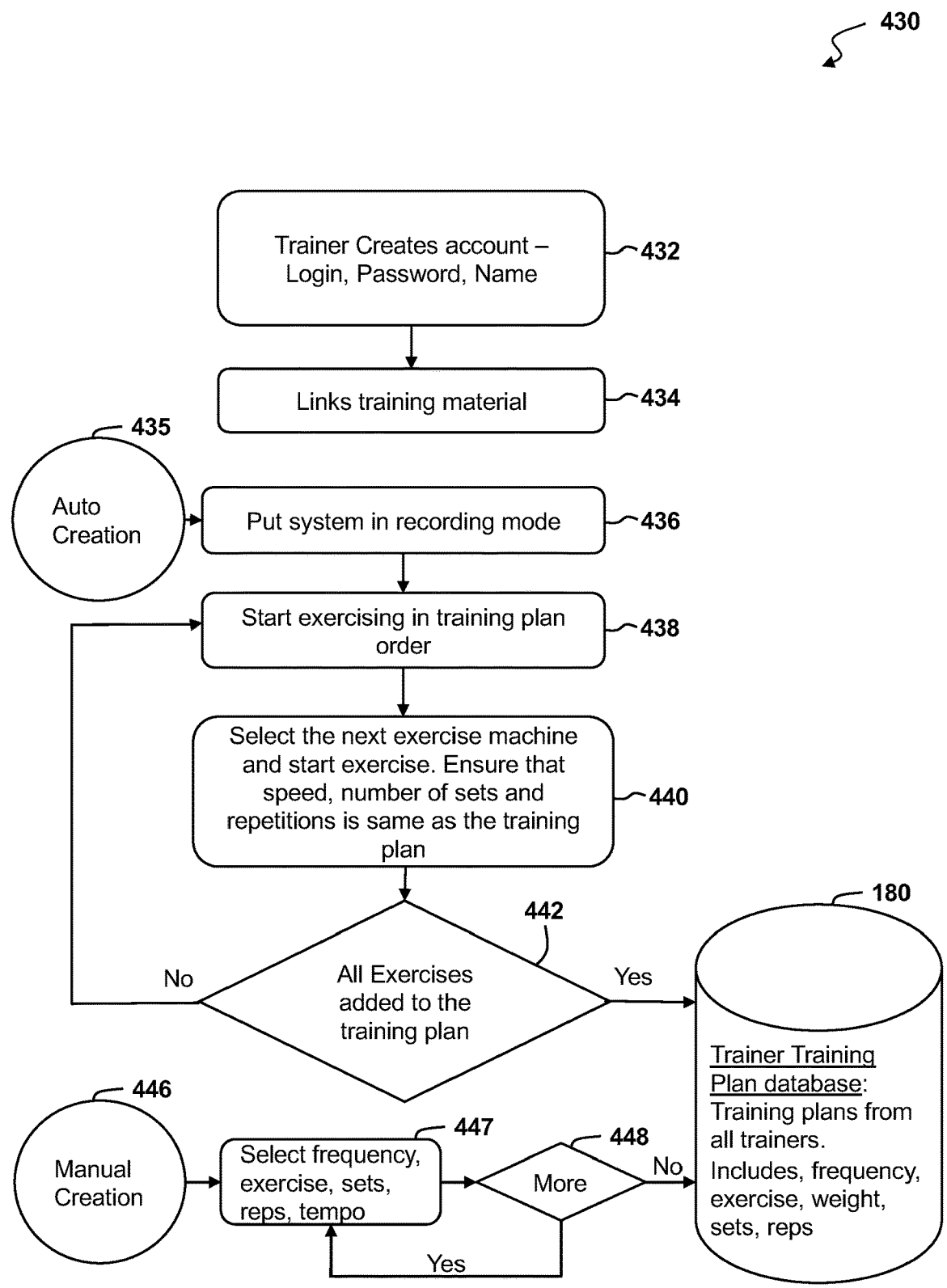
FIG. 3B shows a flowchart of initial Trainer setup and Training plan creation for the system according to one embodiment.

FIG. 3B is an example of a trainer creating a training plan to use the system 430 by adding their information to the trainer 170 and training plan 180 databases (e.g., FIG. 2A). In one embodiment, the trainer accesses a trainer page on a system website and creates their account credentials including login, password, and name, etc. (step 432), and provides URLs to their training material and/or their website (step 434).

To create the training plan in the training plan database 180, in one embodiment, the trainer uses system equipped exercise machines and puts them into recording mode (step 436). In this mode, the exercise machines and/or sensors thereon record all the information in detail including weights, number of sets, repetitions, etc., and speed, movement graphs, etc. in a format that can then be used for a training plan. The trainer then selects the first exercise machine in the training plan and starts their exercise while ensuring that all exercise details like sets and lifting speed etc. are correct (step 438). After they have completed the exercise, they move to a next exercise on the training plan (step 440). When all the exercises are completed, they are added to the training plan database (step 180).

In one embodiment, the trainer may manually create the training plan (step 446). They input the frequency, exercises, sets, repetitions and tempo in the trainer dashboard (step 447) and when all exercises are inputted (step 448) this information is added to the database (step 180).

FIG. 3B-*i* is an example of how training plan may be assigned to a user. The trainer determines the needs of a user and selects one of their training plan (step 872) from the training plan database 180 or may decide to create a new one. The trainer may then assign this training plan (step 874) to the user and this training plan now appears in the user dashboard for them to follow. Depending on the contract between the user and the trainer, the trainer may set a date for the training plan to expire (step 876) so that the user may not be able to use it after that date.

FIG. 3B-*ii* is an example of dynamic or optimal training plan creation 880. A user follows the training plans as created by the trainer and stored in the training plan database 180. The details of the exercises completed by the user are stored in the user exercise database 194. The user exercises are compared with the training plan and the differences may be handled in the following ways.

If there is a minimal difference (step 886) (e.g., there is little difference between the training plan and the exercises as performed by the user), the user may be receiving a continuing notification (step 894) (e.g., the user is informed to continue exercising as they have been. If the user is performing better than the training plan (step 888), then the training plan may manually or automatically be made more demanding (step 896). If the user performance is below (e.g., not keeping up with) the training plan (step 890), then the system may automatically and/or the trainer may intervene to determine the root cause, and may modify the training plan to better suit the user needs (step 897). If the user is performing other exercises that are not on the plan (step 892) (e.g., different weight and/or cardio exercises), the training plan may be dynamically and/or manually altered to include these new exercises, and equivalent exercises that are on the training plan may be removed (step 898).

Figure 3C:
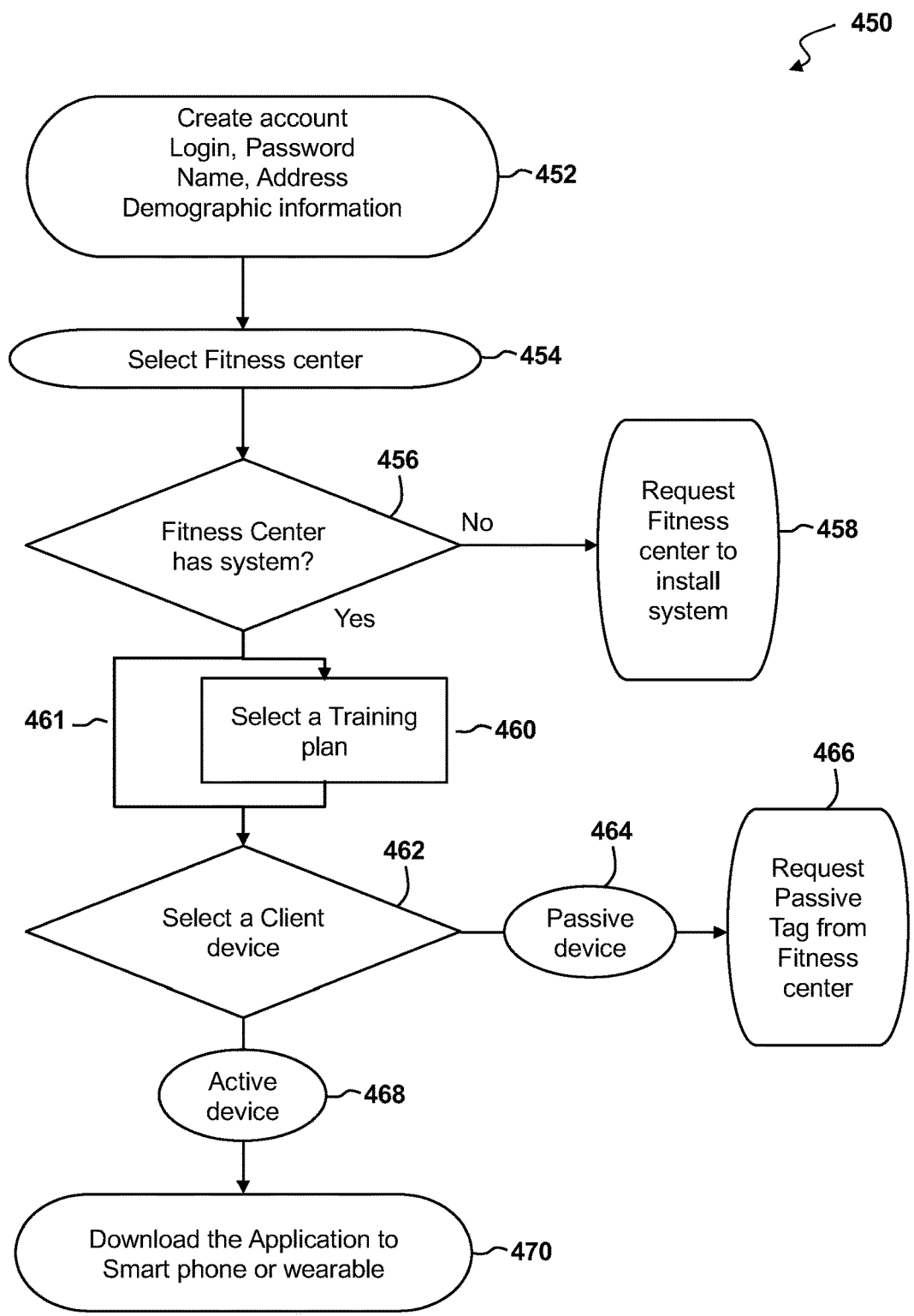
FIG. 3C shows a flowchart of the initial system setup for a User according to one embodiment.

FIG. 3C is an example of an initial system setup 450 for a user according to one embodiment. On a user page of the system website, the user creates his/her credentials, and provides demographic and other fitness related information (step 452). The user then selects a fitness center (step 454). The selected fitness center may be one open to public, may be private or members only (colleges, professional teams, security forces etc.), and/or a fitness machine at home or another location. If this fitness center does not have the system (step 456) or is not in the system database, the user may request them to install it (step 458).

The next step may be to select a training plan (step 460) that is created by a trainer and is in the training plan database 180 (e.g., FIG. 2A). In one embodiment, the user has the option to not use a training plan (step 461), in this case the system will just track the exercises without providing any guidance on training. Then, a user selects a client device that they want to use (step 462). If the user wants to have an enhanced user experience, they may choose an active client device 468 and download a system application (step 470) to their smart phone and/or wearable device. For a simpler user experience, the user may select a passive client device 464 and request a passive tag from their fitness center (step 466).

In another embodiment, the active client device 468 may not have the appropriate PAN connectivity 310 (e.g., FIG. 2D). The user may still have a rich user experience by downloading a system application to their smart phone or wearable while using a passive client 464 that they may get from their fitness center.

Figure 3D:
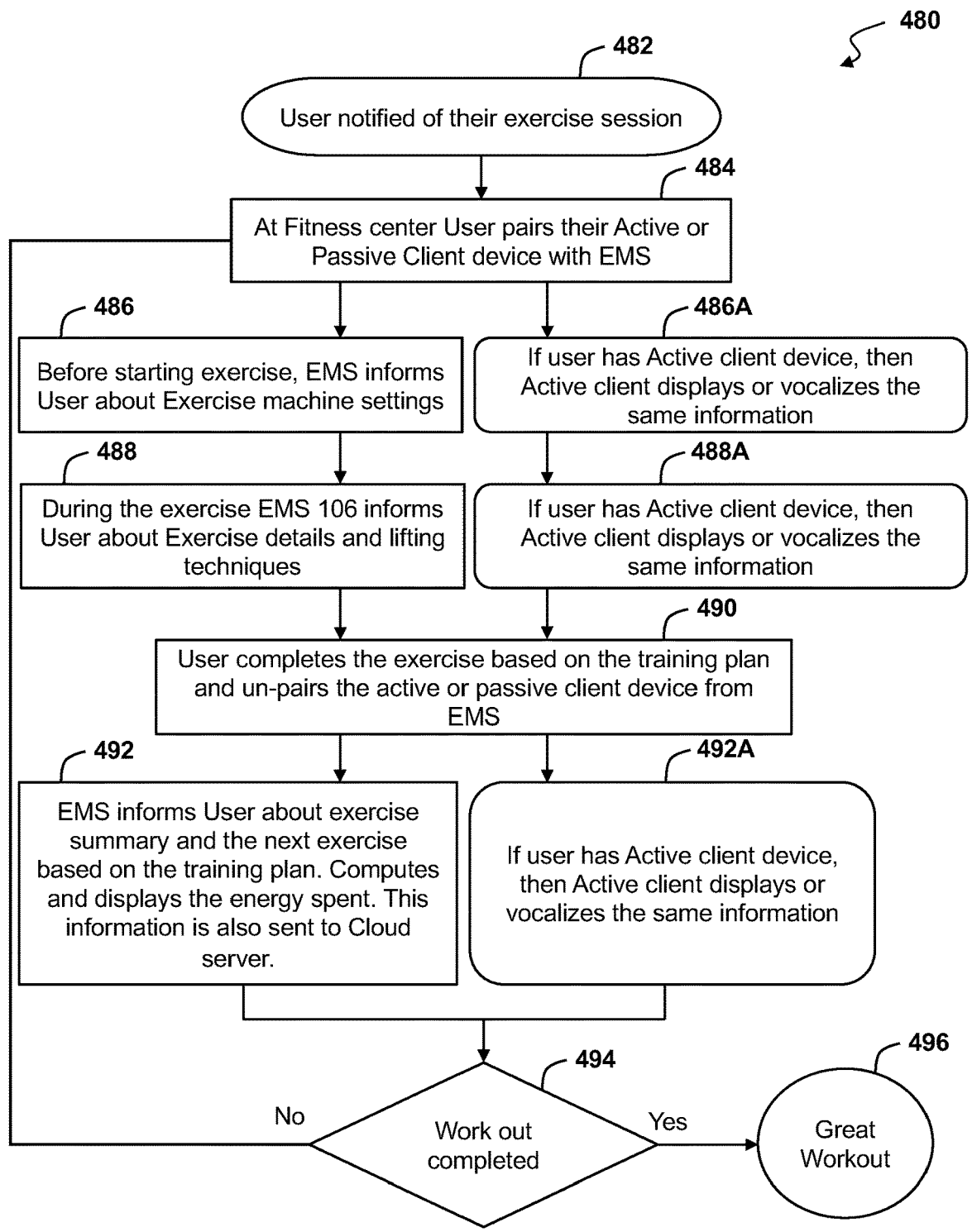
FIG. 3D shows a flowchart how a User may use the system at a fitness center according to one embodiment.

FIG. 3D is an exemplary flowchart 480 of how a user may use the disclosed system at a fitness center. In one embodiment, the user is notified about their upcoming exercise session (step 482). At the fitness center, the user pairs (as described in FIG. 3E) their active or passive client device with the EMS, mounted on the exercise machine (step 484).

Before the user starts the exercise, the EMS may inform the user about exercise machine settings (step 486) like seat height, leg length, etc. These settings depend on user anatomy 126 (e.g., FIG. 2A), which the user may have provided as part of the initial setup and exercise machine properties 168 (e.g., FIG. 2A) stored in the databases 118 (e.g., FIG. 2A). If the user has an active client device, the same information may also be available on the active client device (step 486A). During the exercise, the EMS may also provide exercise details (step 488) like weight to be lifted, duration, number of sets, and repetitions 190 (e.g., FIG. 2A), based on the selected training plan stored in the training plan database 180. If the user has the active client device, the same information may also be available on the Active client device (step 488A). While the user is exercising, the EMS may monitor the progress in real time and may provide feedback on lifting techniques like how fast or slow the weights should be lifted. The weight lifting movements may be visually represented as a graph and compared with the training plan movement graphs 192 (e.g., FIG. 2A) and the user notified if their movements significantly differ from the selected training plan stored in the training plan database 180 (e.g., FIG. 2A).

After the user completes the exercise and un-pairs their active or passive client device from the EMS (step 490), the EMS provides a summary of the completed exercise and a next exercise based on the selected training plan (step 492). Based on accurate information about the exercise, the muscles it used in this exercise, amount of weight lifted, weight lifting speed, number of sets and repetitions, and the user anatomical and demographic information, the EMS may compute and display the number of calories, maximum power, and/or energy spent while doing the exercise. This information may be sent to the cloud server 102 (e.g., FIG. 1) for storage and/or update. If the active client is used, similar information may also be displayed on it (step 492A). The user continues this process until the whole exercise session is completed (step 494) and the exercise session is finished (step 496).

Figure 3E:
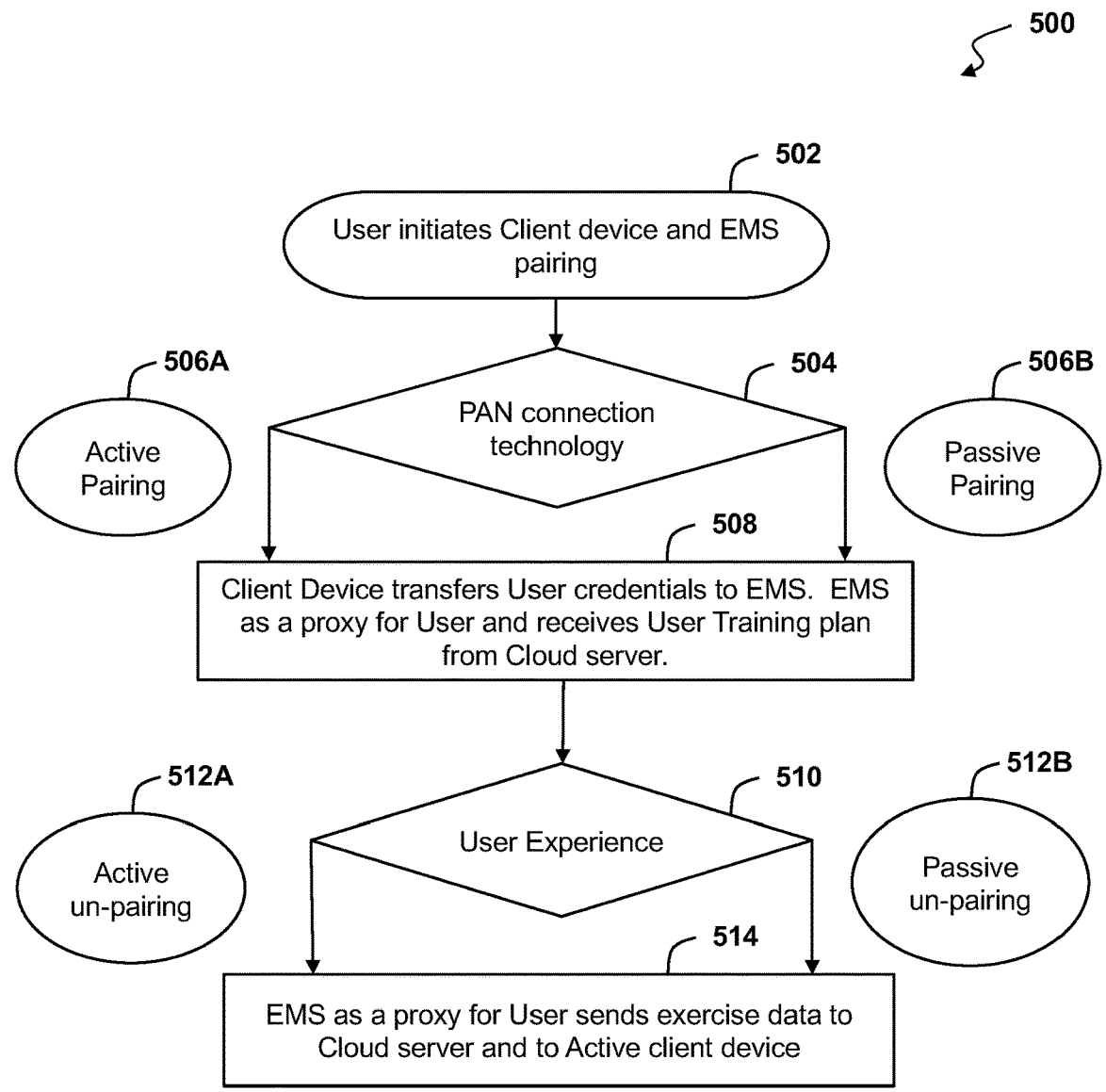
FIG. 3E shows a flowchart of a Client Device pairing with EMS.

FIG. 3E shows a flowchart 500 of how the client device may pair with the EMS. The PAN 230 (e.g., FIG. 2B)

component of the active client device or passive tag 250 (e.g., FIG. 2C) having a communication connection 251 (e.g., a data/control bus) component of the passive client device may be used to connect with the PAN 310 (e.g., FIG. 2D) component of the active sensor link or the PAN 350 (e.g., FIG. 2E) component of the passive link (step 502).

The client device and the EMS may pair in several ways. Active pairing 506A and passive pairing 506B are two embodiments that are considered. The decision to use either active or passive pairing (step 504) depends on the PAN technology on the client device, EMS, and/or the fitness center. For active pairing, the user does some action, for example bringing an NFC component on a client device close (e.g., around 1 inch) to the NFC component on the EMS. Passive pairing does not need a user action and may use technologies like BLE proximity sensing and RFID to pair the client device and EMS automatically when they are in proximity. Passive pairing 506B may lead to conflicts as one client device may attempt to pair with more than one EMS, or two or more client devices may attempt to pair with one EMS. These conflicts may be resolved by asking user visual or audible questions which they might answer by voice or touch.

While paired, the EMS is a proxy for the user client device and acts on its behalf (step 508). After the pairing, the client device transfers user credentials to the EMS which the EMS sends to the cloud server 102 (e.g., FIG. 1) and receives the user training plan. While the user is using the exercise machine, the EMS collects all exercise related information on behalf of the user and shares it with the cloud server 102 (e.g., FIG. 1) and the client device (step 514). When un-paired, the EMS may send all the exercise details like weights, number of sets, repetitions, lifting speed, range, energy, maximum power, and/or calories spent etc. to the cloud server 102 (e.g., FIG. 1) and store this data in the user exercise summary database 194 (e.g., FIG. 2A) (step 514). EMS may also share this information with the active client device.

The un-pairing decision may be based on the user experience (step 510). In this disclosure, two embodiments are considered the active un-pairing 512A or passive un-pairing 512B. Active un-pairing 512A needs user action (e.g., bringing a NFC component of the client device close to a NFC component of the paired EMS). Passive un-pairing 512B happens without user action, for example, when the client device gets out of the EMS range or when the client device is paired with another EMS.

Figure 4A:
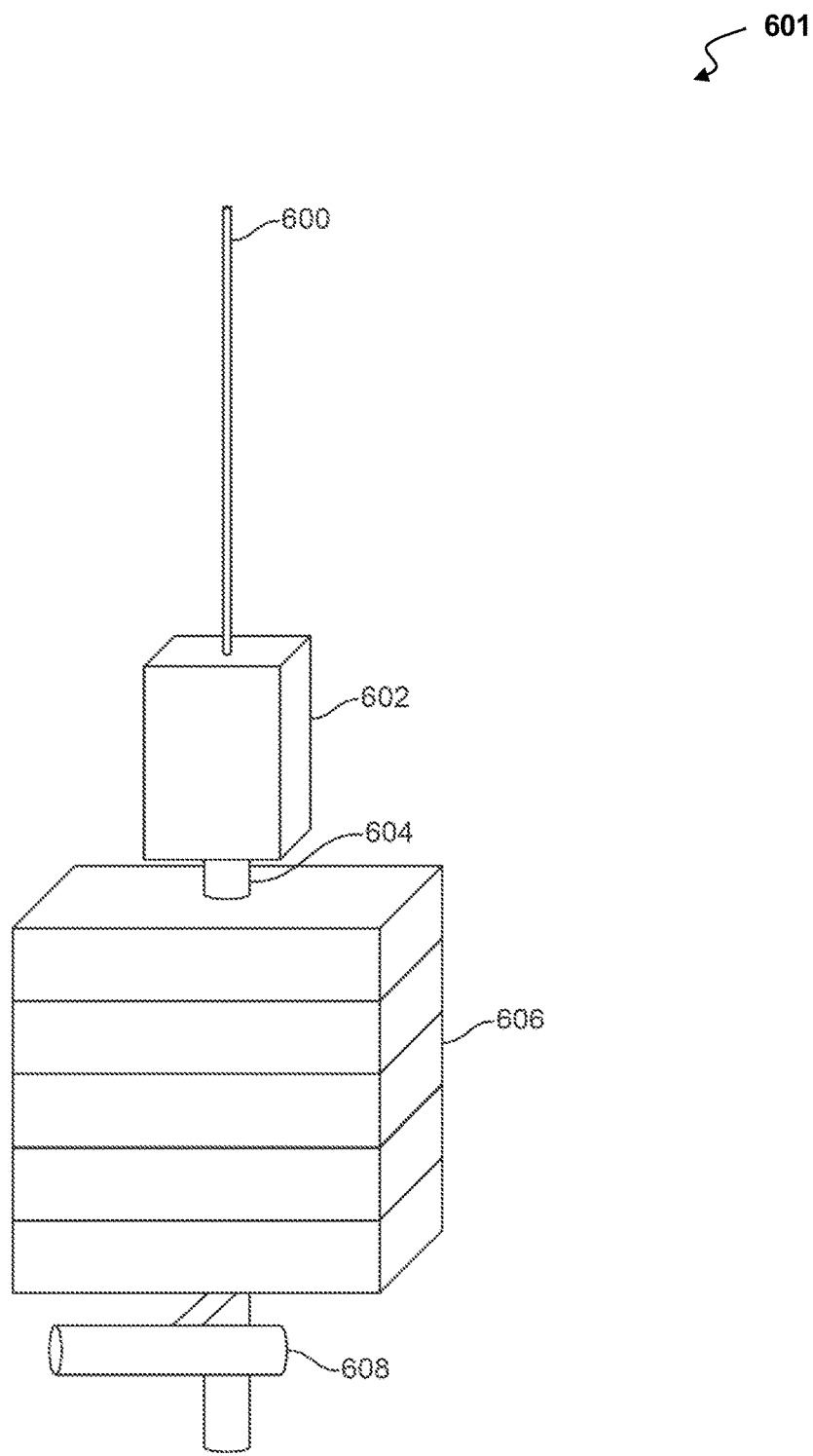
FIG. 4A shows a schematic of Type-A Active Sensor Link.

FIG. 4A shows an exemplary embodiment of an exemplary exercise machine 601 having a Type-A, Active Sensor Link 602 comprising an EMS which may be mounted on weight exercise machines, resistance exercise machines (e.g., Bowflex), resistance bands etc. The Type-A Active sensor link 602 may be connected to the cable 600 that connects to the handles that the user pushes and/or pulls to lift the weights 606. The other end of the Type-A Active sensor link 602 is connected to a slotted rod 604 that carries the weights 606 and a pin 608, which is used to select the desired number of weights 606.

To measure the weight and/or cable tension, the Type-A Active sensor link 602 may have a load cell type weight sensor and/or tension meter to measure the weight lifted and the accelerometer and/or the gyroscope sensors to measure the motion from which information like number of sets, repetitions, and energy used may be derived.

Figure 4B:
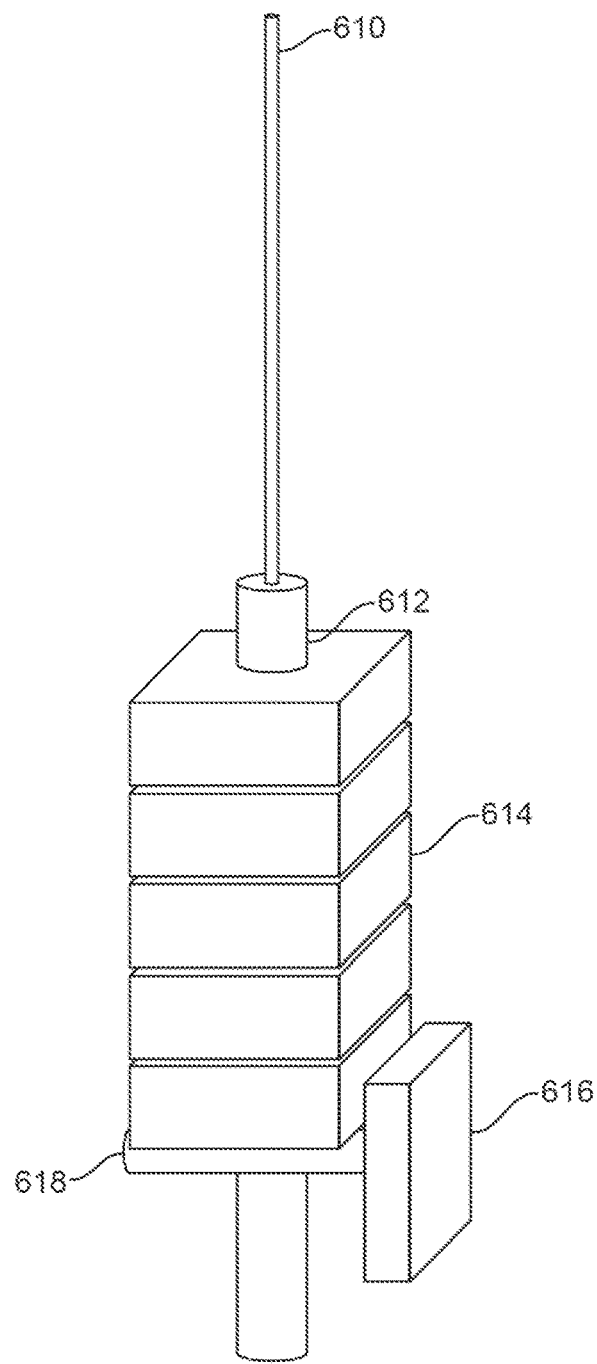
FIG. 4B shows a schematic of Type-B Active Sensor Link.

FIG. 4B shows an exemplary embodiment of an exercise machine 611 having a Type-B Active Sensor Link assembly comprising an EMS connected thereon that may have two parts: a weight sensor pin 618 and an electronics box 616. The Type-B Active Sensor Link assembly (616, 618) may be mounted on a weight exercise machine. The weight sensor pin 618 is inserted in a slotted rod 612 to carry weights 614 that are pulled by a cable 610 that is attached to the handles that the user pushes and/or pulls to lift the weights 614.

During the exercise, the weights are supported by the weight sensor pin 618. The weight sensor pin 618 may use a capacitive, piezoelectric and/or strain gauge, etc. based sensor. An active sensor link computer 260, a LAN 300, a PAN 310, and other sensors like the accelerometer 282 and the gyroscope 284 may be housed in the electronics box 616, which may be mounted on the weight sensor pin 618. To change the weights, the user holds the electronics box 616 and pulls out the attached weight sensor pin 618 and places it at the desired number of weights 614. The weight sensor, along with the accelerometer and/or the gyroscope sensors measure the motion from which information like number of sets, repetitions, and energy used may be derived.

FIG. 4B-*i* illustrates the top cross-sectional view of the exercise machine 611 having the weight sensor pin 618 inserted into the slotted rod 612 and weights 614. The weights 614 are supported by the weight sensor pin 618.

FIG. 4B-*ii* depicts a cross-sectional view of the pin 618. In this exemplary embodiment, the forces applied by the weights cause bending strain. In one embodiment, the weight sensor pin 618 has pin relief features 617, which concentrate the weight and support forces on predefined and fixed areas. In another embodiment, these one or more relief features 617 may be removed or others added. In one embodiment, two strain gauges 619 are disposed in the pin 618, which can be used to measure strain using the half-Wheatstone bridge. In another embodiment, quarter, or full Wheatstone bridge configurations may be used. A cross sectional view of the strain gauge 619 is shown across line A-A.

In another embodiment of the weight sensor pin 618, the forces applied may be in shear. In one embodiment, the pin relief features 617 may not be present. In one embodiment, two strain gauges 619 in a cross pattern may be used in a half Wheatstone bridge configuration. In another embodiment, pin relief features 617 may be present and strain gauge 619 may be in quarter, or full Wheatstone bridge configuration.

FIG. 4B-*iii* illustrates a cross-sectional view of the weight sensor pin 618 with strain gauges under a typical loading scenario. The top strain gauge is oriented at an angle $\Theta$ from the horizontal. Due to this orientation the bending force applied on this strain gauge is $F \cos \Theta$, thereby resulting a smaller measured weight reading. To compensate for this, an accelerometer sensor may be used to measure acceleration due to gravity as g1 in this orientation as compared to the normal value g when the angle is 0. The angle $\Theta$ is then given by $\cos [\Theta = g1/g]$.

Figure 4C:
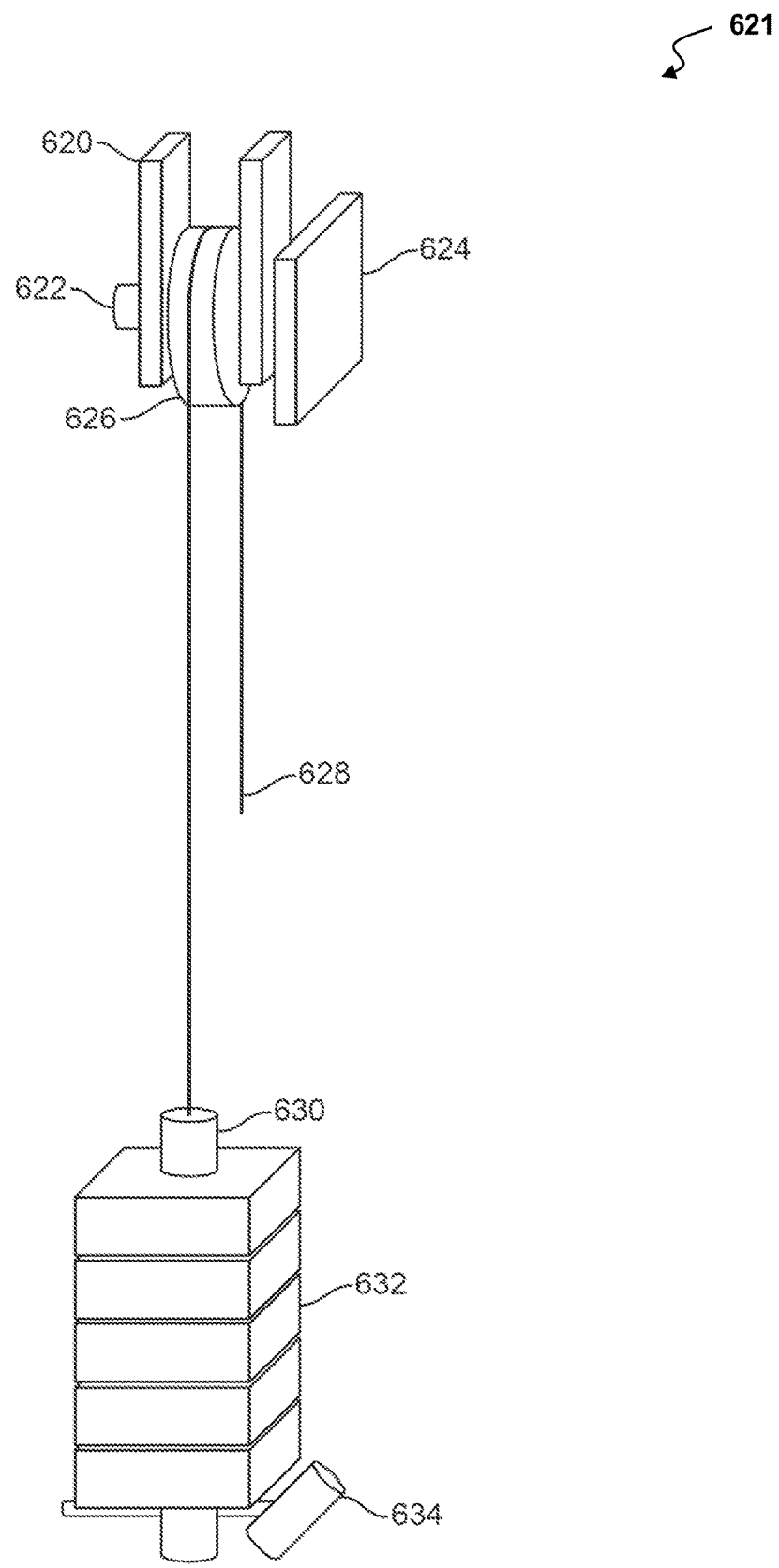
FIG. 4C shows a schematic of Type-C Active Sensor Link.

FIG. 4C shows an exemplary embodiment of an exercise machine 621 having a Type-C Active Sensor Link comprising an EMS connected thereon. It may have three parts: a weight sensor pin 622, a rotation measurement sensor pulley 626, and an electronics box 624. Type-C Active sensor link assembly (622, 624, 626) may be mounted on a weight exercise machine, resistance exercise machine, etc. The pulley assembly in this active sensor link is supported by a bracket 620 that is attached to the exercise machine. As a cable 628 goes over the pulley, on one end it is attached to the handle that the user pushes and/or pulls to lift the weights 632. The other end of the cable 628 is attached to the weights 632 that are supported by the pin 634 that the user inserts into the slotted rod 630.

To measure the lifted weight, the weight sensor pin 622 may use sensors like strain gauge, piezoelectric and/or compression load pin, etc. The active sensor link computer 260, LAN 300, and PAN 310 (e.g., FIG. 2D) may be housed in the electronics box 624. The sensor pulley 626 may have a rotation measurement sensor like a rotary encoder, an optical encoder, and/or a Hall Effect-based sensor, etc. These sensors are used to measure rotation and weight from which the number of sets, repetitions, and/or energy used can be derived.

Figure 4D:
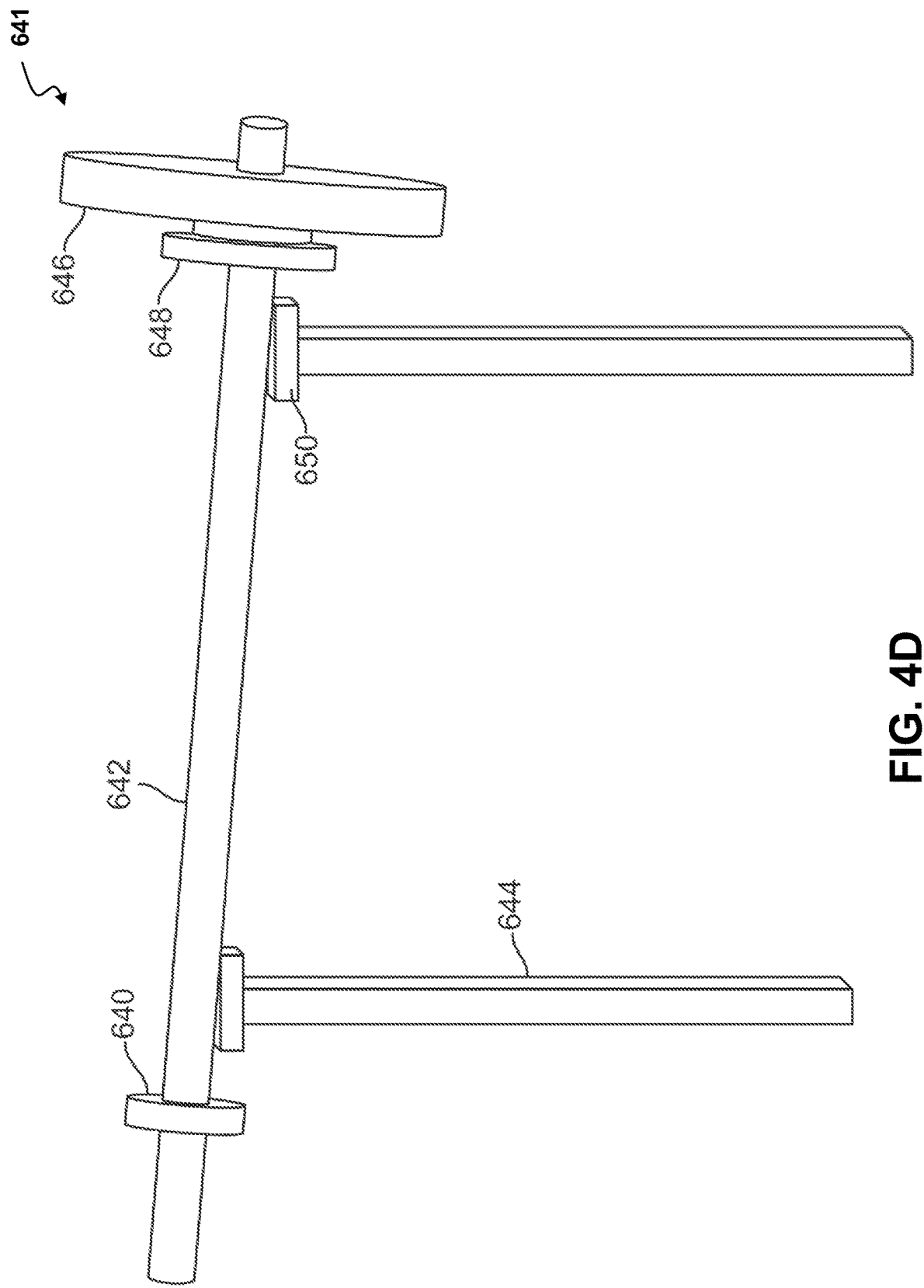
FIG. 4D shows a schematic of Type-D Active Sensor Link.

FIG. 4D shows an exemplary embodiment of an exercise equipment setup 641 of a barbell having a weight mounted on one side and having a Type-D Active Sensor Link. It may have two parts: the support sensor 650, which is used to measure the weight, and a sensor collar 648, which may have accelerometer and/or gyroscope sensors to measure motion. The Type-D Active Sensor Link assembly 648, 650 may be mounted on barbells 642 that are used for bench press and/or squat type exercises and/or be mounted on chest press and/or leg press machines that use weight plates. The collar 640 used to hold the weight plates 646 are fixed to the barbell 642, which carries the desired number of weight plates 646. The barbell assembly sits on the support pillars 644.

Measuring the lifted weight may use a capacitive, piezoelectric, and/or strain gauge, etc. sensor 650 built into the support 644. The weight is measured when the user is resting before and/or after the exercise. The support sensor 650 may be on one or both sides of the support 644. The accelerometer, gyroscope, and other motion sensors, may be mounted on the barbell in the sensor collar 648. In one embodiment, the support sensor 650 may also have the other components of the active sensor link including the computer 260, LAN 300, and/or PAN 310 (e.g., FIG. 2D). In another embodiment, the computer 260, LAN 300, and/or PAN 310 (e.g., FIG. 2D) may be in the sensor collar 648. The sensors (648, 650) may use the LAN 300 and/or PAN 310 to communicate with another sensor, the client device, and/or the cloud.

The support sensor 650 measures the weight of the barbell 642 and weight plates 646 stacked by the user and the sensor collar 648 measures the movement of the barbell 642. To get the complete exercise information, these two pieces of data are combined.

In one exemplary embodiment, both the support sensor 650 and sensor collar 648 individually report the data to a paired client device 104a and cloud server 102 (e.g., FIG. 1). In this case the user has to pair their client device 104a (e.g., FIG. 1) both to the sensor collar 648 and the support sensor 650.

In another embodiment, the data from one sensor is sent to the other coupled sensor and then reported comprehensively to the paired client device and cloud server. This coupling allows both these sensors to act like a single unit and the user has to pair their client device 104 only to one of the sensors (648, 650).

At a fitness center, there might be a plurality of barbell supports 644 and attached support sensors 650 and a plurality of barbells 642 and attached collar sensor 648. Thus, a barbell 642 and attached sensor collar 648 may be moved to another support 644 and attached support sensor 650. For comprehensive reporting to work correctly, the data from the sensor collar 648 should be sent to the coupled support sensor 650 on which the barbell 642 is resting.

In one exemplary embodiment, this coupling may be permanent, so only one sensor collar 648 may pair with one predefined sensor support 650. In another embodiment, the support sensor 650 and collar sensor 648 coupling may be temporary and based on proximity.

In yet another embodiment, the support sensor 650 and collar sensor 648 coupling may be based on the event when the barbell 642 is lifted from the support 644. At this event, collar sensor 648 may start reporting motion and the support sensor 650 may start reporting zero weight. It can be inferred that the particular collar sensor 648 and the particular support sensor 650 are coupled when both of them report the lifting event at about the same time.

The accelerometer, gyroscope and/or weight sensors may be to measure the motion and/or weight from which information like number of sets, repetitions, and calories burned can be derived.

Figure 4E:
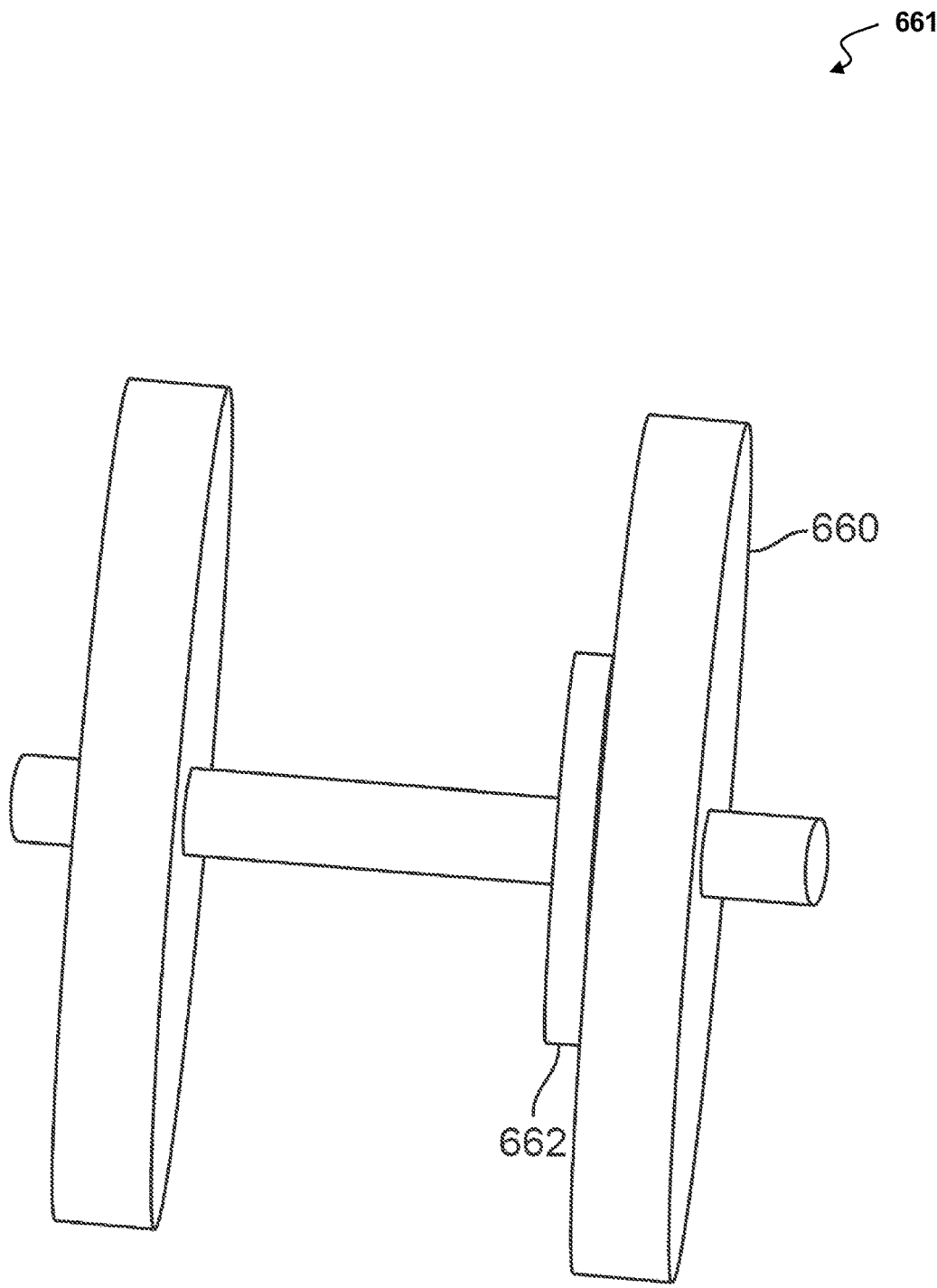
FIG. 4E shows a schematic of Type-E Active Sensor Link.

FIG. 4E shows and exemplary embodiment of an exercise equipment setup 661 having a Type-E Active sensor link. This sensor may be mounted on a dumbbell, fixed barbell, etc. type free weights 660 where the weight cannot be altered. This active sensor link 662 may have computer 260, LAN 300, and PAN 310 (e.g., FIG. 2D) and sensors like the accelerometer and/or gyroscope. As the weight cannot be altered, there may not be a need for a weight measuring sensor. The weight may be pre-configured when the collar sensor 662 is attached to the dumbbell 660 or barbell. The accelerometer and/or gyroscope sensors may measure the motion of the dumbbell 660, and along with the weight information, the number of sets, repetitions, and calories burned may be derived. The sensors 662 may use the measured motion to determine a type of exercise performed based on the range of motion (e.g., distinguish between a bicep curl and a bench press).

FIG. 4F-i shows an exemplary embodiment of an exercise equipment setup 651 showing of one side of a barbell 642 with a collar 640 and sleeve 652. One or more plates 646 may be loaded and at the end is an electronics box 654, which houses the sensors, processor, and batteries.

FIG. 4F-ii shows the exercise equipment setup 651 cross-section of a barbell 642 with a collar 640 and a sleeve 652. In this embodiment, the forces applied cause bending strain. The sleeve 652 is put on barbell 642 and, in one embodiment, relief features 655 are used to concentrate the weight of one or more plates 646 in predefined and fixed areas. In another embodiment, one or more of these relief features 655 may be removed or others added. In one embodiment, two strain gauges 656 may be used to measure strain using the half-Wheatstone bridge. In another embodiment, quarter, or full Wheatstone bridge configurations may be used. A cross-sectional view of the strain gauge 656 is shown across line A-A.

In another exemplary embodiment of the barbell 642, the forces applied may be in shear. In one embodiment, the relief features 655 may not be present. In one embodiment, two strain gauges 656 in a cross pattern may be used in a half Wheatstone bridge configuration. In another embodiment, relief features 655 may be present and strain gauges 656 may be in quarter, or full Wheatstone bridge configuration. In a typical usage scenario, the strain gauges 656 may not be horizontal and vertical orientation, as shown in FIG. 4B-iii, in which they are at an angle $\Theta$ with the horizontal. To compensate for this, an accelerometer sensor may be used to measure the acceleration due to gravity as g1 in this orientation as compared to the normal value g when the angle is 0. The angle $\Theta$ is then given by $\cos\theta = g1/g$ As more plates 646 are added, not only the weight increases, but the mean center of mass moves to the right. This makes the strain to weight relationship non-linear. Also, different weight plates 646 may have different thicknesses and sizes. The strain gauges 656 may be calibrated by using different weight plates 646 and information stored in a look up table.

With respect to FIG. 4G-i, an exercise machine 603 of Type-G Active Sensor Link assembly is shown in a top, cross-sectional view. The exercise machine 603 may include an electronics box 617 with a barcode reader or camera 615 along with a flash and a pin 609. In one embodiment, the barcode reader 615 is an optical scanner for reading printed barcodes. The printed barcodes may encode information related to the exercise machine 603, such as the amount of weight being lifted. In some embodiments, the barcode reader 615 may be an optical scanner including a light source, a lens and a light sensor for translating optical impulses into electrical signals. In some embodiments, the barcode reader 615 may contain decoder circuitry that may analyze image data from the sensor and output a signal relating to the image data. In other embodiments, the barcode reader 615 may be a camera, such as an RGB camera. The barcode reader 615 may use Optical character recognition, Pattern Recognition or Machine Learning technologies to analyze a symbol, such as a weight printed on a weight plate, described below.

The pin 609 may be inserted in a slotted rod 627 which lifts a weight 605 with an affixed barcode 613 or a weight value in pounds (lbs) or kilograms (kg) indicated by a number 665 (FIG. 4G-v). The barcode reader or camera 615 may be pointed at the barcode 613 or number 665 to read the barcode 613 or number 665. In some embodiments, the barcode 613 may be a Quick Response (QR) code or matrix barcode. In other embodiments, the barcode 613 may be any symbol detectable by the barcode reader 615, including, but not limited to, polygons, text, symbols, and the like.

With respect to FIG. 4G-ii, an exercise machine 619 having a Type-G Active Sensor Link assembly 633 is illustrated in front view. A barcode reader or camera and a pin, such as barcode reader 615 and pin 609 of FIG. 4G-i are present in FIG. 4G-ii, though not visible in this front view. This Type-G Active Sensor Link assembly 633 may be mounted on a weight exercise machine, such as exercise machine 619. The weight pin (such as pin 609 in FIG. 4G-i) may be inserted into a weight 605 through a hole 631 in the weight 605. A slotted rod 627 carries weights 605 that are pulled by a cable 623. The cable 623 may be attached to handles, grips, bars, or the like on the exercise machine 619 that a user pushes and/or pulls to lift the weights 605.

In one embodiment, each weight 605 may have a unique barcode 613 or a weight number 665 (FIG. 4G-v) affixed to an outer surface of each weight 605. In another embodiment, the unique barcode 613 or weight number 665 may be printed on each weight 605. In another embodiment, the unique barcode or weight number may be embossed into each weight 605. The unique barcode 613 encodes the actual weight a user would lift when the weight sensor pin is inserted into the corresponding hole 631 in the weight 605. The barcode reader or camera (such as barcode reader 615 or camera in FIG. 4G-i) may be placed directly in front of the barcode 613 or weight number 665 such that the barcode reader may read the weight that is being lifted.

FIG. 4G-iii depicts a photo 643 captured by a barcode camera, such as barcode reader 615 in FIG. 4G-i when the barcode reader is oriented in line with the barcode 613. The photo 643 shows a portion of the weight 605 and the barcode 613.

In one embodiment, the barcode 613 may use discrete symbology with two or more different bar widths, such as three dark bars and two light bars. Other combinations of bar widths are possible and contemplated. This combination yields 243 unique symbols which may be used to encode each weight, such as weight 605. In one embodiment, there may be ninety different weights which can be encoded using 6 bits of information. In this embodiment, a 2-bit checksum may be used for error correction for a total of 8 bits of information. In one embodiment, error correction is determined with a Hamming program.

In one embodiment, the camera may take a photo of the barcode 613 or weight number 665 when a user pulls the weights 605, such as when movement is detected. In another embodiment, the photo may be taken just after the completion of an exercise, such as when movement has ceased, when a user enters a prompt, when a user proximity is detected/lost, or the like.

FIG. 4G-iv shows a photo 653 captured by a barcode reader, such as barcode reader 615 of FIG. 4G-i when a pin is rotated at an angle Θ with respect to horizontal. Photo 653 captures a weight plate 605 and a barcode 613. As a result of this rotation, a portion of the barcode 613 may be cutoff as it is out of the field of view of the barcode reader.

In one embodiment, a Type-G Active Sensor Link Assembly, such as Type-G Active Sensor Link assembly 633 of FIG. 4G-ii may have an accelerometer which may be used to calculate the rotation angle Θ of the Active Sensor Link assembly 633. The barcode photo 653 may be corrected based on the rotation angle Θ of the pin calculated by the accelerometer. A corrected photo 658 is shown as having been rotated to align the barcode 613 to a horizontal orientation.

In one embodiment, to determine a barcode from the barcode photo 653, the number of dark pixels in each of the dark vertical lines of the barcode 613 is counted. The number of dark pixels may be divided by the number of pixels in the particular barcode height 670 of the barcode 613. In another embodiment, the number of pixels along each of the dark lines, such as three lines, may be counted and an average value may be used. One of these lines is in the middle of the barcode, another above and the one below the middle line.

FIG. 4G-v depicts a photo 663 captured by the camera, such as the camera 615 in FIG. 4G-i, where the photo 663 is oriented in line with a weight number 665. In one embodiment, the weight number 665 may be analyzed by using standard Optical Character recognition, Pattern Recognition or Machine Learning technologies.

FIG. 4G-vi shows a photo 667 captured by the camera 615 of FIG. 4G-i when a pin is rotated at an angle Θ with respect to horizontal. Photo 667 captures a weight plate 605 and a weight number, such as weight number 665 of FIG. 4G-v. As a result of this rotation, a portion of the number 665 may by cutoff as it is outside the view of the camera 615.

In one embodiment, a Type-G Active Sensor Link Assembly, such as Type-G Active Sensor Link assembly 633 of FIG. 4G-ii may have an accelerometer which may be used to calculate the rotation angle Θ of the Active Sensor Link assembly 633. The photo 667 may be corrected based on the rotation angle Θ of the pin calculated by the accelerometer. A corrected photo 669 is shown as having been rotated to align the weight number 665 to a horizontal orientation.

In one embodiment, machine learning algorithms may be used to correctly read the partial weight numbers by using training sets that have numbers occluded like weight number 665 as shown in 669.

Figure 5A:
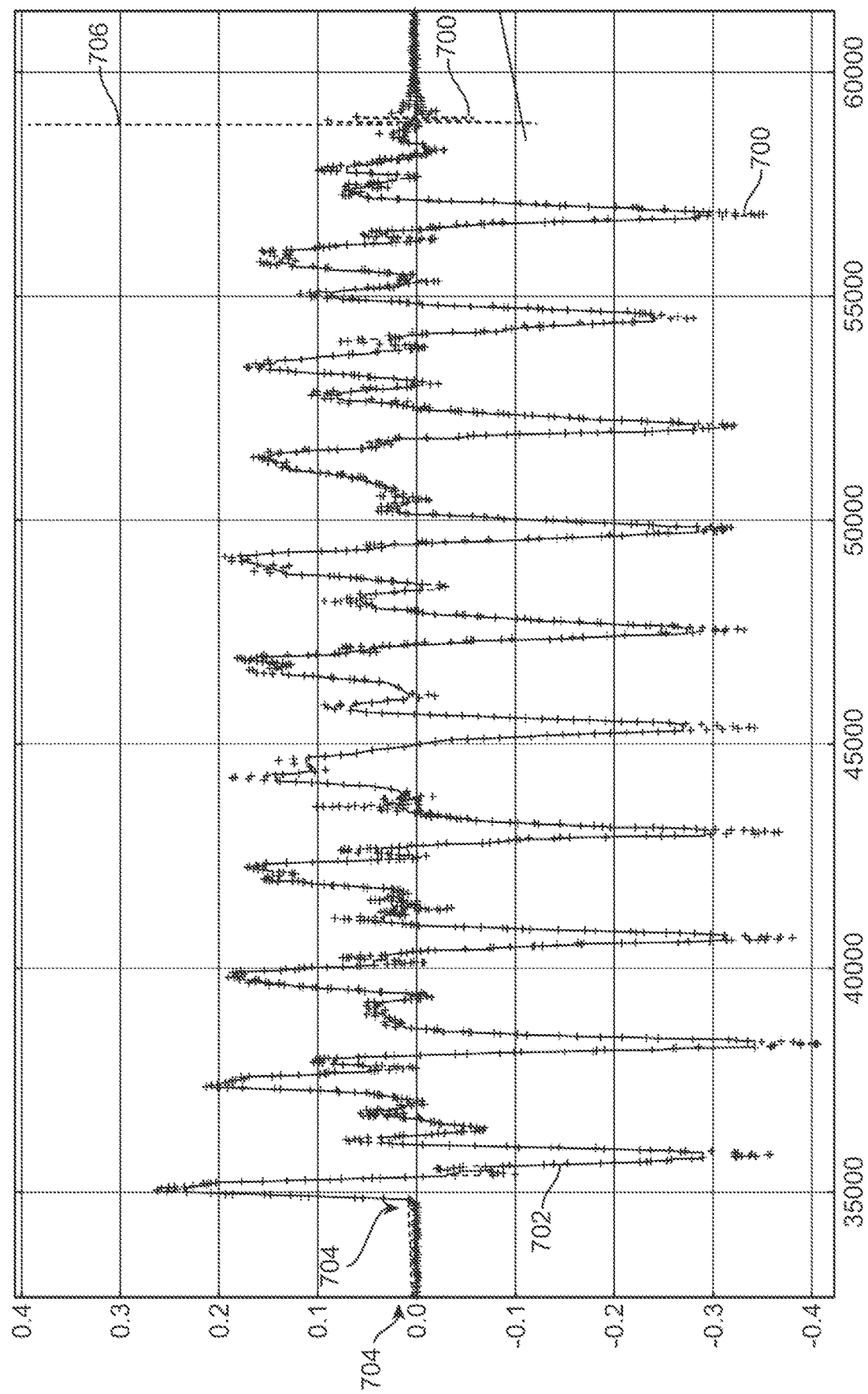
FIG. 5A shows the raw and filtered acceleration plot.

FIG. 5A shows an example of output 700 (as dash line) from an acceleration sensor for the z-axis plotted against time. The accelerometer sensor is mounted such that the z-axis is pointing upwards which is along the weight movement direction. This data is generated from a Type-A Active sensor link 602 (e.g., FIG. 4A).

During this exercise, the user completed one set and ten repetitions. In this plot, the repetitions show up as the ten troughs. In the beginning and the end, the weight was stationary and that is shown by a flat region 704 of the acceleration plot. Since the sensor is very sensitive, the raw data is very noisy with a lot of overshoots and undershoots as expected. Towards the end, the acceleration plot shows a ringing 706. This is due to the weights being lowered and brought to rest with a jerk movement on top of other stationary weights.

To smoothen the data, a twenty-one tap median filter was applied to the raw acceleration data and the resulting output 702 is shown as a solid line. As expected, the median filter data removes a lot of overshoots, undershoots and ringing.

Figure 5B:
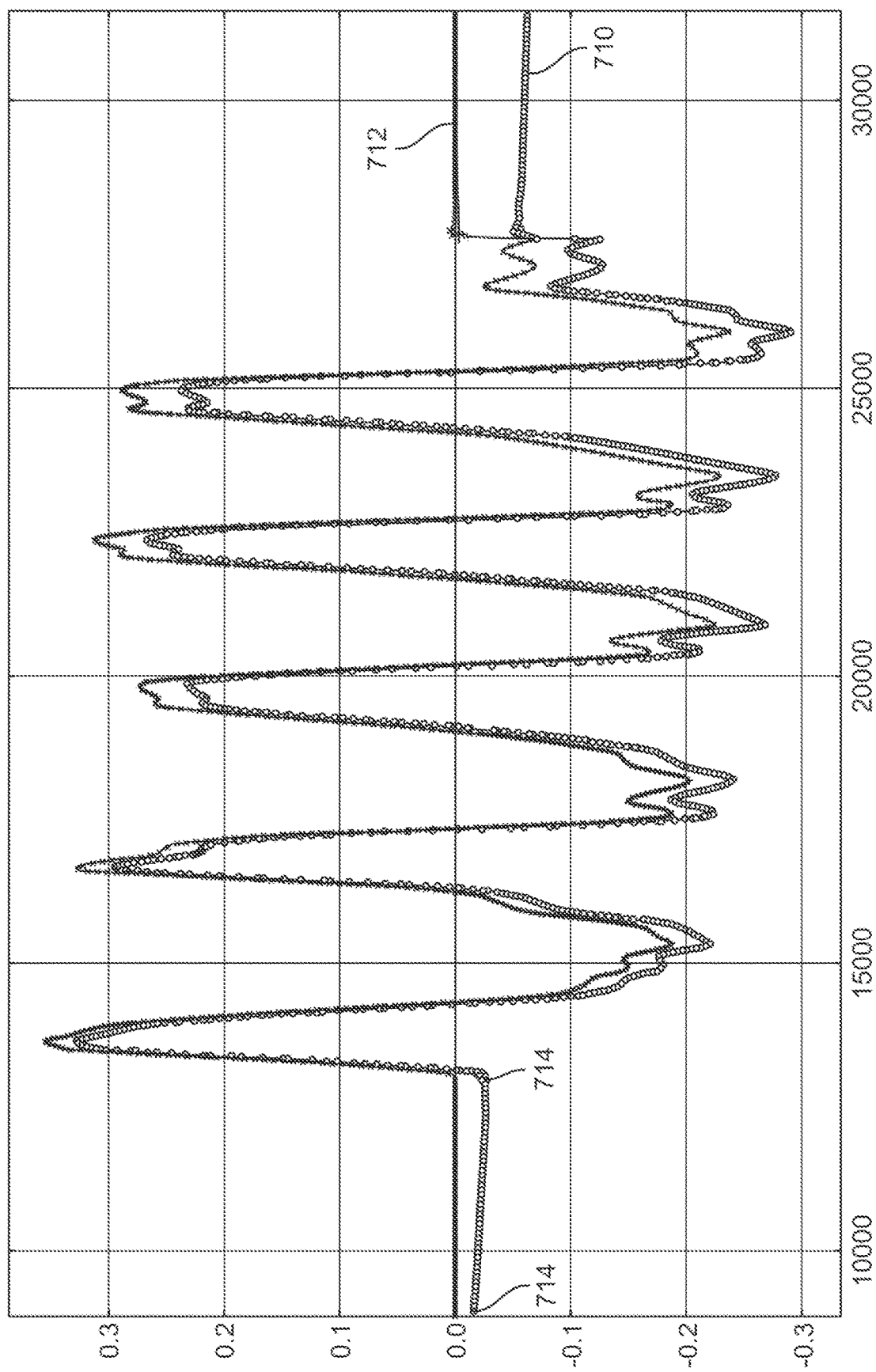
FIG. 5B shows the velocity and compensated velocity plots.

FIG. 5B shows an example of computed velocity plot 710 from an acceleration sensor for the z-axis plotted against time. The accelerometer sensor is mounted such that the z-axis is pointing upwards which is along the weight movement direction. This data is generated from a Type-A Active sensor link 602 (e.g., FIG. 4A). By definition, the velocity is area under the acceleration curve and is computed by taking the cumulative sum of the acceleration values.

During this recorded exercise, the user completed one set and five repetitions. In this plot, the repetitions show up as the five troughs. As expected, the plot are much smoother than the acceleration plot but the velocity plot shows both offset from zero and a drift pointing in the negative direction. For an ideal sensor the velocity before starting the exercise should be 0.0 and the plot should be flat 714. This type of drift is common in accelerometers as minor acceleration offset errors add up and show as drift in velocity computations.

In another embodiment, different high pass filers may be applied to the raw data. These filters are designed to remove the constant drift. Velocity is computed as area under the filtered acceleration curve by taking the cumulative sum of the filtered acceleration values.

For accurate calculations, this velocity drift has to be compensated, and drift compensated velocity plot 712 has zero velocity before and after the exercise. In one embodiment, this compensation is done in the following steps disclosed herein.

Find the time interval before starting the exercise or between the sets when the weight is not moving. Next, approximate the velocity plot during this time interval by a straight line using a least squares fit algorithm. In another embodiment, other line or higher order curve fitting algorithms may be used. The next step is to subtract this fitted straight line from the velocity plot for the duration prior to, and during, the exercise set. This algorithm may be applied to all sets during the exercise.

Figure 5C:
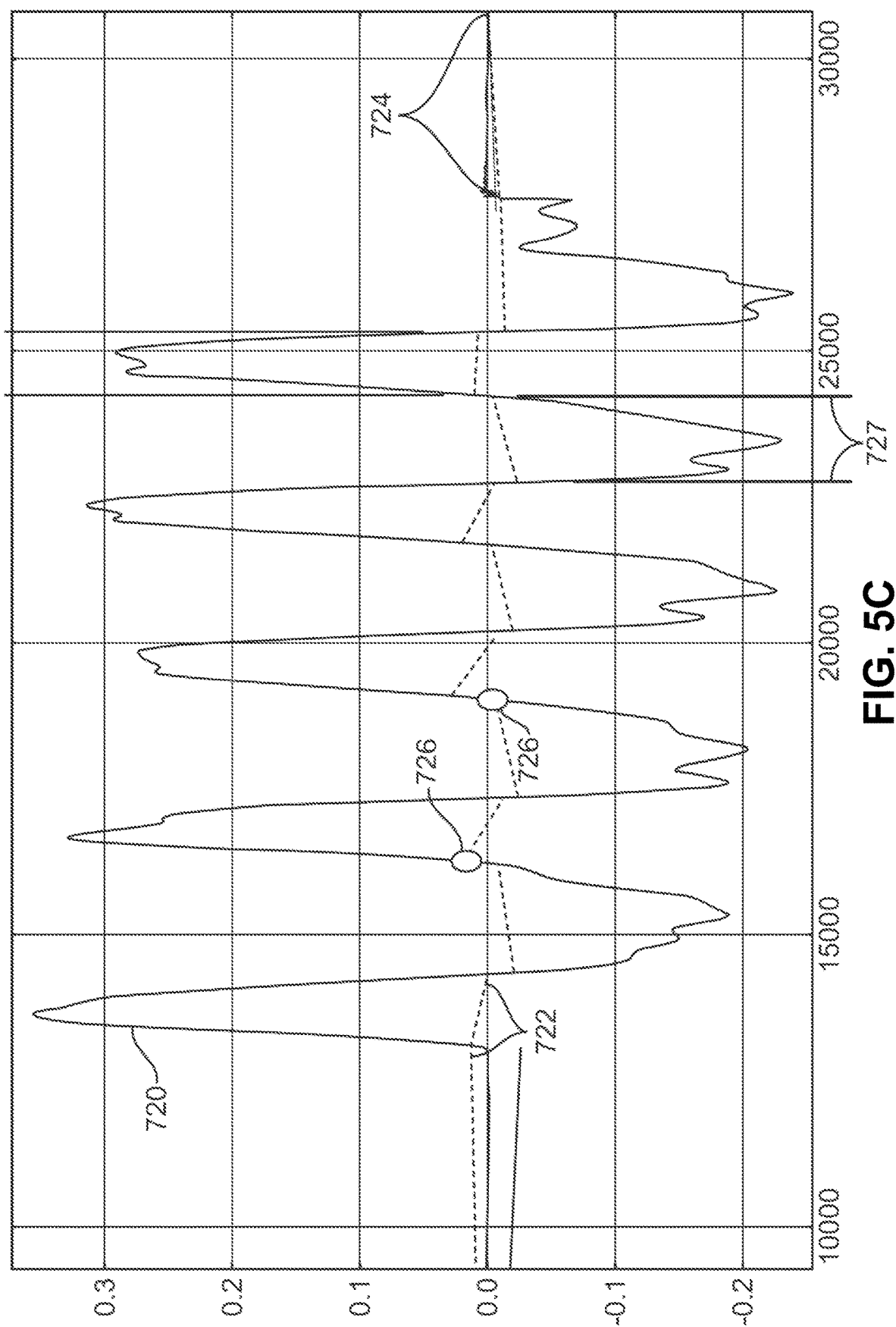
FIG. 5C shows zero crossing for the compensated velocity plot.

FIG. 5C shows an example of a compensated velocity plot 720 from the acceleration sensor for the z-axis plotted against time. The accelerometer sensor is mounted such that the z-axis is pointing upwards which is along the weight movement direction. This data is generated from a Type-A Active sensor link 602 (e.g., FIG. 4A). During this exercise, the user completed one set and five repetitions. In this plot, the repetitions show up as the five troughs.

In one embodiment, the zero band point calculation algorithm 730 is presented. Some of the zero band points are shown. This algorithm is used to calculate various quantities of interest like number of sets, repetitions etc. and to compensate the velocity plot. To eliminate noise, a band around zero velocity is established. This may be based on a percentage of the difference between maximum and minimum velocity value.

If the compensated velocity is outside the Zero tolerance band 722 for a duration longer than a tolerance value based on the minimum time taken for a repetition, it is considered that the user completed half a repetition. This repetition tolerance may be empirically found and it may be different for each exercise machine or exercise. The weight lifting time for a repetition is the time when the velocity is negative 727 and the weight dropping time for a repetition is the time when the velocity is positive 728. The velocity crosses between negative 727 and positive 727 at points 726.

If the velocity is within the Zero tolerance band 724 for a duration longer then a tolerance value based on the minimum resting time between sets, it is considered that the user is resting before starting a new set. This set tolerance may be empirically found and may be different for each exercise machine or exercise.

Figure 5D:
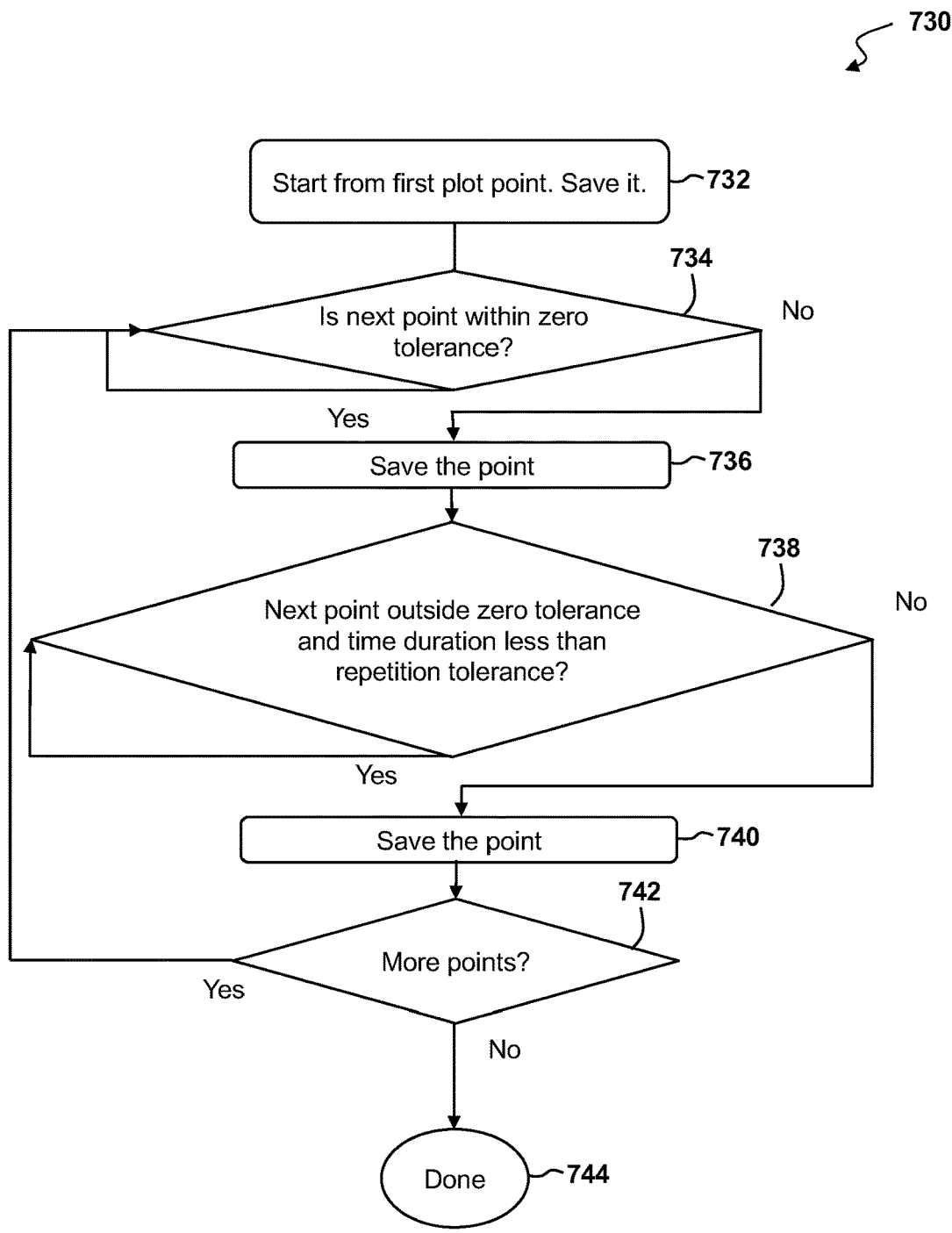
FIG. 5D shows a flowchart to find the zero band points.

FIG. 5D presents an exemplary embodiment of the Zero band point calculation algorithm 730. Start from the first compensated velocity plot value and save this value (step 732). Since the exercise machine starts from rest, this value will be within the zero tolerance band. In another embodiment, acceleration or displacement may be used. If the next points are within Zero tolerance band (step 734), ignore them, and save the point that is outside the Zero tolerance (step 736). Ignore the next points that are outside the Zero tolerance while the time duration is less than repetition tolerance (step 738), and save the point that does not meet this criterion (step 740). If there are more points left (step 742), check if the next point is within zero tolerance (step 734). The algorithm completes when no more points are left (step 744).

Figure 5E:
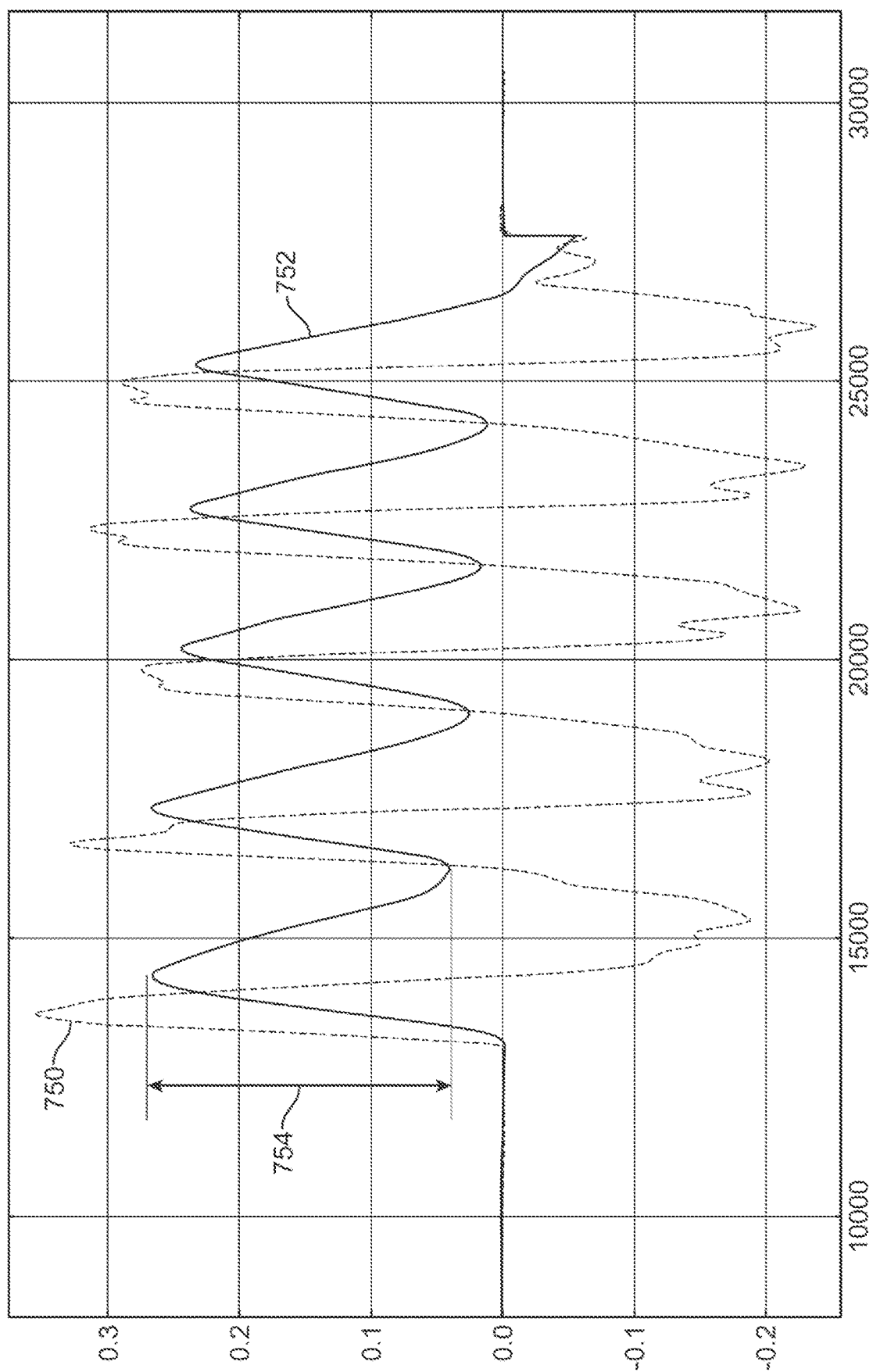
FIG. 5E shows a compensated displacement plot.

FIG. 5E shows an example of the compensated displacement plot 752 from the acceleration sensor for the z-axis plotted against time. The accelerometer sensor is mounted such that the z-axis is pointing upwards which is along the weight movement direction. This data is generated from a Type-A Active sensor link 602 (e.g., FIG. 4A). The displacement is area under the velocity curve and is computed by taking the cumulative sum of the velocity values.

In another embodiment, filtered acceleration values may be used to compute velocity. Compensation may then be applied and the velocity is filtered to further remove drift. To compute displacement, this filtered and compensated velocity curve 750 may be used and the area under the curve is computed. Drift may further be removed by applying the compensation algorithm.

Applying filter and compensation algorithms introduces delays in computing due to the nature of these operations. So, in one embodiment, the real time reporting of weight lifted, number of sets, repetitions, lifting speed etc. is done using just the acceleration data. Other information like range, energy, maximum power, and/or calorie information may be computed using filters and compensation algorithms and may be sent later.

During this exercise, the user completed one set and five repetitions. In this plot, the repetitions show up as the five troughs. As expected, the displacement plot 752 is much smoother than the velocity plot 750, but the displacement plot also shows a drift. This drift is compensated using the same algorithm that was used to compensate velocity plot drift.

Using the displacement plot, the range 754 can be computed. This is the distance that the weight is moved by the user. It may be one of the parameters 190 (e.g., FIG. 2A) used in the training plan.

Figure 5F:
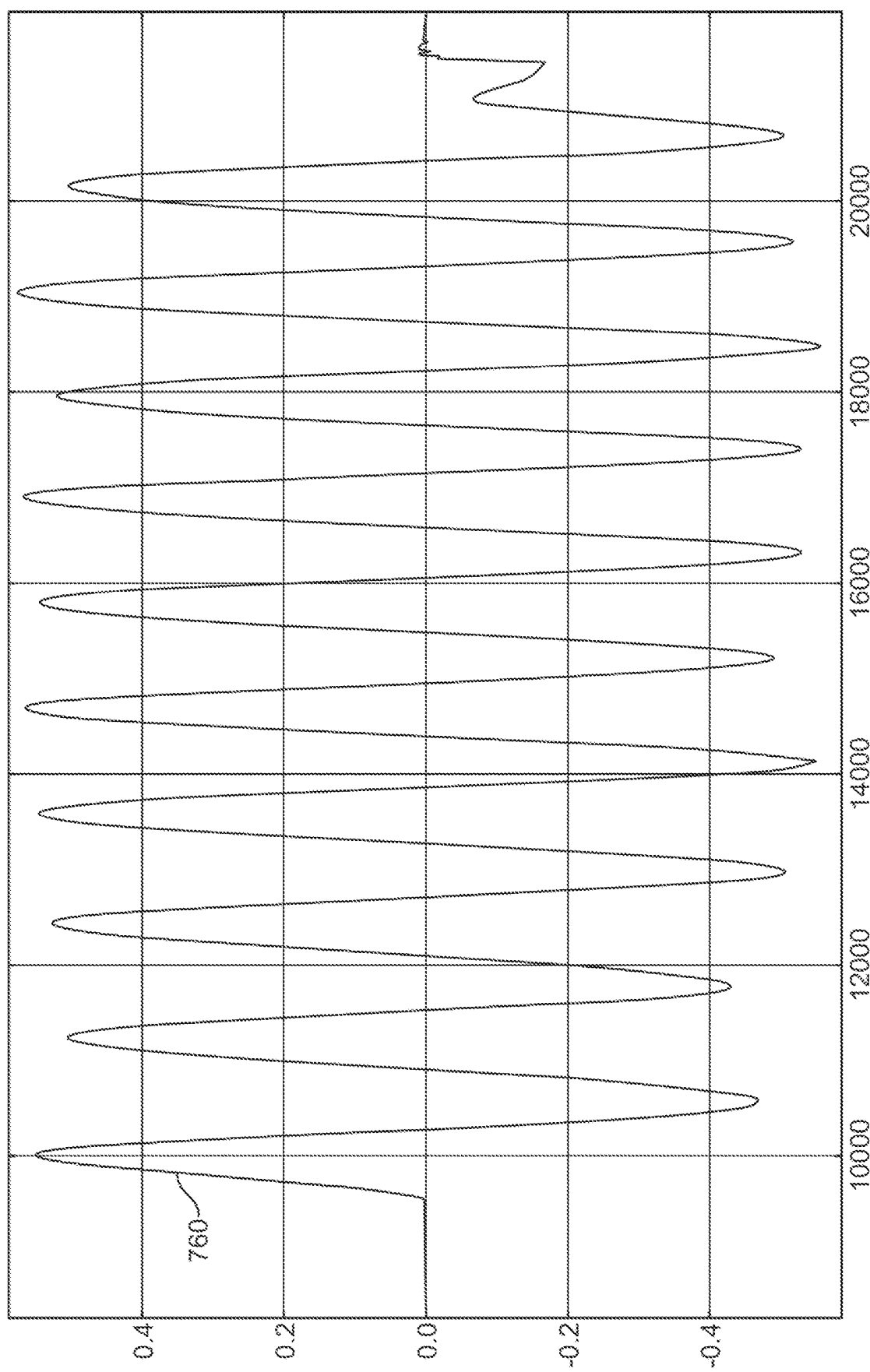
FIG. 5F shows a movement graph created by a trainer.

FIG. 5F shows an example of the compensated velocity plot 760 from the acceleration sensor for the z-axis plotted against time. The accelerometer sensor is mounted such that the z-axis is pointing upwards which is along the weight movement direction. This data is generated from a Type-A Active sensor link 602 (e.g., FIG. 4A).

During this exercise, the user completed one set and ten repetitions. This plot may be recorded by the trainer and used as the movement graph 192 (e.g., FIG. 2A), which is part of the training plan.

Figure 5G:
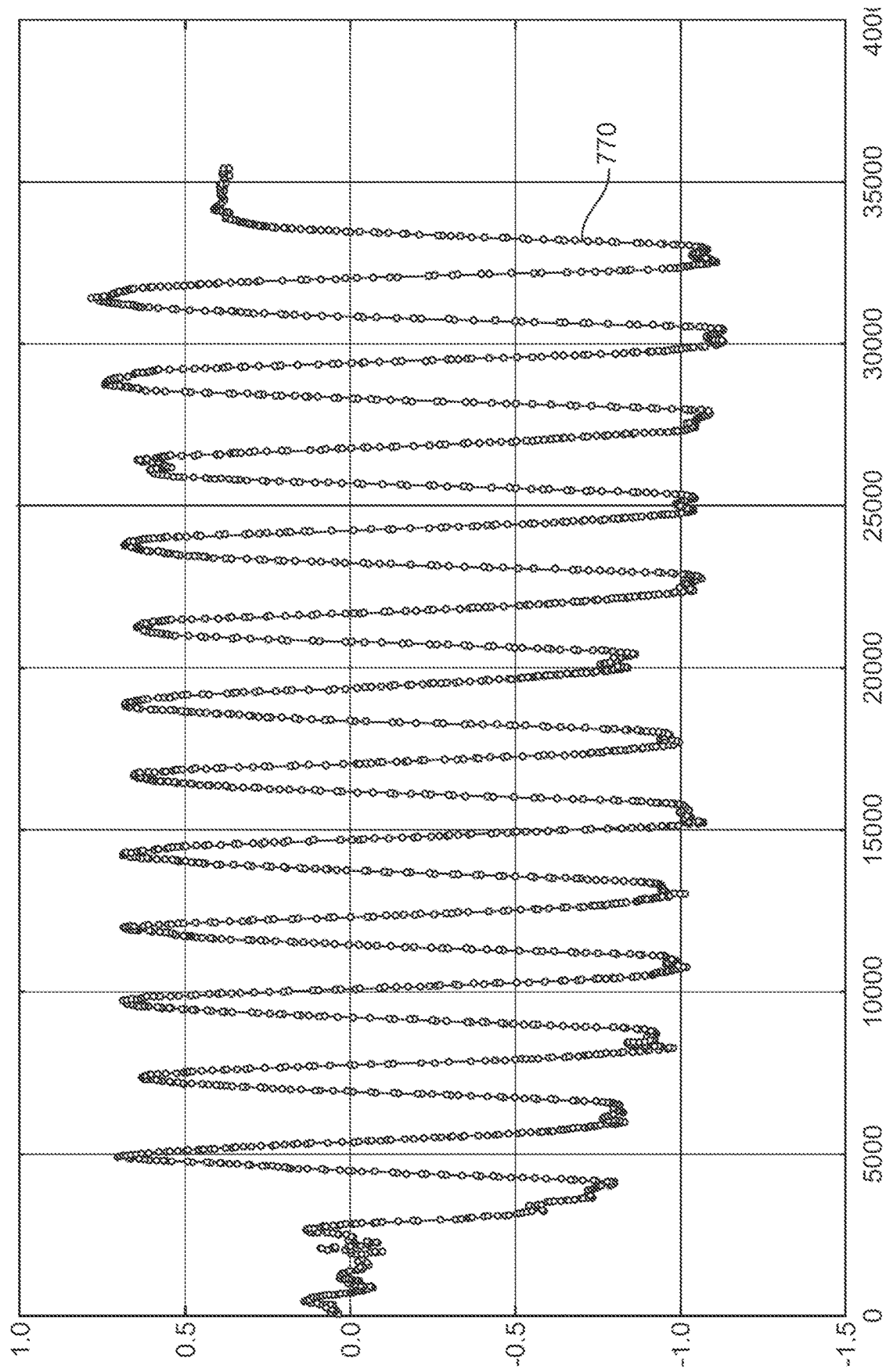
FIG. 5G shows an acceleration plot for a dumbbell.

FIG. 5G shows an example of an acceleration plot 770 from the acceleration sensor for the X-axis plotted against time. This data is generated from the Type-A Active sensor link 602 (e.g., FIG. 4A) mounted on a dumbbell.

During this exercise, the user completed one set and twelve repetitions, which corresponds to the number of troughs in the acceleration plot. Since the resting position of a dumbbell may not be fixed, the acceleration may not be zero at any time.

In one embodiment, the algorithms developed for weight machine can also be applied to free weights like dumbbell to compute the number of sets, repetitions, lifting and dropping time and range.

Figure 5H:
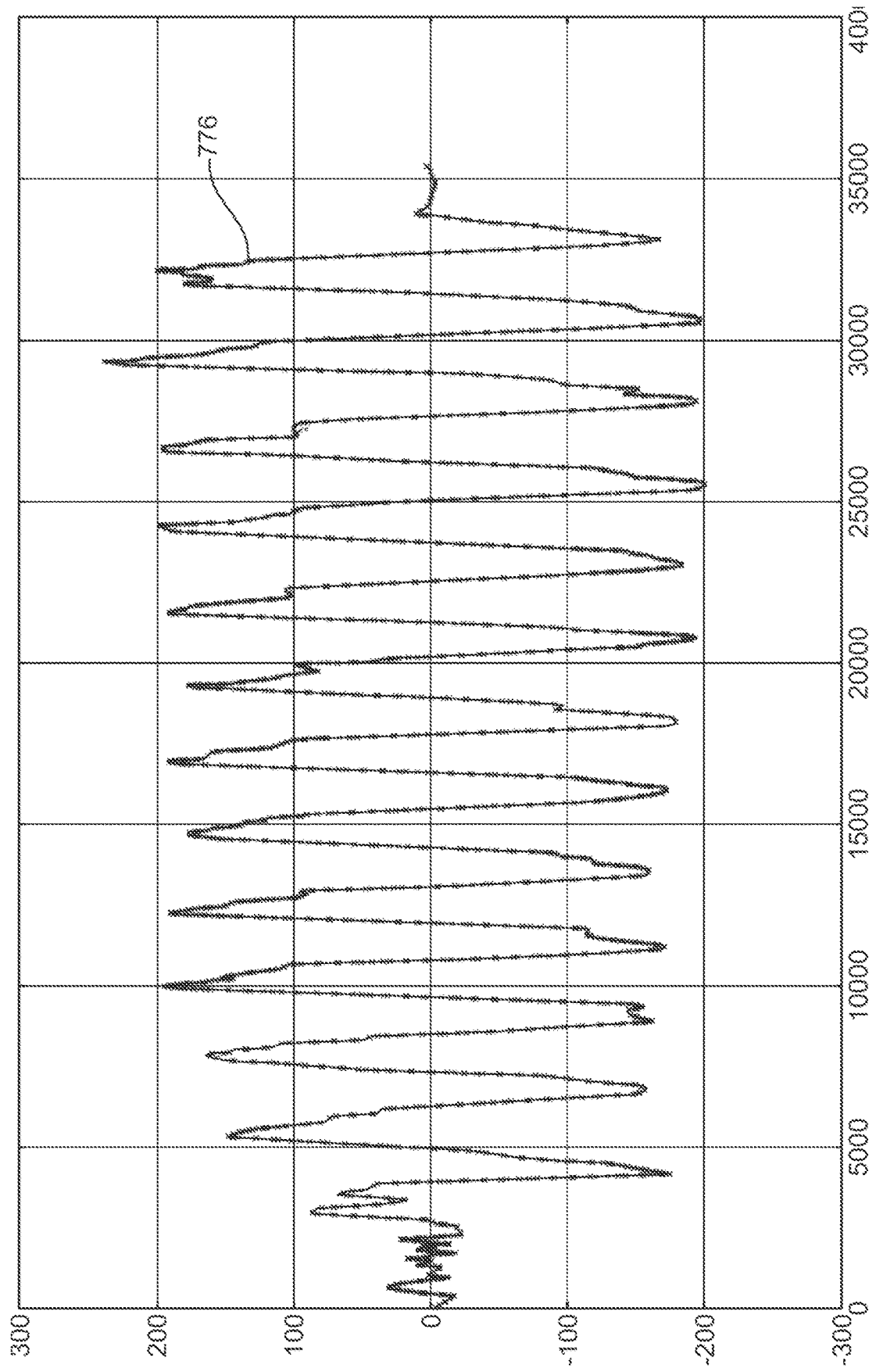
FIG. 5H shows an angular momentum plot for a dumbbell

FIG. 5H shows an example of an angular momentum plot 776 from the gyroscope sensor for the Y-axis plotted against time. This data is generated from the Type-A Active sensor link 602 (e.g., FIG. 4A) mounted on a dumbbell.

During this exercise, the user completed one set and twelve repetitions, which corresponds to the number of troughs in the angular momentum plot. Even though the resting position of a dumbbell is not fixed, the angular momentum does go to zero when the movement stops.

In another embodiment, the algorithms developed for weight machine can also be applied to free weights like dumbbell to compute the number of sets, repetitions, lifting and dropping time and range.

Note that references throughout this specification to "an aspect" or "one aspect" mean that a particular feature, structure or characteristic described in connection with the aspect is included in at least one aspect of the present invention. Therefore, it is emphasized and should be appreciated that two or more references to "an aspect" or "one aspect" or "an alternative aspect" in various portions of this specification are not necessarily all referring to the same aspect. Furthermore, the particular features, structures or characteristics being referred to may be combined as suitable in one or more aspects of the invention, as will be recognized by those of ordinary skill in the art.

It is contemplated that various combinations and/or sub-combinations of the specific features and aspects of the above embodiments may be made and still fall within the scope of the invention. Accordingly, it should be understood that various features and aspects of the disclosed embodiments may be combined with or substituted for one another in order to form varying modes of the disclosed invention. Further, it is intended that the scope of the present invention is herein disclosed by way of examples and should not be limited by the particular disclosed embodiments described above.

What is claimed is:

1. An Exercise Management System (EMS) comprising:
one or more weight sensors, wherein at least one of the one or more weight sensors comprise a strain gauge, and wherein a weight sensor of the one or more weight sensors is disposed in a barbell, wherein the weight sensor compensates for an orientation of the barbell with respect to ground;
one or more motion sensors, wherein a motion sensor of the one or more motion sensors is mounted on a sleeve of the barbell; and
a processor having memory, the processor configured to:
determine a weight lifted on an exercise equipment based on a measured strain of one or more weight sensors; and
determine a movement of the weight lifted on the exercise equipment based on a measured motion of one or more motion sensors.

2. The EMS of claim 1, further comprising:
one or more relief features, wherein the one or more relief features concentrate a weight in at least one predefined and fixed area relative to the one or more weight sensors.

3. The EMS of claim 1, wherein the processor is further configured to:
determine, based on the determined weight and the determined movement of the weight, at least one of: a number of sets, a number of repetitions, a lifting speed, a range of motion of the weight, an energy, a maximum power, and a total calories spent.

4. The EMS of claim 3, wherein the processor is further configured to:
form a user exercise data based on the determined at least one of: the number of sets, the number of repetitions, the lifting speed, the range of motion of the weight, the energy, the maximum power, and the total calories spent; and
transmit the formed user exercise data to a cloud server.

5. The EMS of claim 1, wherein the processor is further configured to:
measure usage patterns, wherein a club management module provides the usage patterns to a fitness center operator for determining one or more of: preventative maintenance based on equipment use, time and efficiency changes, usage time slot scheduling, and exercise equipment use frequency.

6. The EMS of claim 1, wherein the processor is further configured to:
couple the determined weight lifted and the determined motion of the weight lifted based on matching a timing of lifting events.

7. An Exercise Management System (EMS) comprising:
a weight sensor of one or more weight sensors disposed in a weight pin of an exercise equipment, wherein the weight sensor measures a weight lifted, wherein the weight pin further comprises one or more pin relief features, wherein the one or more pin relief features concentrates the weight and support forces on one or more predefined and fixed areas of the weight pin, and wherein the one or more pin relief features comprise two pin relief features disposed about each of the one or more weight sensors;
a rotation sensor of one or more rotation sensors disposed about the weight pin, wherein the rotation sensor measures the movement of a cable of the exercise equipment about a rotatable pulley; and a processor having memory, the processor configured to:
- determine a weight lifted on the exercise equipment based on a measured strain of one or more weight sensors of the one or more sensors; and
- determine a movement of the weight lifted on the exercise equipment based on a measured motion of one or more motion sensors of the one or more sensors.

8. The EMS of claim 7, wherein at least one of the one or more weight sensors comprise a strain gauge.

9. The EMS of claim 7, wherein the weight sensor compensates for an orientation of the weight lifted with respect to ground.

10. The EMS of claim 7, wherein the processor is further configured to:
- determine, based on the determined weight and the determined movement of the weight, at least one of: a number of sets, a number of repetitions, a lifting speed, a range of motion of the weight, an energy, a maximum power, and a total calories spent.

11. The EMS of claim 10, wherein the processor is further configured to:
- form a user exercise data based on the determined at least one of: the number of sets, the number of repetitions, the lifting speed, the range of motion of the weight, the energy, the maximum power, and the total calories spent; and
- transmit the formed user exercise data to a cloud server.

12. The EMS of claim 7, wherein the processor is further configured to:
- measure usage patterns, wherein a club management module provides the usage patterns to a fitness center operator for determining one or more of: preventative maintenance based on equipment use, time and efficiency changes, usage time slot scheduling, and exercise equipment use frequency.

13. The EMS of claim 7, wherein the processor is further configured to:
- couple the determined weight lifted and the determined motion of the weight lifted based on matching a timing of lifting events.

* * * * *